United States Patent
Saijo et al.

(10) Patent No.: US 9,981,059 B2
(45) Date of Patent: May 29, 2018

(54) SUGAR CHAIN-POLYPEPTIDE COMPLEX

(71) Applicant: Glytech, Inc., Kyoto-shi Kyoto (JP)

(72) Inventors: Hayato Saijo, Kyoto (JP); Hirofumi Ochiai, Kyoto (JP); Keisuke Tazuru, Kyoto (JP); Taiji Shimoda, Kyoto (JP)

(73) Assignee: GLYTECH, INC., Kyoto (JP)

( * ) Notice: Subject to any disclaimer, the term of this patent is extended or adjusted under 35 U.S.C. 154(b) by 0 days. days.

(21) Appl. No.: 14/780,417

(22) PCT Filed: Mar. 21, 2014

(86) PCT No.: PCT/JP2014/057927
§ 371 (c)(1),
(2) Date: Dec. 7, 2015

(87) PCT Pub. No.: WO2014/162906
PCT Pub. Date: Oct. 9, 2014

(65) Prior Publication Data
US 2016/0129150 A1 May 12, 2016

(30) Foreign Application Priority Data
Mar. 30, 2013 (JP) ................................. 2013-075493

(51) Int. Cl.
*A61K 38/14* (2006.01)
*C07K 9/00* (2006.01)
*A61L 26/00* (2006.01)
*A61K 47/42* (2017.01)
*A61L 33/12* (2006.01)
*A61L 15/32* (2006.01)
*A61K 47/61* (2017.01)

(52) U.S. Cl.
CPC ............ *A61L 26/008* (2013.01); *A61K 47/42* (2013.01); *A61K 47/61* (2017.08); *A61L 15/32* (2013.01); *A61L 26/009* (2013.01); *A61L 26/0028* (2013.01); *A61L 26/0047* (2013.01); *A61L 33/12* (2013.01); *A61L 2300/418* (2013.01); *A61L 2300/604* (2013.01); *A61L 2400/04* (2013.01)

(58) Field of Classification Search
CPC ............................... A61K 38/00; A61K 38/14
See application file for complete search history.

(56) References Cited

U.S. PATENT DOCUMENTS 5,670,483 A 9/1997 Zhang et al.
2008/0274979 A1 11/2008 Ellis-Behnke et al.
2010/0016548 A1 1/2010 Yokoi et al.
2011/0201541 A1 8/2011 Takamura et al.
2014/0045951 A1 2/2014 Uesugi et al.

FOREIGN PATENT DOCUMENTS

| EP | 2703014 | 3/2014 | |
|---|---|---|---|
| JP | 2007217376 | 8/2007 | |
| JP | 2010/521495 A | 6/2010 | |
| JP | 2012082180 | 4/2012 | |
| WO | WO 2008/113030 A2 | 9/2008 | |
| WO | WO 2008113030 A2 * | 9/2008 | ............. A61K 38/07 |

OTHER PUBLICATIONS

Merriam-Webster, Oligosaccharide | Definition of Oligosaccharide by Merriam-Webster, available online at: https://www.merriam-webster.com/dictionary/oligosaccharide, accessed on Jul. 6, 2017.*
International Search Report corresponding to PCT/JP2014/057927; dated Jun. 24, 2014.
Bosques, C.J. et al., Effects of glycosylation on peptide conformation: a synergistic experimental and computational study, Journal of the American Chemical Society, Jun. 18, 2004, vol. 126, No. 27, p. 8421-8425.
European Search Report corresponding to International Patent Application No. PCT/JP2014057927, dated Oct. 10, 2016, 10 pages.
Peluso S. et al., "Asparagine surrogates for assembly of N-linked glycopeptide mimetics by chemoselective ligation", Tetrahedron Letters, Pergamon, GB, vol. 42, No. 11, Mar. 11, 2001, pp. 2085-2087.
Ying Zhao et al., "Controlled release and interaction of protein using self-assembling peptide RATEA16 nanofiber hydrogels", Journal of Polymer Science Part A: Polymer Chemistry, vol. 46, No. 14, Jul. 15, 2008, pp. 4927-4933.
Ying Zhao et al., "Self-Assembled pH-Responsive Hydrogels Composed of the RATEA16 Peptide", Biomacromolecules, vol. 9, No. 6, Jun. 1, 2008, pp. 1511-1518.
Sola, Ricardo et al, "Effects of Glycosylation on the Stability of Protein Pharmaceuticals", *J Pharm. Sci.*, 98(4), pp. 1223-1245 (2009).
Lawson, Erlinda et al. "Effect of Carbohydrate on Protein Solubility", *Arch Biochem. Biophys.*, 220(2):pp. 572-575 (1983).
Office Action corresponding to Russian Patent Application No. RU2011118341A, dated Jan. 26, 2018, 5 pages.

* cited by examiner

*Primary Examiner* — Hasan S Ahmed
*Assistant Examiner* — Kaipeen E Yang
(74) *Attorney, Agent, or Firm* — Myers Bigel, P.A.

(57) ABSTRACT

The object of the present invention is to provide a sugar chain-polypeptide complex that may form a transparent and homogeneous hydrogel in a broad pH. The present invention provides a sugar chain-polypeptide complex, characterized in that said polypeptide is a polypeptide comprising an amino acid sequence consisting of 8-34 amino acid residues in which polar and nonpolar amino acid residues are alternately arranged, and one or more sugar chains are bound to said polypeptide.

17 Claims, 4 Drawing Sheets

SUGAR CHAIN-POLYPEPTIDE COMPLEX

STATEMENT REGARDING ELECTRONIC FILING OF A SEQUENCE LISTING

A Sequence Listing in ASCII text format, submitted under 37 C.F.R. § 1.821, entitled 9778-14_ST25.txt, 31,439 bytes in size, generated on Feb. 15, 2018and filed via EFS-Web, is provided in lieu of a paper copy. This Sequence Listing is hereby incorporated by reference into the specification for its disclosures.

TECHNICAL FIELD

The present invention relates to a sugar chain-polypeptide complex in which a sugar chain is bound to a polypeptide.

BACKGROUND ART

Biogels such as hydrogel and fibrin glue are utilized as research matrix for three dimensional culture etc., surgical matrix such as pre/post-operation hemostatics or wound healing sheets, drug delivery system (DDS), and the like.

However, since many of these employ materials of biological origin, risks such as infection from microorganisms such as viruses, immunogenicity, and transmission of diseases exist with use thereof. For example, although fibrin glue has high utility value as a hemostatic during surgery, because the source material is derived from human blood, there had been multiple cases of patients being infected by hepatitis virus that had contaminated the fibrin glue upon actual use during surgery, thus causing a major social problem. There is also a problem that gels of homogeneous quality can not always be supplied with biogels of biological origin.

In contrast to biogels of biological origin, biogels manufactured by chemical synthesis are known to have no risk of infection and be capable of providing gels of homogeneous quality (Patent Literature 1). However, biogels known to date require procedures such as buffer exchange or substitution and mixing of multiple agents when forming a gel, and operation is complicated. Moreover, not only reagents or solvents to be used in combination are limited because solubility is low depending on the pH range, but there are also problems such as limitation of applicable sites (affected sites) and clogging of syringes or tubes upon use. In addition, low solubility (i.e. not transparent), particularly in the neutral range which is close to the biological pH, will complicate employment in situations that require visibility such as the surgery field.

CITATION LIST

[Patent Literature 1] U.S. Pat. No. 5,670,483

SUMMARY OF THE INVENTION

Problem to be Solved by the Invention

The object of the present invention is to provide a sugar chain-polypeptide complex that may form a transparent and homogeneous hydrogel in a broad pH.

Means for Solving the Problem

As a result of extensive investigation by the present inventors to solve said problem, it was surprisingly found that a sugar chain-polypeptide complex manufactured by binding a sugar chain to a polypeptide comprising an amino acid sequence in which polar and nonpolar amino acid residues are alternately arranged shows high water-solubility and forms a transparent and homogeneous hydrogel in a broad pH range, particularly in the neutral range, thus leading to the completion of the present invention.

In other words, the present invention provides a sugar chain-polypeptide complex characterized in that said polypeptide is a polypeptide comprising an amino acid sequence consisting of 8-34 amino acid residues in which polar and nonpolar amino acid residues are alternately arranged, and one or more sugar chains are bound to said polypeptide.

Moreover, one embodiment of the present invention is characterized in that said sugar chain-polypeptide complex may form a hydrogel comprising a β sheet structure by self-assembly in an aqueous solution having a pH around neutral.

Moreover, one embodiment of the present invention is characterized in that each of said polar amino acid residue is an amino acid residue selected from the group consisting of an aspartate residue, a glutamate residue, an arginine residue, a lysine residue, a histidine residue, a tyrosine residue, a serine residue, a threonine residue, an asparagine residue, a glutamine residue, and a cysteine residue.

Moreover, one embodiment of the present invention is characterized in that each of said nonpolar amino acid residue is an amino acid residue selected from the group consisting of an alanine residue, a valine residue, a leucine residue, an isoleucine residue, a methionine residue, a phenylalanine residue, a tryptophan residue, a proline residue, and a glycine residue.

Moreover, one embodiment of the present invention is characterized in that each of said polar amino acid residue is an amino acid residue selected from the group consisting of an aspartate residue, a glutamate residue, an arginine residue, and a threonine residue, and each of said nonpolar amino acid is an alanine residue.

Moreover, one embodiment of the present invention is characterized in that said amino acid sequence is a repetitive sequence "RADA" or a repetitive sequence "RATARAEA."

Moreover, one embodiment of the present invention is characterized in that said amino acid sequence is an amino acid sequence selected from the group consisting of RADARADARADARADA (SEQ ID NO. 1), RADARADARADARADARADA (SEQ ID NO. 2), and RATARAEARATARAEA (SEQ ID NO. 3).

Moreover, one embodiment of the present invention is characterized in that the total number of sugar residues present in the one or more sugar chains bound to said polypeptide is 5 or more.

Moreover, one embodiment of the present invention is characterized in that the number of sugar chains bound to said polypeptide is 1, 2, or 3.

Moreover, one embodiment of the present invention is characterized in that sugar chains are bound to every amino acid up to position x counting from the amino acid residue positioned at the N-terminal of said polypeptide and every amino acid up to position y counting from the amino acid residue positioned at the C-terminal (wherein x and y are integers, x≥0, y≥0, and x+y is the total number of sugar chains bound to the polypeptide).

Moreover, one embodiment of the present invention is characterized in that the number of sugar chains bound to said polypeptide is 1, 2, or 3, in which when the number of sugar chains bound to said polypeptide is 1, said one sugar chain is bound to the amino acid residue positioned at the N-terminal of said polypeptide or the amino acid residue positioned at the C-terminal, when the number of sugar chains bound to said polypeptide is 2, said two sugar chains are bound to amino acid residues selected from the group consisting of (1)-(3) below:

(1) the first and second amino acid residues counting from the amino acid residue positioned at the N-terminal of said polypeptide,
(2) the first and second amino acid residues counting from the amino acid residue positioned at the C-terminal of said polypeptide, and
(3) the amino acid residue positioned at the N-terminal of said polypeptide and the amino acid residue positioned at the C-terminal of said polypeptide, and when the number of sugar chains bound to said polypeptide is 3, said three sugar chains are bound to any amino acid residue selected from the group consisting of (1)-(4) below:

(1) the first, second, and third amino acid residues counting from the amino acid residue positioned at the N-terminal of said polypeptide,
(2) the first, second, and third amino acid residues counting from the amino acid residue positioned at the C-terminal of said polypeptide,
(3) the first and second amino acid residues counting from the amino acid residue positioned at the N-terminal of said polypeptide, as well as the amino acid residue positioned at the C-terminal of said polypeptide, and
(4) the amino acid residue positioned at the N-terminal of said polypeptide, as well as amino acid residues positioned at position 1 and 2 counting from the C-terminal of said polypeptide.

Moreover, one embodiment of the present invention is characterized in that said sugar chain is a sugar chain with a branch.

Moreover, one embodiment of the present invention is characterized in that said sugar chain is a sugar chain selected from the group consisting of a disialo sugar chain, an asialo sugar chain, a diGlcNAc sugar chain, a dimannose sugar chain, a GlcNAc sugar chain, a maltotriose sugar chain, a maltose sugar chain, a maltotetraose sugar chain, a maltoheptaose sugar chain, β-cyclodextrin, and γ-cyclodextrin.

Moreover, one embodiment of the present invention is characterized in that it is a composition for hydrogel formation comprising the sugar chain-polypeptide complex of the present invention. In addition, such a composition for hydrogel formation may be a hemostatic pharmaceutical composition, a composition for controlled release carrier, or a composition for culture matrix.

Moreover, one embodiment of the present invention is characterized in that it is a composition comprising the sugar chain-polypeptide complex of the present invention wherein said composition is in a hydrogel state. In addition, such a composition may be a hemostatic pharmaceutical composition, a composition for controlled release carrier, or a composition for culture matrix.

Those skilled in the art shall recognize that an invention of any combination of one or more characteristics of the present invention described above is also encompassed in the scope of the present invention.

Effects of the Invention

Because the sugar chain-polypeptide complex according to the present invention has high water-solubility in a broad pH range comprising the neutral range and forms a uniform and transparent hydrogel, it is less subject to limitation from reagents or solvents that are used in combination, and may be employed for various applications. Moreover, because it may be employed in a broad pH range, it is less subject to limitation of applicable sites (affected sites).

Moreover, because the sugar chain-polypeptide complex according to the present invention has high water-solubility in a broad pH range comprising the neutral range and forms a uniform and transparent hydrogel, sol and gel states may be reversibly present in a neutral pH. In other words, the sugar chain-polypeptide complex can form a gel state once and then be in a sol state by mechanical stirring, and still be in a gel state again. Accordingly, it can be distributed in a gel state (i.e. a Ready-to-Use state), and does not require complicated operations as with other peptidic gels such as buffer exchange (or substitution) in order to achieve a neutral pH after forming a gel at a pH suitable for gelling (e.g. acidic pH). In other words, the sugar chain-polypeptide complex according to the present invention is extremely superior in operativity compared to other peptidic gels. In addition, because the pH range that the sugar chain-polypeptide complex according to the present invention can be used in is broad, problems such as clogging of syringes and tubes upon use occur less often.

Moreover, because the sugar chain-polypeptide complex according to the present invention is modified by a sugar chain that exists in vivo in animals, antigenicity is reduced compared to a peptide without any modification. In addition, the sugar chain-polypeptide complex according to the present invention has almost no risk of producing toxicity such as that seen with a compound modified with e.g. polyethylene glycol (PEG). Accordingly, the sugar chain-polypeptide complex according to the present invention has high safety for biological use.

Moreover, it is also clear from the Examples herein that the sugar chain-polypeptide complex according to the present invention forms a more transparent and uniform hydrogel compared to a polypeptide bound to PEG.

Moreover, because the sugar chain-polypeptide complex according to the present invention forms a uniform and transparent hydrogel under physiologic conditions (neutral range) and has low antigenicity, it is preferable as a hydrogel for in vivo animal use.

More specifically, because a hydrogel comprising the sugar chain-polypeptide complex according to the present invention has a characteristic to maintain a transparent and uniform gel state even under conditions comprising high concentration blood plasma in a neutral pH, it has high utility value as e.g. a hemostatic.

Further, because a hydrogel comprising the sugar chain-polypeptide complex according to the present invention has high controlled release when encapsulating either an acidic or a basic protein in a neutral pH, it has high utility value as a controlled release carrier for various substances.

DESCRIPTION OF EMBODIMENTS

Figure 1:
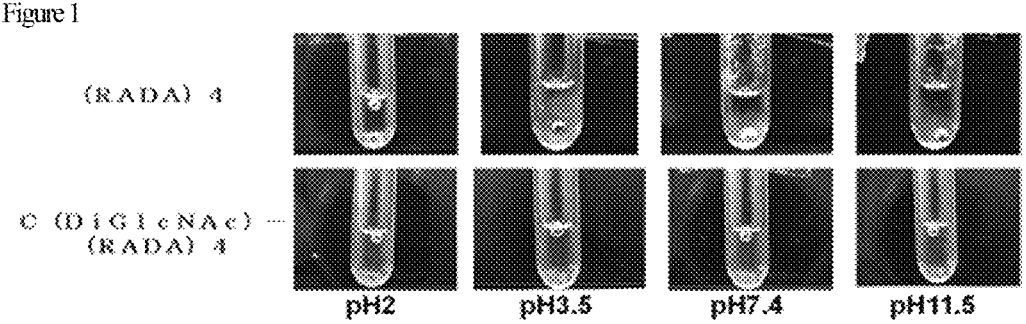
FIG. 1 is photographs showing the result of steel ball loading tests for (RADA)4 and C(DiGlcNAc)-(RADA)4 at various pH.

The sugar chain-polypeptide complex according to the present invention may be of biological origin or may be manufactured by chemical synthesis, but it is preferably manufactured by chemical synthesis from aspects of stability of safety or quality and uniformity of sugar chains.

The sugar chain-polypeptide complex according to the present invention may e.g. self-assemble in an aqueous solution via interactions such as electrostatic interaction between peptide molecules, hydrogen bonding, and hydrophobic interaction. A sugar chain-polypeptide complex "self-assembles" in an aqueous solution as used herein means that polypeptides spontaneously assemble with each other via some kind of interaction (e.g. electrostatic interaction, hydrogen bonding, van der Waals force, and hydrophobic interaction) in an aqueous solution, and is not to be construed as having a limiting meaning.

The sugar chain-polypeptide complex according to the present invention may self-assemble and form a β sheet structure in an aqueous solution. Further, a hydrogel may be formed by multiple layering of said β sheet structures. The method for confirming that the sugar chain-polypeptide complex forms a β sheet structure in an aqueous solution is not particularly limited, and it can be verified by e.g. measuring the circular dichroism (CD) of an aqueous solution comprising the sugar chain-polypeptide complex. Because generally as a characteristic of a molecule having β sheet structure positive absorbance is seen at a wavelength around 197 nm and negative absorbance is seen at a wavelength around 216 nm, β sheet structure formation can be confirmed by verifying peaks around these wavelengths by circular dichroism measurement.

Because the sugar chain-polypeptide complex according to the present invention comprises an amino acid sequence in which polar and nonpolar amino acid residues are alternately arranged, only polar amino acid residues may be arranged on one side of the β sheet structure and only nonpolar amino acid residues may be arranged on the other side when forming a β sheet structure in an aqueous solution. Accordingly, said β sheet structure may assemble in such a way to hide the hydrophobic sides (the sides with only nonpolar amino acid residues arranged) to form a bilayered structure. Subsequently, this β sheet layered structure will be extended as molecular self-assembly progresses to form a three dimensional conformation (e.g. a hydrogel). A polypeptide having such nature may be described herein as a SAP (Self-Assembling Peptide).

A "pH around neutral" as used herein means that the pH is around 7.0, more specifically that the pH is in the range of 5.0-9.0, preferably that the pH is in the range of 6.0-8.0.

One embodiment of the present invention is characterized in that the sugar chain-polypeptide complex may self-assemble in an aqueous solution having a pH around neutral to form a hydrogel comprising a β sheet structure. Those that may self-assemble even in an aqueous solution having a pH other than around neutral to form a hydrogel comprising a β sheet structure are not excluded, as long as they possess the said characteristic.

The sugar chain-polypeptide complex according to the present invention comprises a polypeptide comprising an amino acid sequence in which polar and nonpolar amino acid residues are alternately arranged. The length of said amino acid sequence is not limited, and preferably it may be an amino acid sequence consisting of 8-34 amino acid residues, more preferably an amino acid sequence consisting of 12-25 amino acid residues, and further preferably an amino acid sequence consisting of 16-21 amino acid residues.

The sugar chain-polypeptide complex according to the present invention comprises a polypeptide comprising an amino acid sequence in which polar and nonpolar amino acid residues are alternately arranged. An "amino acid" as used herein is employed in its broadest meaning, and comprises not only protein-constituting amino acids but also non-protein-constituting amino acids such as amino acid variants and derivatives. Those skilled in the art shall recognize in light of this broad definition that examples of an amino acid herein include protein-constituting L-amino acids; D-amino acids; chemically modified amino acids such as amino acid variants and derivatives; non-protein-constituting amino acids such as norleucine, β-alanine, and ornithine; as well as chemically synthesized compounds having properties well-known in the art that are characteristics of amino acids. Examples of a non-protein-constituting amino acid include α-methylamino acids (such as α-methylalanine), D-amino acids, histidine-like amino acids (such as 2-amino-histidine, β-hydroxy-histidine, homohistidine, α-fluoromethyl-histidine, and α-methyl-histidine), amino acids having excess methylene on the side chain ("homo" amino acids), and amino acids having the carboxylate functional group amino acid in the side chain substituted by a sulfonate group (such as cysteic acid). In a preferred aspect of the present invention, the amino acids employed herein may be protein-constituting amino acids.

A polar amino acid residue as used herein is not particularly limited as long as it is an amino acid residue of which the side chain may have polarity, examples of which include acidic amino acid residues and basic amino acid residues. Examples of an acidic amino acid residue as used herein include an aspartic acid (Asp: D) residue and glutamic acid (Glu: E), and examples of a basic amino acid include arginine (Arg: R), lysine (Lys: K), and histidine (His: H).

Note that for example representations such as "aspartic acid (Asp: D)" as used herein means that a three-letter representation "Asp" and one-letter representation "D" may be employed as abbreviations of aspartic acid.

Moreover, in the present specification, among neutral amino acid residues, amino acid residues comprising a hydroxyl group, an acid amide group, a thiol group, and the like are included in polar amino acid residues as those having polarity. For example, in the present specification, tyrosine (Tyr: Y), serine (Ser: S), threonine (Thr: T), asparagine (Asn: N), glutamine (Gln: Q), cysteine (Cys: C) are included in polar amino acid residues.

A nonpolar amino acid residue as used herein is not particularly limited as long as it is an amino acid of which the side chain does not have polarity, examples of which include alanine (Ala:A), valine (Val:V), leucine (Leu:L), isoleucine (Ile:I), methionine (Met:M), phenylalanine (Phe: F), tryptophan (Trp:W), glycine (Gly:G), and proline (Pro: P).

In the sugar chain-polypeptide complex according to the present invention, "an amino acid sequence in which polar and nonpolar amino acid residues are alternately arranged" is preferably those where said amino acid sequence may be a repetitive sequence "RADA" (2-8 repeats, preferably 3-6 repeats) or a repetitive sequence "RATARAEA" (1-4 repeats, preferably 2-3 repeats), and more preferably where said amino acid sequence may be an amino acid sequence selected from the group consisting of RADARADARA-DARADA (SEQ ID NO. 1), RADARADARADARA-DARADA (SEQ ID NO. 2), and RATARAEARATARAEA (SEQ ID NO. 3).

A "sugar chain" as used herein refers to a compound composed of a string of one or more unit sugars (monosaccharide and/or derivatives thereof). When it is a string of two unit sugars, each unit sugar is bound to each other by a dehydration condensation by a glycoside bond. Examples of such a sugar chain include, are but not limited to, a broad range such as monosaccharides and polysaccharides contained in vivo (glucose, galactose, mannose, fucose, xylose, N-acetylglucosamine, N-acetylgalactosamine, sialic acid, and complexes and derivatives thereof), as well as sugar chains that were degradated or induced from complex biomolecules such as degradated polysaccharides, glycoproteins, proteoglycans, glycosaminoglycans, and glycolipids. The sugar chain may be linear or branched chain.

A "sugar chain" as used herein also includes sugar chain derivatives. Examples of a sugar chain derivative include, but are not limited to, sugar chains wherein the sugar configuring the sugar chain is for example a sugar possessing a carboxy group (e.g. aldonic acid in which C-1 position is oxidized to become a carboxylic acid (such as D-gluconic acid which is oxidized D-glucose) and uronic acid in which the terminal C atom became a carboxylic acid (D-glucuronic acid which is oxidized D-glucose)), a sugar possessing an amino group or an amino group derivative (such as D-glucosamine and D-galactosamine), a sugar possessing both amino and carboxy groups (such as N-glycoylneuraminic acid and N-acetylmuramic acid), a deoxylated sugar (such as 2-deoxy-D-ribose), a sulfated sugar comprising a sulfate group, and a phosphorylated sugar comprising a phosphate group.

In the sugar chain-polypeptide complex according to the present invention, the sugar chain to be bound to the polypeptide is not particularly limited, but is preferably a sugar chain that exists in vivo as a glycoconjugate (such as a glycopeptide (or a glycoprotein), a proteoglycan, and a glycolipid) with respect to biocompatibility. Such sugar chains include N-linked sugar chains, O-linked sugar chain, and the like, which are sugar chains that are bound in vivo to peptides (or proteins) as glycopeptides (or glycoproteins).

In the sugar chain-polypeptide complex according to the present invention, for example a disialo sugar chain, an asialo sugar chain, a diGlcNAc sugar chain, a dimannose (DiMan) sugar chain, a GlcNAc sugar chain, a maltotriose sugar chain, a maltose sugar chain, a maltotetraose sugar chain, a maltoheptaose sugar chain, a β-cyclodextrin sugar chain, and a γ-cyclodextrin sugar chain can be employed for the sugar chain to be bound to the polypeptide.

More specifically, the sugar chain employed in the present invention may be a disialo sugar chain shown by the following Formula (1), a asialo sugar chain shown by the following Formula (2), a diGlcNAc sugar chain shown by the following Formula (3), a dimannose sugar chain shown by the following Formula (4), a GlcNAc sugar chain shown by the following Formula (5), a maltotriose sugar chain shown by the following Formula (6), a maltose sugar chain shown by the following Formula (7), a maltotetraose sugar chain shown by the following Formula (8), a maltoheptaose sugar chain shown by the following Formula (9), a β-cyclodextrin sugar chain shown by the following Formula (10), or a γ-cyclodextrin sugar chain shown by the following Formula (10-2).

[Chemical Formula 1]

Formula (1)

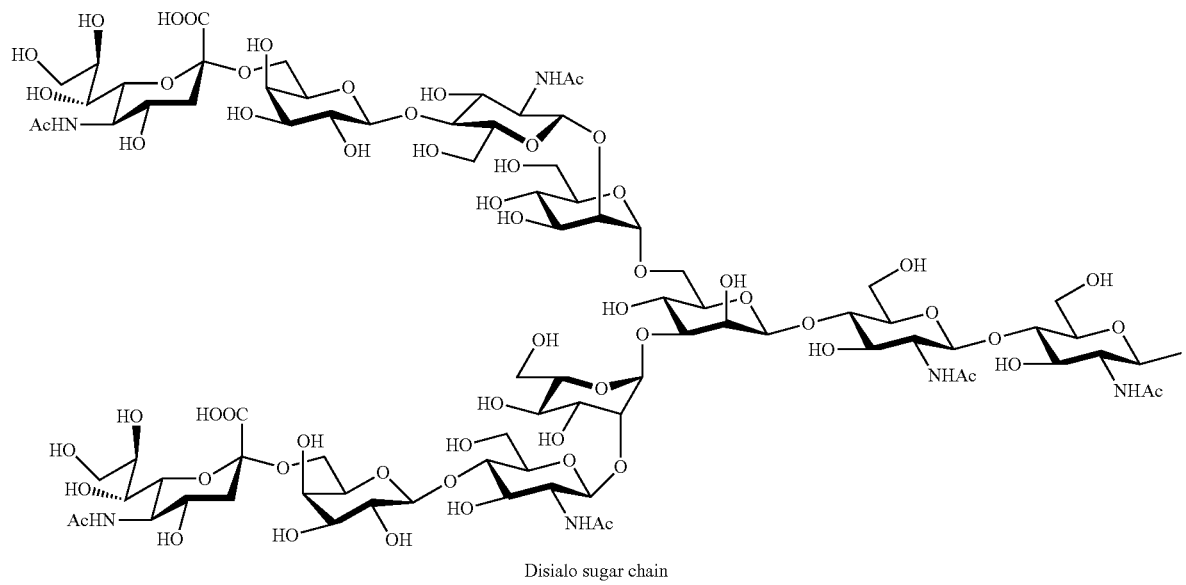

Disialo sugar chain

[Chemical Formula 2]
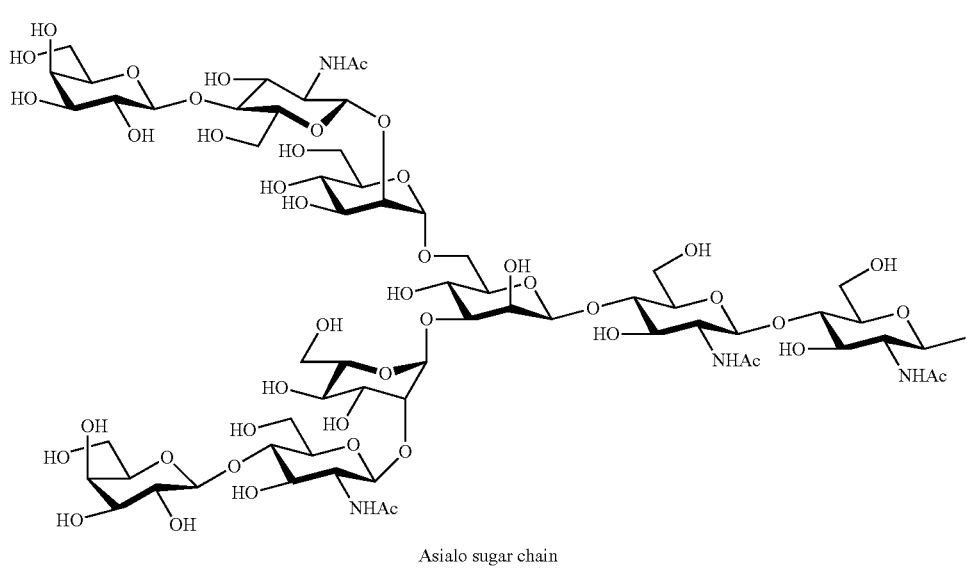
Formula (2)
Asialo sugar chain
[Chemical Formula 3]
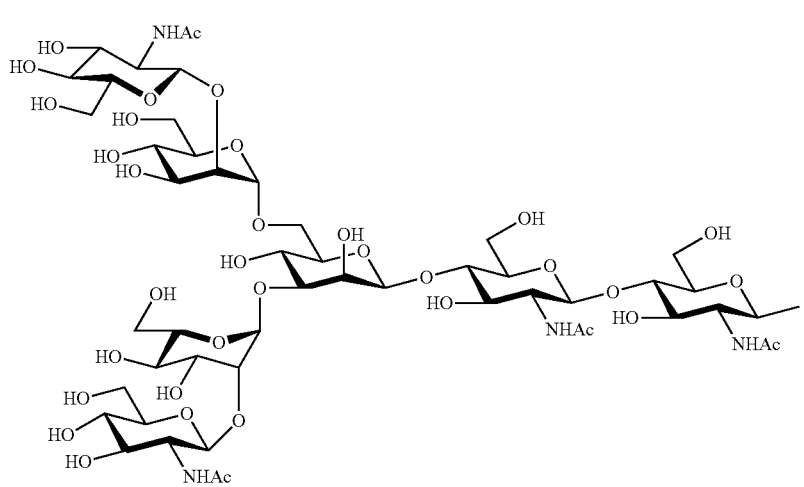
Formula (3)
DiGlcNAc sugar chain

[Chemical Formula 4]
Formula (4)
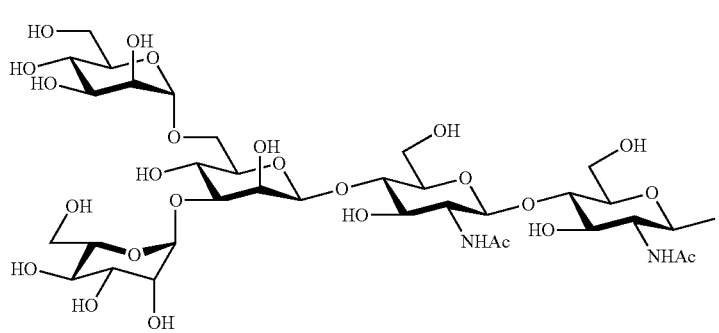
Dimannose sugar chain
[Chemical Formula 5]
Formula (5)
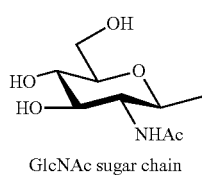
GlcNAc sugar chain
[Chemical Formula 6]
Formula (6)
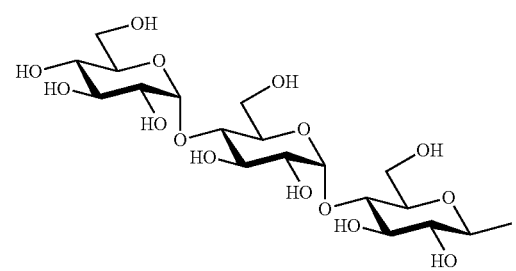
Maltotriose sugar chain
[Chemical Formula 7]
Formula (7)
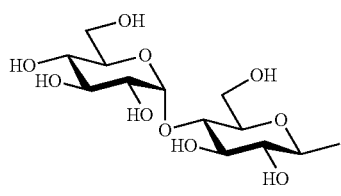
Maltose sugar chain
[Chemical Formula 8]
Formula (8)
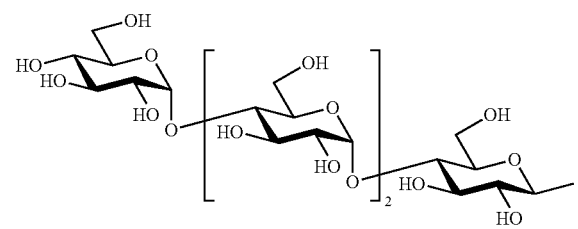
Maltotetraose sugar chain

[Chemical Formula 9]

Formula (9)

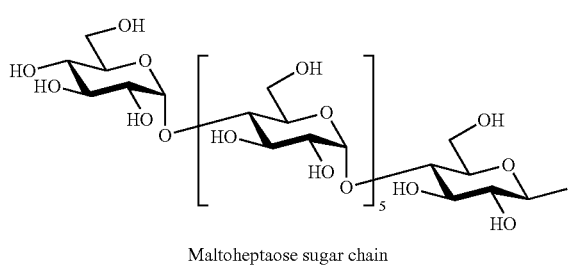

Maltoheptaose sugar chain

[Chemical Formula 10]

Formula (10)

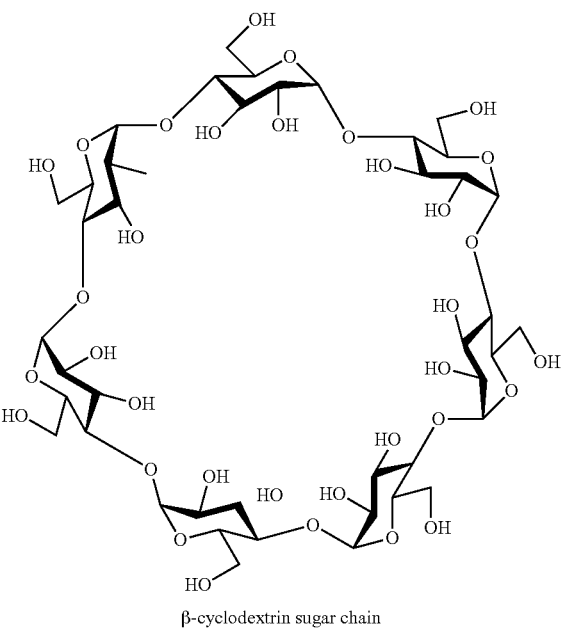

β-cyclodextrin sugar chain

[Chemical Formula 11]

Formula (10-2)

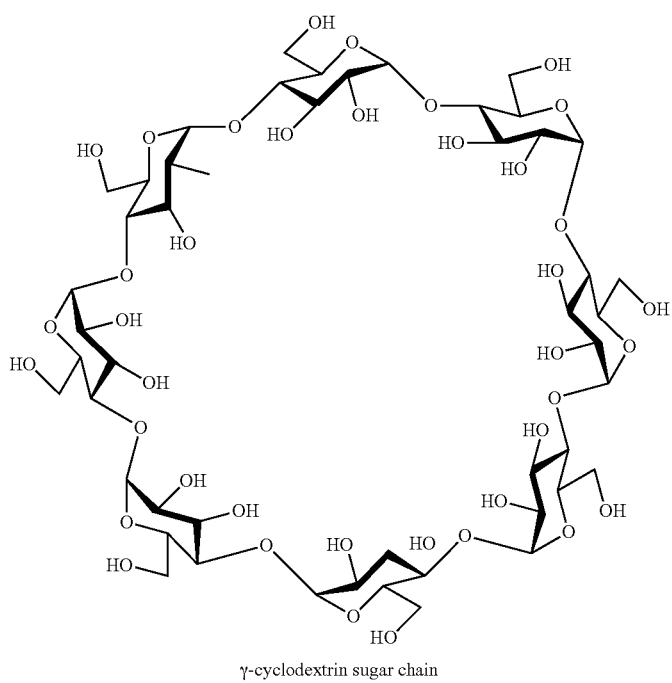

γ-cyclodextrin sugar chain

In the present invention, a sugar chain in which one or more sugars are lost from the non-reducing terminal of the above disialo sugar chain, asialo sugar chain, diGlcNAc sugar chain, dimannose sugar chain, or maltoheptaose sugar chain can also be employed.

In the present invention, the amino acid residue to which a sugar chain is bound is not particularly limited. For example, a sugar chain can be bound to cysteine (Cys: C) or asparagine (Asn: N), preferably to cysteine (Cys: C).

In the present invention, the method for binding a sugar chain to an amino acid is not particularly limited. For example, a sugar chain may be directly bound to an amino acid residue, or a sugar chain may be bound to an amino acid residue via a linker.

Moreover, in the present invention, the amino acid residue to which a sugar chain is bound may be directly bound to "an amino acid sequence in which polar and nonpolar amino acid residues are alternately arranged," or may be bound via e.g. a linker.

Examples of such a linker can include an alkyl chain or a PEG chain possessing amino and carboxy groups at both ends so that it can form peptide bonds with an amino acid. Examples of such a linker can include —NH—(CH$_2$)$_n$—CO— (wherein n is an integer and is not limited as long as it does not inhibit the linker function of interest, preferably an integer 1-15) or —NH—(CH$_2$CH$_2$O)$_m$—CH$_2$CH$_2$—CO— (wherein m is an integer and is not limited as long as it does not inhibit the linker function of interest, preferably an integer 1-7), more specifically —NH—(CH$_2$)$_{11}$—CO— (C12 linker) or —NH—(CH$_2$CH$_2$O)$_3$—CH$_2$CH$_2$—CO- (PEG linker) and the like.

The sugar chain-polypeptide complex of the present invention can be manufactured by integrating a glycosylation step into a polypeptide synthesis method well-known to those skilled in the art. Although a method utilizing an enzyme represented by transglutaminase can be employed for glycosylation, there are problems in this case such as the need for a large amount of the sugar chain to be added, complication of purification after the final step, and limitations on glycosylation positions and sugar chains that can be added. As a result, although it is possible to employ this in a small scale synthesis such as for assays, it cannot be said to be a practical method for a large scale manufacturing.

As specific examples of an easy manufacturing method of the sugar chain-polypeptide complex of the present invention, a method for manufacturing a sugar chain-polypeptide complex by using Asn having a sugar chain bound thereto (glycosylated Asn) and applying a well-known peptide synthesis method such as solid and liquid phase synthesis (Method A), and a method for manufacturing a sugar chain-polypeptide complex by manufacturing a polypeptide in which an arbitrary amino acid residue is Cys according to a well-known peptide synthesis method, and then glycosylating the Cys by chemical synthesis (Method B) will be illustrated below. Those skilled in the art will be able to manufacture sugar chain-polypeptide complexes by various methods by referring to these manufacturing methods.

These Methods A and B can also be carried out in a combination of two or more. In case of a small scale synthesis employed for assays etc., the above method can further be used in combination with a sugar chain elongation reaction by a transferase. Method A is described in International Publication No. 2004/005330 (US2005222382 (A1)) and Method B is described in International Publication No. 2005/010053 (US2007060543 (A1)), the disclosures of which are incorporated herein by reference in their entireties. Moreover, manufacturing of sugar chains having uniform sugar chain structure employed in Methods A and B are described in e.g. International Publication No. 03/008431 (US2004181054 (A1)), International Publication No. 2004/058984 (US2006228784 (A1)), International Publication No. 2004/058824 (US2006009421 (A1)), International Publication No. 2004/070046 (US2006205039 (A1)), and International Publication No. 2007/011055, the disclosures of which are incorporated herein by reference in their entireties.

Method for Manufacturing a Sugar Chain-Polypeptide Complex (Method A)

As outlined below, the sugar chain-polypeptide complex can be manufactured by e.g. solid phase synthesis employing Asn having a sugar chain bound thereto.

(1) The carboxy group of an amino acid having the amino group nitrogen protected with a lipophilic protecting group is bound to a resin. In this case, since the amino group nitrogen of the amino acid is protected with a lipophilic protecting group, self-condensation of amino acids with each other is prevented, and the resin and the amino acid react to form a bond.

(2) The lipophilic protecting group of the reactant obtained is detached to form a free amino group.

(3) This free amino group and the carboxy group of any amino acid having the amino group nitrogen protected with a lipophilic protecting group are subjected to an amidation reaction.

(4) The above lipophilic protecting group is detached to form a free amino group.

(5) The above steps (3) and (4) are repeated once or more times to yield a peptide of any number of any amino acids linked together, having a resin bound at one end and possessing a free amino group at the other end.

(6) When the free amino group of the peptide synthesized in above (5) is to be protected with an acetyl group, it is also preferred to acetylate with acetic anhydride, acetic acid, and the like.

(7) Finally, the resin is cleaved with an acid and a peptide having a desired amino acid sequence can be obtained.

Here, by employing a glycosylated Asn having the amino group nitrogen protected with a lipophilic protecting group instead of the amino acid having the amino group nitrogen protected with a lipophilic protecting group, and reacting the carboxy group of said asparagine moiety with the hydroxyl group of the resin in (1), a peptide possessing a glycosylated Asn at the C-terminal can be obtained.

Moreover, after (2), or after repeating (3) and (4) for any number of times that is once or more, by employing a glycosylated Asn having the amino group nitrogen protected with a lipophilic protecting group instead of the amino acid having the amino group nitrogen protected with a lipophilic protecting group in (3), a sugar chain can be bound at any position of the polypeptide.

In this way, by employing a glycosylated Asn having the amino group nitrogen protected with a lipophilic protecting group instead of the amino acid having the amino group nitrogen protected with a lipophilic protecting group two or more times in any of steps (1) and (3), sugar chains can be bound at any two or more positions of the polypeptide.

If, after binding the glycosylated Asn, the lipophilic protecting group is detached and a free amino group is formed, and step (7) is carried out immediately thereafter, a polypeptide possessing a glycosylated Asn at the N-terminal can be obtained.

A resin that provides the C-terminal as an amide group may be a resin ordinarily used in solid phase synthesis. For example, it is preferred to employ Rink-Amide-resin which is functionalized with an amino group (from Merck & Co., Inc.), Rink-Amide-PEGA resin (from Merck & Co., Inc.), or NH-SAL-resin (from Watanabe Chemical Industries, Ltd.). Moreover, Fmoc-NH-SAL-resin-linker (from Watanabe Chemical Industries, Ltd.) and the like may be bound to Amino-PEGA-resin which is functionalized with an amino group (from Merck & Co., Inc.) and the like. The C-terminal amino acid of the peptide can be amidated by cleaving this resin and the peptide by an acid.

Moreover, examples of a resin which makes the C-terminal a carboxylic acid that can be employed are 2-chlorotrityl chloride resin functionalized with chlorine (from Merck & Co., Inc.), Amino-PEGA resin functionalized with an amino group (from Merck & Co., Inc.), NovaSyn TGT alcohol resin possessing a hydroxyl group (from Merck & Co., Inc.), Wang resin (from Merck & Co., Inc.), HMPA-PEGA resin (from Merck & Co., Inc.), and the like. Moreover, a linker may be present between Amino-PEGA resin and the amino acid, and examples of such a linker can include 4-hydroxymethylphenoxyacetic acid (HMPA), 4-(4-hydroxymethyl-3-methoxyphenoxy)-butylacetic acid (HMPB), and the like. H-Cys(Trt)-Trityl Nova PEG resin in which the C-terminal amino acid is bound to a resin in advance (from Merck & Co., Inc.) and the like can also be employed.

In regards to the binding between a resin and an amino acid having the amino group nitrogen protected with a lipophilic protecting group, for example in order to use a resin possessing a hydroxyl group or a resin functionalized with chlorine, the carboxy group of the amino acid is subjected to an ester binding with the resin. Moreover, when employing a resin functionalized with an amino group, the carboxy group of the amino acid is bound to the resin by an amide bond.

Note that 2-chlorotrityl chloride resin is preferred in that it can prevent racemization of terminal Cys when elongating the peptide chain in solid phase synthesis.

Method for Manufacturing a Sugar Chain-Polypeptide Complex—2 (Method A)

As outlined below, the sugar chain-polypeptide complex can be manufactured by e.g. liquid phase synthesis employing Asn having a sugar chain bound thereto.

(1) The carboxy group of an amino acid having the amino group nitrogen protected with a lipophilic protecting group is bound to an amino acid having the amino group free and the carboxy group protected or amidated.
(2) The lipophilic protecting group of the reactant obtained is detached to form a free amino group.
(3) This free amino group and the carboxy group of any amino acid having the amino group nitrogen protected with a lipophilic protecting group are subjected to an amidation reaction in solution. In this case, since the amino group nitrogen of the amino acid on the N-terminal side is protected with a lipophilic protecting group and the carboxy group on the C-terminal side is protected or amidated, self-condensation of amino acids with each other is prevented, the free amino group and the carboxy group react to form a bond.
(4) The above lipophilic protecting group is detached to form a free amino group.
(5) The above steps (3) and (4) are repeated once or more times to yield a peptide of any number of any amino acids linked together, having the C-terminal carboxy group protected or amidated and possessing a free amino group at the N-terminal.
(6) When the free amino group of the peptide synthesized in above (5) is to be protected with an acetyl group, it is also preferred to acetylate with acetic anhydride, acetic acid, and the like.
(7) Finally, the side chain lipophilic protecting group is cleaved with an acid and a peptide having a desired amino acid sequence can be obtained.

Method for Manufacturing a Sugar Chain-Polypeptide Complex—3 (Method A)

As outlined below, the sugar chain-polypeptide complex can be manufactured by e.g. fragment synthesis method employing Asn having a sugar chain bound thereto.

(1) A polypeptide or a sugar chain-polypeptide complex having the amino group nitrogen protected with an acetyl group or a lipophilic protecting group is synthesized on a resin by (1)-(6) of the above method for manufacturing a sugar chain-polypeptide complex (Method A).
(2) The polypeptide or the sugar chain-polypeptide complex is cleaved from the resin under conditions that do not deprotect the side chain protecting group to obtain a polypeptide or the sugar chain-polypeptide complex possessing a free carboxy at the C-terminal and having the amino group nitrogen at N-terminal is protected with an acetyl group or a lipophilic protecting group.
(3) The polypeptide or the sugar chain-polypeptide complex obtained having the amino group nitrogen protected with an acetyl group or a lipophilic protecting group is linked to a resin or a polypeptide by solid or liquid phase synthesis.
(4) The above lipophilic protecting group is detached to form a free amino group.
(5) The above steps (3) and (4) are repeated once or more times to yield a peptide of any number of any amino acids linked together.
(6) Finally, the resin is cleaved with an acid and a peptide having a desired amino acid sequence can be obtained.

Examples of a lipophilic protecting group can include a carbonate- or amide-based protecting group and the like such as a 9-fluorenylmethoxycarbonyl (Fmoc) group, a t-butyloxycarbonyl (Boc) group, a benzyl group, an allyl group, an allyloxycarbonyl group, and an acetyl group. In order to introduce a lipophilic protecting group to an amino acid, for example to introduce an Fmoc group, introduction can be carried out by adding 9-fluorenylmethyl-N-succinimidyl carbonate and sodium hydrogen carbonate and allowing to react. The reaction may be carried out at 0-50° C., preferably at room temperature for about 1-5 hours.

Those commercially available can also be used as the amino acid protected with a lipophilic protecting group, examples of which can include Fmoc-Ser-OH, Fmoc-Asn-OH, Fmoc-Val-OH, Fmoc-Leu-OH, Fmoc-Ile-OH, Fmoc-Ala-OH, Fmoc-Tyr-OH, Fmoc-Gly-OH, Fmoc-Lys-OH, Fmoc-Arg-OH, Fmoc-His-OH, Fmoc-Asp-OH, Fmoc-Glu-OH, Fmoc-Gln-OH, Fmoc-Thr-OH, Fmoc-Cys-OH, Fmoc-Met-OH, Fmoc-Phe-OH, Fmoc-Trp-OH, and Fmoc-Pro-OH.

Moreover, examples of the amino acid protected with a lipophilic protecting group having a protecting group introduced into the side chain can include Fmoc-Arg(Pbf)-OH, Fmoc-Asn(Trt)-OH, Fmoc-Asp(OtBu)-OH, Fmoc-Cys (Acm)-OH, Fmoc-Cys(StBu)-OH, Fmoc-Cys(tBu)-OH, Fmoc-Cys(Trt)-OH, Fmoc-Glu(OtBu)-OH, Fmoc-Gln(Trt)-OH, Fmoc-His(Trt)-OH, Fmoc-Lys(Boc)-OH, Fmoc-Ser (tBu)-OH, Fmoc-Thr(tBu)-OH, Fmoc-Trp(Boc)-OH, and Fmoc-Tyr(tBu)-OH.

Moreover, when it is desired to add a linker in the amino acid sequence of the sugar chain-polypeptide conjugate, a linker can be inserted at a preferred position by using a linker protected with a lipophilic protecting group instead of the above amino acid protected with a lipophilic protecting group in the solid phase synthesis process.

When employing a 2-chlorotrityl chloride resin, esterification can be carried out by employing a base such as diisopropylethylamine (DIPEA), triethylamine, pyridine, and 2,4,6-collidine. Moreover, when employing a resin possessing a hydroxyl group, for example, well-known dehydration condensing agents such as 1-mesitylenesulfonyl-3-nitro-1,2,4-triazole (MSNT), dicyclohexylcarbodiimide (DCC), and diisopropylcarbodiimide (DIC) can be employed as the esterification catalyst. The proportion of use between the amino acid and the dehydration condensing agent is 1 eq. of the former to ordinarily 1-10 eq., preferably 2-5 eq. of the latter.

The esterification reaction is preferably carried out by e.g. placing a resin in a solid phase column, washing this resin with a solvent, and then adding an amino acid solution. Examples of a washing solvent can include dimethylformamide (DMF), 2-propanol, dichloromethane, and the like.

Examples of a solvent for dissolving amino acids can include dimethyl sulfoxide (DMSO), DMF, dichloromethane, and the like. The esterification reaction may be carried out at 0-50° C., preferably at room temperature for about 10 minutes-30 hours, preferably 15 minutes-24 hours.

It is also preferred at this time to cap the unreacted groups on the solid phase by acetylation with acetic anhydride etc.

The detachment of the lipophilic protecting group can be carried out by e.g. treatment with a base. Examples of a base can include piperidine, morpholine, and the like. It is preferred to do so in the presence of a solvent. Examples of a solvent can include DMSO, DMF, methanol, and the like.

The amidation reaction between the free amino group and the carboxy group of any amino acid having the amino group nitrogen protected with a lipophilic protecting group is preferably carried out in the presence of an activator and a solvent.

Examples of an activator can include dicyclohexylcarbodiimide (DCC), 1-ethyl-3-(3-dimethylaminopropyl)carbodiimide hydrochloride salt (WSC/HCl), diphenylphosphorylazide (DPPA), carbonyldiimidazole (CDI), diethylcyanophosphonate (DEPC), benzotriazol-1-yloxytrispyrrolidinophosphonium (DIPCI), benzotriazol-1-yloxytrispyrrolidinophosphonium hexafluorophosphate (PyBOP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazol-1-yl)-1,1,3,3-tetramethyluronium hexafluorophosphate (HBTU), 1-[bis(dimethylamino)methylene]-5-chloro-1H-benzotriazolium 3-oxide hexafluorophosphate (HCTU), O-(7-azabenzotriazol-1-yl)-1,1,3,3-tetramethyluronium hexafluorophosphonate (HATU), O-benzotriazol-1-yl-1,1,3,3-tetramethyluronium tetrafluoroborate (TBTU), 3,4-dihydro-3-hydrodi-4-oxa-1,2,3-benzotriazine (Dhbt), 4-(4,6-dimethoxy-1,3,5-triazin-2-yl)-4-methylmorpholinium chloride n-hydrate (DMT-MM), and the like.

It is preferred that the amount of the activator used is 1-20 equivalents, preferably 1-10 equivalents, and further preferably 1-5 equivalents to the any amino acid having the amino group nitrogen protected with a lipophilic protecting group.

Examples of a solvent can include DMSO, DMF, dichloromethane, and the like. The reaction may be carried out at 0-50° C., preferably at room temperature for about 10 minutes-30 hours, preferably for 15 minutes-24 hours. The detachment of the lipophilic protecting group can be carried out similarly to the above.

When introducing a C-terminal amino acid to Rink-Amide-resin functionalized with an amino group (from Merck & Co., Inc.), Rink-Amide-PEGA resin (from Merck & Co., Inc.), NH-SAL-resin (from Watanabe Chemical Industries, Ltd.), or Amino-PEGA-resin bound to NH-SAL-resin-linker (from Merck & Co., Inc.) and the like, introduction can be carried out by employing the above amidation reaction.

Treatment with an acid is preferred for cleaving the peptide chain from the resin. Examples of an acid can include trifluoroacetic acid (TFA), hydrogen fluoride (HF), and the like.

In this way, a sugar chain-polypeptide complex possessing a glycosylated Asn at the desired position can be obtained.

In one embodiment of the present invention, when the non-reducing terminal on the sugar chain in the glycosylated Asn employed for solid phase synthesis comprises a sialic acid, it is preferred that the carboxy group of said sialic acid is protected by a protecting group in order to prevent the sialic acid from being cleaved by acid treatment. Examples of a protecting group can include a benzyl group, an allyl group, a diphenylmethyl group, a phenacyl group, and the like. The method for introducing the protecting group and detaching the protecting group can be carried out by a well-known method.

Method for Manufacturing a Sugar Chain-Polypeptide Complex (Method B)

The sugar chain-polypeptide complex can also be manufactured by a method of first synthesizing a polypeptide, and then later glycosylating the synthesized polypeptide. Specifically, a polypeptide comprising Cys at the position to be glycosylated is manufactured by solid or liquid phase synthesis method, a method of synthesizing by cells, a method of separating and extracting those that occur in nature, and the like. When the polypeptide is synthesized by a solid or liquid phase synthesis method, amino acids may be linked one residue at a time, or a polypeptide may be linked. Cys that is not to be glycosylated such as Cys at the position predetermined to form a disulfide bond is protected here with e.g. an acetoamidomethyl (Acm) group. Moreover, when introducing Cys that is not to be glycosylated and not used for forming a disulfide bond into the sugar chain-polypeptide complex, it can be introduced by protecting the Cys with a protecting group during the glycosylation step and the disulfide bond formation step, and then deprotecting it. Examples of such a protecting group can include tert-butyl (tBu) or 4-methoxybenzyl and the like.

Moreover, when adding different sugar chains to Cys in one polypeptide, different sugar chains can be introduced by rendering the Cys for introducing a sugar chain first unprotected, and protecting the Cys for introducing the different sugar chain next by StBu and the like. Specifically, when synthesizing the polypeptide by solid phase synthesis etc., the Cys for introducing a first sugar chain is rendered unprotected, and the Cys for introducing a second sugar chain is rendered to be Cys possessing a protecting group with Fmoc-Cys(StBu)-OH etc. Then, a sugar chain is introduced into the unprotected Cys while the protecting group such as StBu is still retained. A different sugar chain can then be introduced into the Cys rendered unprotected by deprotecting the StBu group etc. The Cys for introducing the first sugar chain and the Cys for introducing the second sugar chain can be one or more.

The deprotection of the StBu group can be carried out by subjecting to a reaction with a reductant such as tris(2-carboxyethyl)phosphine hydrochloride salt (TCEP), dithiothreitol (DTT), and tributylphosphine. The above reaction may be carried out ordinarily at 0-80° C., preferably at 5-60° C., and further preferably at 10-35° C. Preferably, the reaction time is ordinarily about 30 minutes-5 hours. Upon completion of the reaction, this may be purified with a well-known method (such as high performance liquid column chromatography (HPLC)) as appropriate.

When introducing different sugar chains, it is preferred to start the introduction with a sugar chain that is more stable against the reduction condition in the deprotection step of Cys or the acidic condition in the purification step such as HPLC. In particular, when introducing a sialic acid-containing sugar chain, it is preferred that a sugar chain that does not possess a sialic acid or a sugar chain with less sialic acid residues is introduced first.

Moreover, when it is desired to add a linker in the amino acid sequence of the sugar chain-polypeptide complex, a linker can be inserted at a preferred position of the synthesized polypeptide by e.g. using a linker protected with a lipophilic protecting group instead of the amino acid protected with a lipophilic protecting group in the solid phase synthesis process.

Next, by reacting a haloacetylated sugar chain derivative with the peptide comprising an unprotected Cys obtained above, the sugar chain is reacted with the thiol group of the unprotected Cys and bound to the peptide. The above reaction may be carried out in a phosphate buffer, a tris-hydrochloride buffer, a citrate buffer, or a mixed solution thereof, ordinarily at 0-80° C., preferably at 10-60° C., and further preferably at 15-35° C. Preferably, the reaction time is ordinarily 10 minutes-24 hours, and preferably, ordinarily approximately 30 minutes-5 hours. Upon completion of the reaction, this may be purified with a well-known method (such as HPLC) as appropriate.

An example of a haloacetylated sugar chain derivative is a compound having the hydroxyl group bound to the carbon at position 1 of an asparagine-linked sugar chain substituted with —NH—$(CH_2)_a$—(CO)—$CH_2X$ (wherein X is a halogen atom, and a is integer and is not limited as long as it does not inhibit the linker function of interest, preferably an integer 0-4).

Specifically, the haloacetylated complex sugar chain derivative and the Cys-containing polypeptide are reacted in a phosphate buffer at room temperature. Upon completion of the reaction, the sugar chain-polypeptide complex possessing a Cys having a sugar chain bound thereto can be obtained by purification with HPLC.

The reaction can also be carried out in a mixed solution of an organic solvent such as DMSO, DMF, methanol, and acetonitrile with the above buffer. In this case, the organic solvent can be added to the above buffer at a ratio in the range of 0-99% (v/v). This is preferred for a peptide comprising unprotected Cys with low solubility against the buffer because the addition of such an organic solvent can improve the solubility against the reaction solution.

The reaction can also be carried out in an organic solvent such as DMSO, DMF, methanol, and acetonitrile or a mixed solution thereof. It is preferred to do so in the presence of a base. Examples of a base can include DIPEA, triethylamine, pyridine, 2,4,6-collidine, and the like. The reaction can also be carried out in a mixed solution of guanidine hydrochloride or urea added to the buffer solution. Guanidine hydrochloride or urea can be added to the above buffer so that the final concentration will be 1 M-8 M. This is preferred because the addition of guanidine hydrochloride or urea can also improve the solubility of a peptide with low solubility against the buffer.

Further, the reaction can also be carried out with addition of tris(2-carboxyethyl)phosphine hydrochloride salt (TCEP) or dithiothreitol (DTT) to the buffer in order to prevent the formation of a dimer of polypeptides comprising unprotected Cys via a disulfide bond. TCEP or DTT can be added to the buffer so that the final concentration will be 10 μM-10 mM.

Moreover, after the sugar chain is bound to the target Cys, the protecting group of Cys protected with Acm and the like is deprotected. When the protecting group is an Acm group, deprotection can be carried out by allowing reaction with iodine, mercury acetate (II), silver nitrate (I), or silver acetate (I) and the like in water, methanol, acetic acid, or a mixed solution thereof.

The above reaction may be carried out ordinarily at 0-80° C., preferably at 5-60° C., and further preferably at 10-35° C. Preferably, the reaction time is ordinarily approximately 5 minutes-24 hours. Upon completion of the reaction, this may be purified with a well-known method (such as HPLC) as appropriate after treatment with DTT or hydrochloric acid and the like.

In this way, a sugar chain-polypeptide complex possessing Cys having a sugar chain bound thereto at the desired position can be obtained. Moreover, as described below, the sugar chain-polypeptide complex purified as such can form a disulfide bond between deprotection Cys.

Moreover, when manufacturing a sugar chain-polypeptide complex possessing multiple sialic acid-containing sugar chains such as disialo or monosialo sugar chains in the peptide sequence, a sialic acid-containing sugar chain having the carboxy group of the sialic acid on the sugar chain to be introduced protected with a benzyl (Bn) group, an allyl group, a diphenylmethyl group, a phenacyl group, and the like can be employed.

When a sugar chain having the carboxy group of the sialic acid protection is introduced, a step of deprotecting the sialic acid protecting group can be carried out after a step of forming a disulfide bond in the sugar chain-polypeptide complex described below.

In this way, by protecting the carboxy group of the sialic acid with a benzyl group and the like, separation/purification step by HPLC etc. in the manufacturing step will be facilitated. The protection of the carboxy group of the sialic acid will also enable prevention of detachment of the acid-labile sialic acid.

The protection reaction of the carboxy group of the sialic acid on the sugar chain can be carried out by a method well-known to those skilled in the art. Moreover, in the sugar chain-polypeptide complex that has formed a disulfide bond, the protecting group of the carboxy group of the sialic acid can be deprotected by hydrolysis under basic conditions. The above reaction may be carried out ordinarily at 0-50° C., preferably at 0-40° C., and further preferably at 0-30° C. Preferably, the reaction time is ordinarily approximately 5 minutes-5 hours. Upon completion of the reaction, this may be purified with a well-known method (such as HPLC) as appropriate after neutralization with a weak acid such as phosphoric acid or acetic acid.

Moreover, the sugar chain-polypeptide complex created by the above Methods A and B can form a disulfide bond between Cys with a method well-known to those skilled in the art employing air and/or oxygen, iodine, DMSO, a mixture of oxidized and reduced glutathione, potassium ferricyanide, Ellman's reagent (5,5'-dithiobis(2-nitrobenzoic acid)), thallium trifluoroacetate (III), alkyltrichlorosilane sulfoxide, and the like.

When forming a disulfide bond between Cys-Cys, Cys in the sugar chain-polypeptide complex that is not desired to form a disulfide bond is protected by a protecting group. A protecting group that is stable under oxidizing condition such as Acm, tBu, 4-methoxybenzyl, and 4-methylbenzyl can be employed as such a protecting group.

In Method B, the formation of a disulfide bond can also be carried out before the introduction of the sugar chain. However, when a protecting group is introduced in the Cys that is desired to form a disulfide bond, the deprotection step will precede the disulfide bond formation step.

Moreover, in Method B, the amino acid to be reacted with the haloacetylated complex sugar chain derivative is not particularly limited as long as it is a thiol group-containing amino acid, and for example, D-cysteine (D-Cys), homocysteine, norcysteine, penicillamine, and the like can also be employed similarly to Cys.

The type of sugar chain bound to the sugar chain-polypeptide complex according to the present invention is not particularly limited, but it is preferred that the total number of sugar residues present in the sugar chain bound to the sugar chain-polypeptide complex is 5 or more. For example, one or more sugar chains that is a pentasaccharide or higher may be added, or multiple sugar chains that is a pentasaccharide or lower may be added so that the number of sugar residues that is present on the sugar chain added to one sugar chain-polypeptide complex is 5 or more. When adding multiple sugar chains, the type of sugar chain bound to one peptide may be identical or different types of sugar chains may be bound in combination, but it is preferably identical.

For example, when the total number of sugar residues present in the sugar chain bound to the sugar chain-polypeptide complex is 5, one of each of a maltose sugar chain possessing two sugar residues and a maltotriose sugar chain possessing a three sugar residues may be bound. Moreover, when the total number of sugar residues present in the sugar chain bound to the sugar chain-polypeptide complex is 6, three maltose sugar chains may be bound, or two maltotriose sugar chains may be bound. Moreover, when the total number of sugar residues present in the sugar chain bound to the sugar chain-polypeptide complex is 7, two maltose sugar chains and one maltotriose sugar chain may be bound, or one diGlcNAc sugar chain possessing seven sugar residues may be bound. Similarly, various combinations of sugar chains may be bound for cases where the total number of sugar residues present in the sugar chain bound to the sugar chain-polypeptide complex is 8 or more.

The number of sugar chains bound to the sugar chain-polypeptide complex according to the present invention is not limited, as long as the sugar chain-polypeptide complex will not lose the characteristic of forming a β sheet structure by self-assembly in an aqueous solution having a pH around neutral. For example, it may be 1, 2, 3, 4, 5, or 6 chains, preferably 1, 2, or 3 chains.

In the sugar chain-polypeptide complex according to the present invention, the position of the amino acid residue that the sugar chain binds to is not limited, as long as the sugar chain-polypeptide complex will not lose the characteristic of forming a β sheet structure by self-assembly in an aqueous solution having a pH around neutral. For example, the position of the amino acid residue that the sugar chain binds to may be the N- and/or C-terminal side of the polypeptide, or it may be a position other than the N- and C-terminal side.

Preferably, a sugar chain may be bound to every amino acid up to position x counting from the amino acid residue positioned at the N-terminal of the polypeptide and every amino acid up to position y counting from the amino acid residue positioned at the C-terminal (wherein x and y are integers, x≥0, y≥0, and x+y is the total number of sugar chains bound to the polypeptide).

More specifically, when the number of sugar chains bound to the polypeptide is 1, said one sugar chain may be bound to the amino acid residue positioned at the N-terminal of said polypeptide or the amino acid residue positioned at the C-terminal.

Moreover, when the number of sugar chains bound to the polypeptide is 2, said two sugar chains may be bound to an amino acid residue selected from the group consisting of (1)-(3) below:
(1) the first and second amino acid residues counting from the amino acid residue positioned at the N-terminal of the polypeptide
(2) the first and second amino acid residues counting from the amino acid residue positioned at the C-terminal of the polypeptide, and
(3) the amino acid residue positioned at the N-terminal of the polypeptide and the amino acid residue positioned at the C-terminal of said polypeptide.

Moreover, when the number of sugar chains bound to the polypeptide is 3, said three sugar chains may be bound to any amino acid residue selected from the group consisting of (1)-(4) below:
(1) the first, second, and third amino acid residues counting from the amino acid residue positioned at the N-terminal of the polypeptide
(2) the first, second, and third amino acid residues counting from the amino acid residue positioned at the C-terminal of the polypeptide
(3) the first and second amino acid residues counting from the amino acid residue positioned at the N-terminal of the polypeptide, and the amino acid residue positioned at the C-terminal of the polypeptide, and
(4) the amino acid residue positioned at the N-terminal of the polypeptide, and the amino acid residues positioned at positions 1 and 2 counting from the C-terminal of the polypeptide.

It is preferred that the sugar chain to be added to the sugar chain-polypeptide complex according to the present invention is branched. Here, the sugar chain bound to the polypeptide is "a sugar chain with a branch" as used herein is not limited to e.g. those possessing a branch in one sugar chain such as with a disialo sugar chain, an asialo sugar chain, or a diGlcNAc sugar chain, but also encompasses e.g. those having multiple linear sugar chains added to one polypeptide to create a state where the sugar chain is branched in the peptide as a whole. For example, those having two or more linear sugar chains such as a maltose sugar chain or a maltotriose sugar chain bound to one peptide are also encompassed in "a sugar chain with a branch" herein.

A hydrogel as used herein means a gel in which the dispersion medium is substantially water. The peptide according to the present invention will form a hydrogel when dispersed in water. The mixture proportion between the peptide and water is not particularly limited, and those skilled in the art can appropriately adjust the mixture proportion according to the application of the hydrogel. For example, when manufacturing a hydrogel with C(DiGlcNAc)-(RADA)4 according to one embodiment of the present invention, a hydrogel is formed in a broad pH when the peptide concentration is 0.5 wt. % or more, and a hydrogel is formed at a neutral pH but may not be formed in an acidic pH when the peptide concentration is about 0.25 wt. %. In this way, the hydrogel manufactured from the peptide according to the present invention can control hydro gel formation by pH when the peptide concentration is low. Utilizing such a nature, it can be promptly disposed or discharged by for example turning a gel into a sol by changing the pH after using the hydrogel.

In the present invention, the method for evaluating the strength or nature of the hydrogel is not particularly limited, and for example can be evaluated by a steel ball loading test or a kinetic viscosity measurement. In the steel ball loading test, for example, the strength of the hydrogel can be evaluated by loading a steel ball of a given weight on the surface of a hydrogel formed inside a Durham's tube and observing whether the steel ball will stay on the surface of the hydrogel or sinks. Moreover, in the steel ball loading test, the transparency in the hydrogel or the presence or absence of an insoluble matter or precipitation can be visually verified. In the kinetic viscosity measurement of the hydrogel, the change in the strength of the hydrogel over time can be measured by measuring the kinetic viscosity of the subject hydrogel with a rheometer.

When evaluating a hydrogel in the present Examples, a vigorous stirring operation is encompassed as one operation for forming a hydrogel. A highly uniform gel can be formed by carrying out such vigorous stirring operation, and a more reliable evaluation can be performed.

The hydrogel according to the present invention can be employed for various applications. For example, since the hydrogel according to the present invention is highly safe on the living organisms, it can be employed for medical applications (a surgery auxiliary agent such as a hemostatic matrix or a blood vessel embolization material, a controlled release carrier such as a pharmaceutical, a wound dressing for e.g. surgery operation or regenerative medicine, a mucosal protrusion material, an alveolar bone reconstruction material, a tissue reconstruction material such as a cornea regeneration material, and a three dimensional culture matrix for e.g. a tissue culture experiment) or cosmetic applications (such as skincare and haircare products). Particularly preferably, it can be employed as a hemostatic matrix, a controlled release carrier, or a culture matrix.

A hemostatic matrix as used herein broadly means a matrix employed to stop bleeding from a living organism. The hemostatic matrix according to the present invention is not limited to those comprising only the sugar chain-polypeptide complex according to the present invention and water, and may comprise other various components. For example, by comprising an agent that has a disinfecting/sterilizing component, it can not only stop the bleeding from a wound, but at the same time sterilize/disinfect the wound.

A controlled release carrier as used herein broadly means a carrier having the nature to gradually release the encapsulated substance or agent. The substance to be encapsulated into the controlled release carrier according to the present invention is not particularly limited, and various substances or agents can be encapsulated. Moreover, the substance or agent to be encapsulated into the controlled release carrier according to the present invention is not limited to one type, and two or more types of substances or agents can be simultaneously encapsulated.

A culture matrix as used herein broadly means a matrix employed for cell or tissue culture. For example, by coating a cell culture dish with the culture matrix according to the present invention and culturing cells, adhesiveness/growth potential of the cells can be improved. Moreover, for example, by encapsulating cells or tissues in the culture matrix according to the present invention and culturing, an efficient three-dimensional culture of cells or tissues can be carried out.

A mucosal protrusion material as used herein broadly means a submembrane injection material for forming a mucosal protrusion of the lesion site in a mucosal resection surgery or a submucosal detachment surgery for e.g. stomach or esophageal cancer by endoscopic surgery. For example, when resecting the lesion site with e.g. an endoscope, the tissue protrusion material according to the present invention is injected below the lesion site to allow protrusion of the resection site in order to facilitate resection of the lesion site.

A blood vessel embolization material as used herein broadly means an intravascular embolization-promoting prosthetic material for use as an embolus in arterial embolization. In arterial embolization for e.g. liver cancer or uterine fibroid, when the blood vessel embolization material according to the present invention is injected into an artery that is upstream of the lesion site, a hydrogel is formed upon contact with blood. This can block the artery which is the nutrient supply route to a tumor, thus killing the tumor.

A tissue reconstruction material as used herein broadly means a material that will be the scaffolding in regenerative medicine when reconstructing a tissue in vivo. For example, in the tissue reconstruction material according to the present invention is injected in bone regeneration, it can become the scaffolding for cells performing osteogenesis, thus promoting bone regeneration.

The terms used herein are to be employed to describe particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

Terms such as first and second are sometimes employed to express various elements, and it should be recognized that these elements are not to be limited by these terms. These terms are employed solely for the purpose of discriminating one element from another, and it is for example possible to describe a first element as a second element, and similarly, to describe a second element as a first element without departing from the scope of the present invention.

The present invention will now be more specifically described by Examples. However, the present invention can be embodied by various embodiments, shall not be construed as being limited to the Examples described herein.

For example, Disialo-BrAc as shown herein indicates a bromoacetylated disialo sugar chain. Moreover, for example, C(Disialo)-(RADA)4 as shown herein indicates that a cysteine residue having a disialo sugar chain bound thereto is bound to the N-terminal of a polypeptide having the amino acid sequence RADARADARADARADA.

EXAMPLES

Synthesis Example 1

Synthesis of Maltoheptaose-BrAc

Synthesis Example 1-1

Amination

Compound 1 represented by the following Formula (11) (product name: maltoheptaose, from Tokyo Chemical Industry Co., Ltd.) (53.2 mg, 46.1 μmol) was dissolved in water (5 mL). Sodium hydrogen carbonate (3.6 g) was added to the solution, heated to 37° C., and then stirred for 19 hours. After water was added, concentration under reduced pressure condition was carried out several times. This was dissolved again in water and lyophilized to obtain a lyophilizate comprising compound 2 represented by the following Formula (12).

[Chemical Formula 12]

Formula (11)

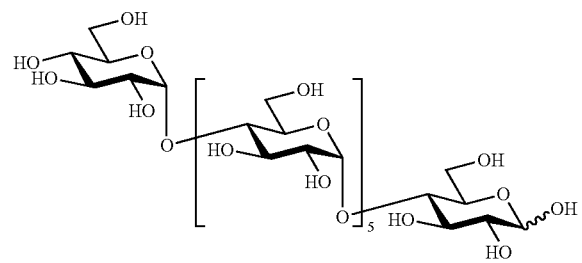

[Chemical Formula 13]

Formula (12)

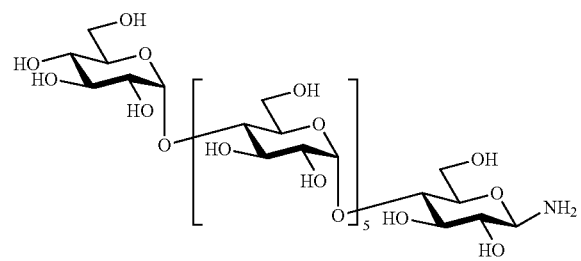

Synthesis Example 1-2

Bromoacetylation

Compound 2 obtained in Synthesis Example 1-1 and sodium carbonate (83.0 mg, 0.92 mmol, 20 eq. to compound 2) were dissolved in water, and cooled to 0° C. Bromoacetyl bromide dissolved in dichloromethane (40.0 μL, 0.46 mmol, 10 eq. to compound 2) was slowly added dropwise, and stirred for 2 hours. This was partitioned with dichloromethane and water, and hydrobromic acid was added to the water phase. Water was partially concentrated under reduced pressure condition.

The reaction solution was purified with HPLC [column: SHISEIDO CAPCELL PAK C18 UG-120 (5 μm), φ 20×250 mm, flow rate: 7.0 mL/min, developing solvent A: water, B: acetonitrile, gradient A:B=99.5:0.5->90:10, 15 min. linear concentration gradient elution] to obtain Maltoheptaose-BrAc represented by the following Formula (13) (26.7 mg, 20.9 μmol, yield 46%).

[Chemical Formula 14]

Formula (13)

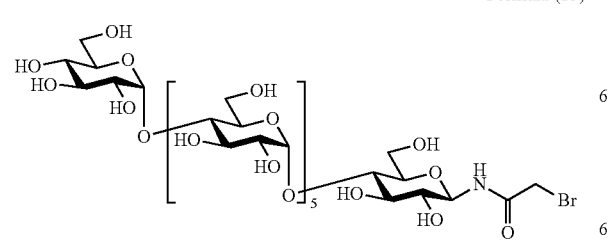

Synthesis Example 2

Synthesis of Maltose-BrAc

Synthesis was carried out with a method similar to Synthesis Example 1 except that compound 3 represented by the following Formula (14) (product name: maltose, from Tokyo Chemical Industry Co., Ltd.) (200 mg, 0.58 mmol) was employed instead of compound 1 to obtain Maltose-BrAc represented by the following Formula (15) (179.1 mg, yield 67%).

[Chemical Formula 15]

Formula (14)

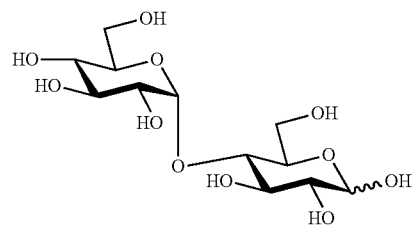

[Chemical Formula 16]

Formula (15)

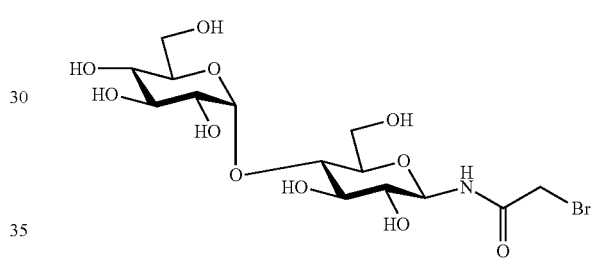

Synthesis Example 3

Synthesis of Maltotriose-BrAc

Synthesis was carried out with a method similar to Synthesis Example 1 except that compound 4 represented by the following Formula (16) (product name: maltotriose, from Tokyo Chemical Industry Co., Ltd.) (100 mg, 198.6 μmol) was employed instead of compound 1 to obtain Maltotriose-BrAc represented by the following Formula (17) (58.2 mg, yield 47%).

[Chemical Formula 17]

Formula (16)

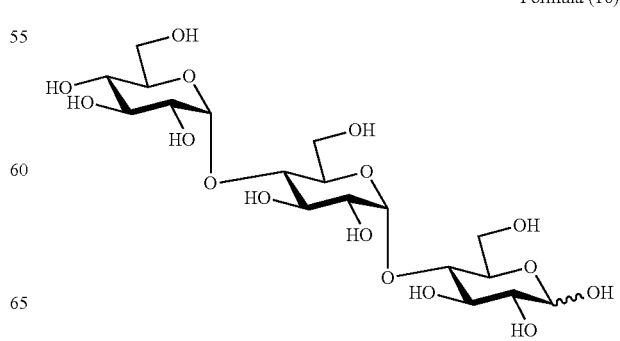

-continued

[Chemical Formula 18]

Formula (17)

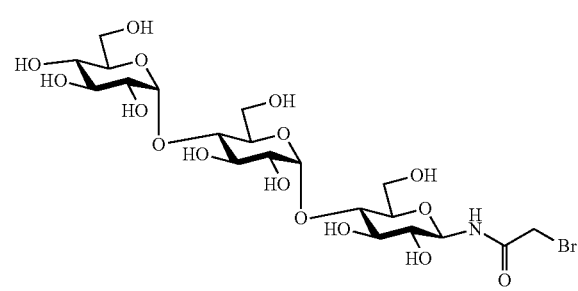

Synthesis Example 4

Synthesis of Maltotetraose-BrAc

Synthesis was carried out with a method similar to Synthesis Example 1 except that compound 5 represented by the following Formula (18) (product name: maltotetraose, from Tokyo Chemical Industry Co., Ltd.) (200 mg, 0.2 mmol) was employed instead of compound 1 to obtain Maltotetraose-BrAc represented by the following Formula (19) (133.1 mg, yield 51%).

[Chemical Formula 19]

Formula (18)

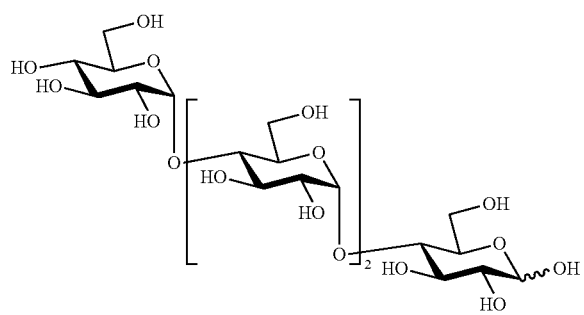

[Chemical Formula 20]

Formula (19)

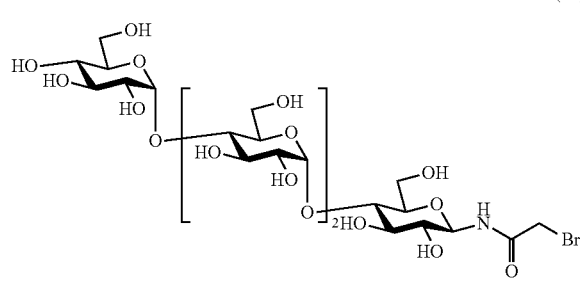

Synthesis Example 5

Synthesis of β-Cyclodextrin-BrAc

Synthesis was carried out with a method similar to Synthesis Example 1-2 except that compound 6 represented by the following Formula (20) (product name: 3A-amino-3A-deoxy-(2AS,3AS)-β-cyclodextrin hydrate, from Tokyo Chemical Industry Co., Ltd.) (101.5 mg, 89.5 μmol) was employed instead of compound 1 to obtain β-cyclodextrin-BrAc represented by the following Formula (21) (31.2 mg, yield 28%).

[Chemical Formula 21]

Formula (20)

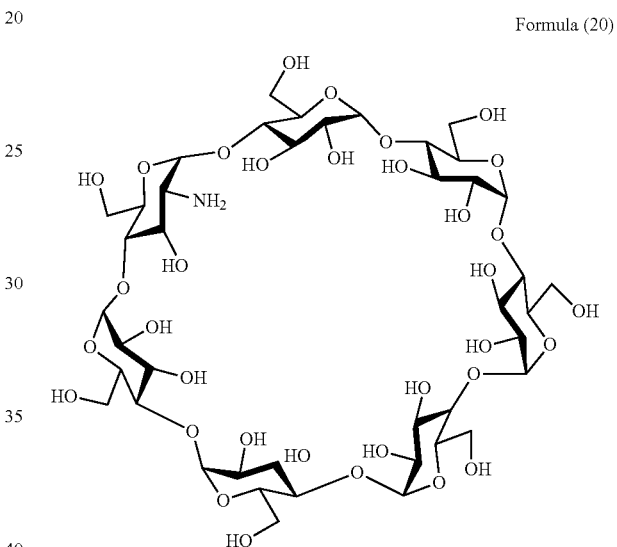

[Chemical Formula 22]

Formula (21)

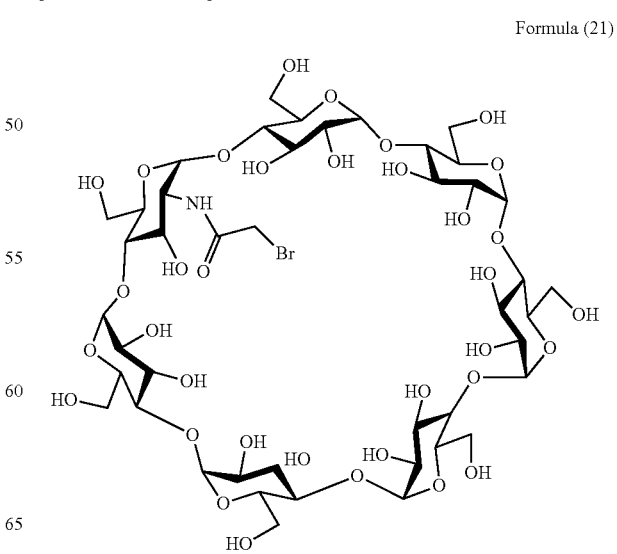

Synthesis Example 6

Synthesis of γ-Cyclodextrin-BrAc

Synthesis was carried out with a method similar to Synthesis Example 1-2 except that compound 7 represented by the following Formula (22) (product name: 3A-amino-3A-deoxy-(2AS,3AS)-γ-cyclodextrin hydrate, from Tokyo Chemical Industry Co., Ltd.) (100.0 mg, 77.1 μmol) was employed instead of compound 1 to obtain γ-cyclodextrin-BrAc represented by the following Formula (23) (41.1 mg, yield 38%).

[Chemical Formula 23]

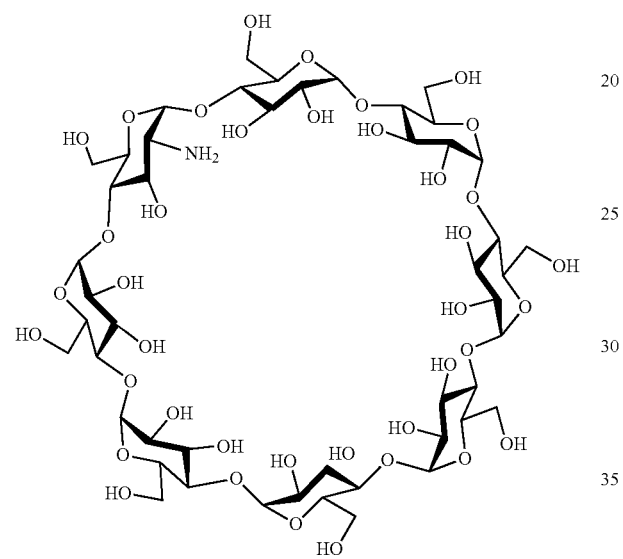

Formula (22)

[Chemical Formula 24]

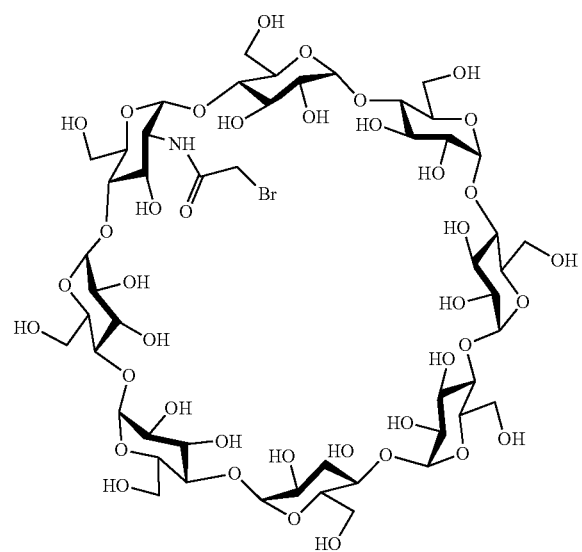

Formula (23)

Synthesis Example 7

Synthesis of Disialo-BrAc

Synthesis was carried out with a method similar to that described in WO2005/010053 to obtain Disialo-BrAc represented by the following Formula (25).

[Chemical Formula 25]

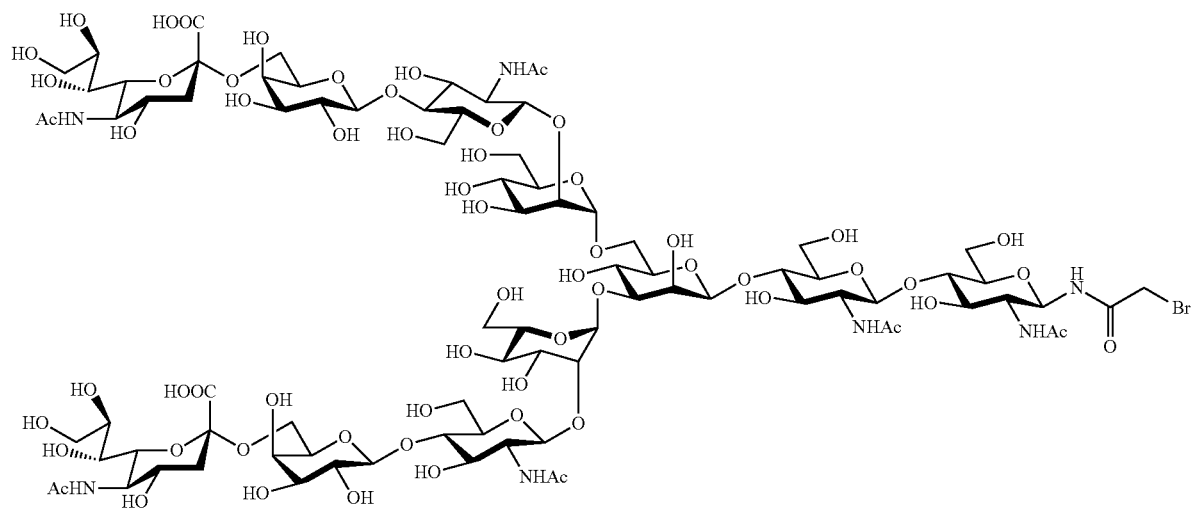

Formula (25)

Synthesis Example 8

Synthesis of Asialo-BrAc

Synthesis was carried out with a method similar to that described in WO2005/010053 to obtain Asialo-BrAc represented by the following Formula (27).

[Chemical Formula 26]

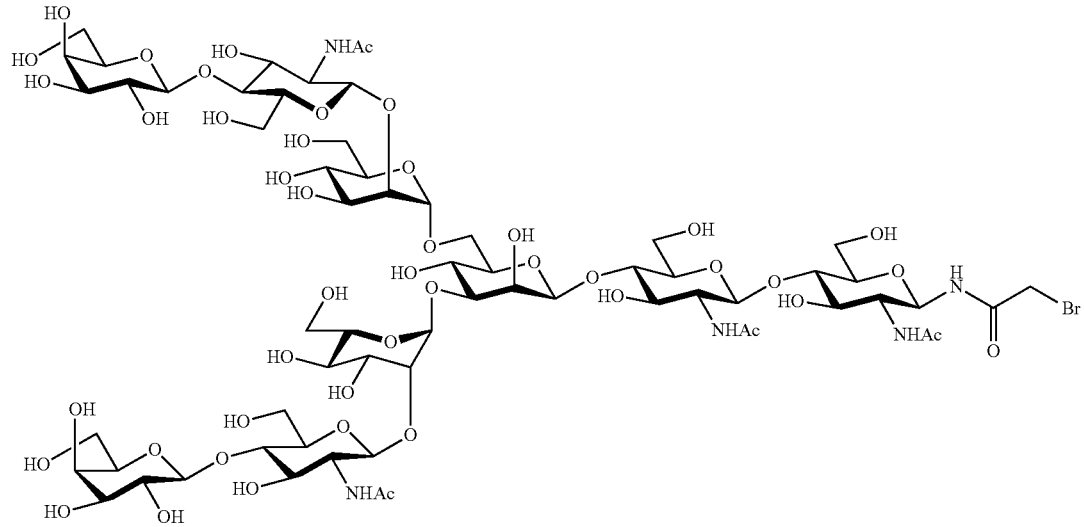

Formula (27)

Synthesis Example 9

Synthesis of DiGlcNAc-BrAc

Synthesis was carried out with a method similar to that described in WO2005/010053 to obtain DiGlcNAc-BrAc represented by the following Formula (29).

[Chemical Formula 27]

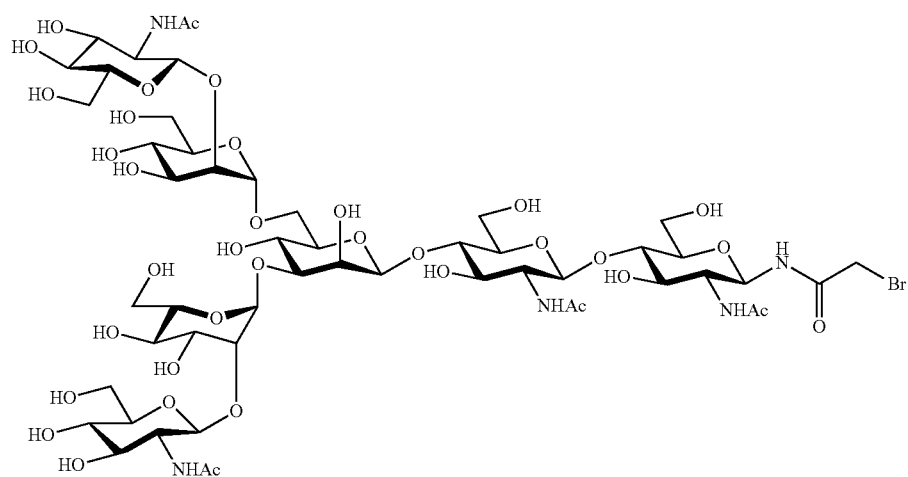

Formula (29)

Synthesis Example 10

Synthesis of DiMan-BrAc

Synthesis was carried out with a method similar to that described in WO2005/010053 to obtain DiMan-BrAc represented by the following Formula (31).

[Chemical Formula 28]

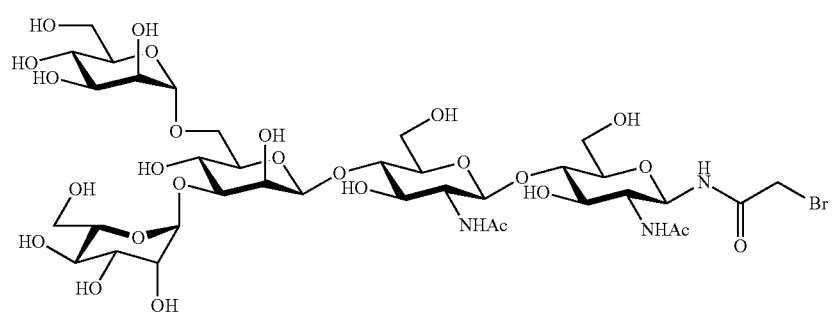

Formula (31)

Synthesis Example 11

Synthesis of GlcNAc-BrAc

Synthesis was carried out with a method similar to that described in WO2005/010053 to obtain GlcNAc-BrAc represented by the following Formula (33).

[Chemical Formula 29]

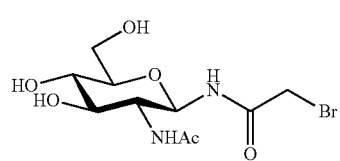

Formula (33)

Synthesis Example 12

Synthesis of DiBn-Disialo-BrAc

To Disialo-BrAc (28.9 mg, 12.3 μmol), DMF (0.58 mL), lithium bromide (21.5 mg, 248 μmol), and benzyl bromide (14.6 μL, 122 μmol) were sequentially added, and reacted at 30° C. for 20 hours. Benzyl bromide (14.6 μL, 122 μmol) was further added and reacted for 20 hours. To the reaction solution was added toluene (30 mL), separated by centrifugation (10,000×g, 10 minutes), and then the precipitate was dissolved in water (100 μL) and purified with HPLC [column: SHISEIDO CAPCELL PAK C18 UG-120 (5 μm), φ 20×250 mm, flow rate: 8.0 mL/min, developing solvent: water:acetonitrile=95:5->70:30, 20 min. linear concentration gradient elution] to obtain DiBn-Disialo-BrAc represented by the following Formula (35) (7.6 mg, yield 24%).

Formula (35)

[Chemical Formula 30]

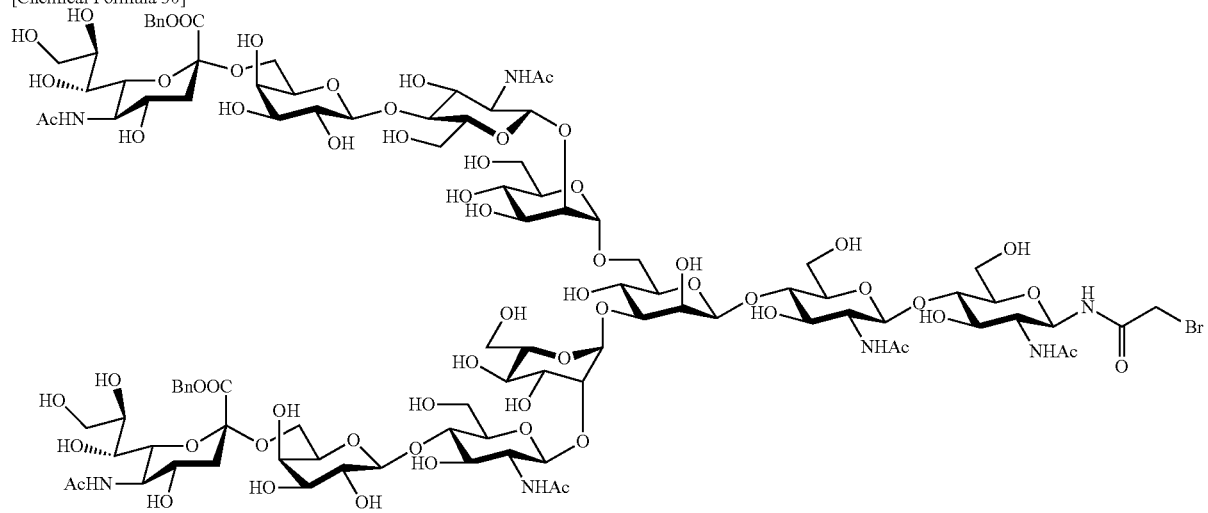

MALDI-MS: (m/z) calcd for $C_{100}H_{152}BrN_7O_{62}$: [M+Na]+ 2544.8, found: 2544.4.

Synthesis Example 13

Synthesis of C(Disialo)-(RADA)4

Synthesis Example 13-1

Synthesis of Ac—C(RADA)4-NH$_2$

Rink amide PEGA resin (100 µmol) was taken up in a column for solid phase synthesis, washed with DMF and dichloromethane, followed by addition of a solution of Fmoc-Ala-OH (124.5 mg, 400 µmol), 1-bisdimethylaminomethylene-5-chloro-1H-benzotriazolium 3-oxide hexafluorophosphate (HCTU) (157.2 mg, 380 µmol), and diisopropylethylamine (DIPEA) (104.5 µL, 600 µmol) in DMF (2.5 mL), and this was shaken for 15 minutes. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (36) (SEQ ID NO. 4) was synthesized with a Prelude™ peptide synthesizer. The condensation reaction was carried out in DMF using HCTU as the condensing agent.

[Chemical Formula 31]

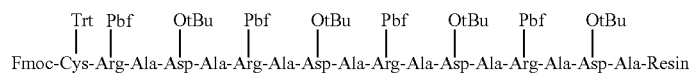

Formula (36)

The Fmoc protecting group was removed by treatment with 20% piperidine in DMF. After washing with DMF and dichloromethane, acetic anhydride and pyridine were added and shaken for 1 hour. After washing with DMF and dichloromethane, trifluoroacetic acid (TFA):water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=88:12->78:22%, 11 min. linear concentration gradient elution] to obtain a polypeptide represented by the following Formula (37) (SEQ ID NO. 5) (32.7 mg).

[Chemical Formula 32]

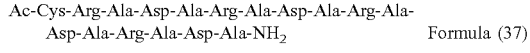

Formula (37)

Synthesis Example 13-2

Glycosylation Reaction of Thiol

The polypeptide obtained with the method described in Synthesis Example 13-1 (SEQ ID NO. 5) (20.5 mg, 11.2 µmol) and Disialo-BrAc synthesized in Synthesis Example 7 (66.0 mg, 28.0 µmol, 2.5 eq. to peptide 1) were dissolved in 0.2 M phosphate buffer (pH 7.3, 3.7 mL) comprising 33 µM of TCEP and 8 M guanidine hydrochloride, and reacted at room temperature for 4 hours.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (38) (SEQ ID NO. 6) (23.8 mg, 5.83 µmol, yield 52%).

[Chemical Formula 33]

Formula (38)

ESI-MS: (m/z) calcd for $C_{121}H_{203}N_{35}O_{62}S$: [M+2H]$^{2+}$ 2040.5, [M+3H]$^{3+}$ 1360.7, [M+4H]$^{4+}$ 1020.7, found: 2040.4, 1360.6, 1020.7.

Synthesis Example 14

Synthesis of C(Asialo)-(RADA)4

The polypeptide synthesized in Synthesis Example 13-1 (SEQ ID NO. 5) (22.7 mg, 12.5 µmol) and Asialo-BrAc synthesized in Synthesis Example 8 (55.0 mg, 31.2 µmol, 2.5 eq. to peptide 1) were dissolved in 0.2 M phosphate buffer (pH 7.3, 4.7 mL) comprising 33 µM of TCEP and 8 M guanidine hydrochloride, and reacted at room temperature for 3 hours.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=90:10->75:25, 18 min. linear concentration gradient elution] to obtain a sugar chain-polypeptide complex represented by the following Formula (39) (SEQ ID NO. 7) (20.5 mg, 5.86 µmol, yield 47%).

[Chemical Formula 34]

Formula (39)

Asialo
|
Ac-Cys-Arg-Ala-Asp-Ala-Arg-Ala-Asp-Ala-Arg-Ala-Asp-Ala-Arg-Ala-Asp-Ala-NH$_2$ ESI-MS: (m/z) calcd for $C_{133}H_{223}N_{35}O_{72}S$: $[M+2H]^{2+}$ 1749.2, $[M+3H]^{3+}$ 1166.5, $[M+4H]^{4+}$ 875.1, found: 1749.3, 1166.2, 874.9.

Synthesis Example 15

Synthesis of C(DiGlcNAc)-(RADA)4

The polypeptide synthesized in Synthesis Example 13-1 (SEQ ID NO. 5) (25.3 mg, 13.9 µmol) and DiGlcNAc-BrAc synthesized in Synthesis Example 9 (30.0 mg, 20.9 µmol, 1.5 eq. to peptide 1) were dissolved in 0.2 M phosphate buffer (pH 7.3, 4.7 mL) comprising 33 µM of TCEP and 8 M guanidine hydrochloride, and reacted at room temperature for 3 hours.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=88:12->81:19, 10 min. linear concentration gradient elution] to obtain a sugar chain-polypeptide complex represented by the following Formula (40) (SEQ ID NO. 8) (23.9 mg, 7.53 µmol, yield 54%).

[Chemical Formula 35]

Formula (40)

DiGlcNAc
|
Ac-Cys-Arg-Ala-Asp-Ala-Arg-Ala-Asp-Ala-Arg-Ala-Asp-Ala-Arg-Ala-Asp-Ala-NH$_2$

ESI-MS: (m/z) calcd for $C_{121}H_{203}N_{35}O_{62}S$: $[M+2H]^{2+}$ 1587.1, $[M+3H]^{3+}$ 1058.4, $[M+4H]^{4+}$ 794.0, found: 1586.7, 1058.1, 793.8.

Synthesis Example 16

Synthesis of C(DiMan)-(RADA)4

The polypeptide synthesized in Synthesis Example 13-1 (SEQ ID NO. 5) (15.2 mg, 8.37 µmol) and DiMan-BrAc synthesized in Synthesis Example 10 (21.5 mg, 20.9 µmol, 2.5 eq. to peptide 1) were dissolved in 0.2 M phosphate buffer (pH 7.2, 3.1 mL) comprising 33 µM of TCEP and 8 M guanidine hydrochloride, and reacted at room temperature for 2 hours.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (41) (SEQ ID NO. 9) (16.9 mg, 6.11 µmol, yield 73%).

[Chemical Formula 36]

Formula (41)

ESI-MS: (m/z) calcd for $C_{121}H_{203}N_{35}O_{62}S$: $[M+2H]^{2+}$ 1383.9, $[M+3H]^{3+}$ 922.9, $[M+4H]^{4+}$ 629.5, found: 1383.6, 922.7, 692.3.

Synthesis Example 17

Synthesis of C(GlcNAc)-(RADA)4

The polypeptide synthesized in Synthesis Example 13-1 (SEQ ID NO. 5) (14.9 mg, 8.21 µmol) and GlcNAc-BrAc synthesized in Synthesis Example 11 (5.6 mg, 16.4 µmol, 2.0 eq. to peptide 1) were dissolved in 0.2 M phosphate buffer (pH 7.3, 3.1 mL) comprising 33 µM of TCEP and 8 M guanidine hydrochloride, and reacted at room temperature for 2 hours.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=95:5->5:95, 15 min. linear concentration gradient elution] to obtain a sugar chain-polypeptide complex represented by the following Formula (42) (SEQ ID NO. 10) (15.4 mg, 7.42 yield 90%).

[Chemical Formula 37]

Formula (42)

ESI-MS: (m/z) calcd for $C_{79}H_{134}N_{32}O_{32}S$: $[M+2H]^{2+}$ 1039.1, $[M+3H]^{3+}$ 693.1, $[M+4H]^{4+}$ 520.0, found: 1039.0, 692.6, 520.0.

Synthesis Example 18

Synthesis of C(Maltoheptaose)-(RADA)4

The polypeptide synthesized in Synthesis Example 13-1 (SEQ ID NO. 5) (9.3 mg, 5.12 µmol) and Maltoheptaose-BrAc synthesized in Synthesis Example 1 (9.8 mg, 7.68 µmol, 1.5 eq. to peptide 1) were dissolved in 0.2 M phosphate buffer (pH 7.3, 3.1 mL) comprising 33 µM of TCEP and 8 M guanidine hydrochloride, and reacted at room temperature for 4 hours.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=88:12->72:28, 16 min. linear concentration gradient elution] to obtain a sugar chain-polypeptide complex represented by the following Formula (43) (SEQ ID NO. 11) (5.1 mg, 1.70 µmol, yield 33%).

[Chemical Formula 38]

Formula (43)

ESI-MS: (m/z) calcd for $C_{113}H_{191}N_{31}O_{62}S$: $[M+2H]^{2+}$ 1505.0, $[M+3H]^{3+}$ 1003.7, found: 1504.6, 1003.4.

Synthesis Example 19

Synthesis of C(β-Cyclodextrin)-(RADA)4

The polypeptide synthesized in Synthesis Example 13-1 (SEQ ID NO. 5) (17.7 mg, 9.75 mol) and β-cyclodextrin-BrAc synthesized in Synthesis Example 5 (36.7 mg, 29.2 μmol, 3.0 eq. to peptide 1) were dissolved in 0.2 M phosphate buffer (pH 7.3, 3.3 mL) comprising 33 μM of TCEP and 8 M guanidine hydrochloride, and reacted at room temperature for 24 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=88:12->72:28, 16 min. linear concentration gradient elution] to obtain a sugar chain-polypeptide complex represented by the following Formula (44) (SEQ ID NO. 12) (6.8 mg, 2.27 μmol, yield 23%).

[Chemical Formula 39]

Formula (44)

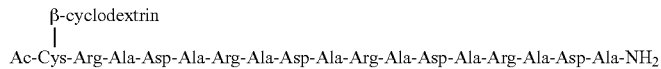

ESI-MS: (m/z) calcd for $C_{113}H_{189}N_{31}O_{61}S$: $[M+2H]^{2+}$ 1496.0, $[M+3H]^{3+}$ 997.7, $[M+4H]^{4+}$ 748.5, found: 1495.6, 997.7, 748.3.

Synthesis Example 20

Synthesis of C(γ-Cyclodextrin)-(RADA)4

The polypeptide synthesized in Synthesis Example 13-1 (SEQ ID NO. 5) (16.0 mg, 8.81 μmol) and γ-cyclodextrin-BrAc synthesized in Synthesis Example 6 (36.7 mg, 25.9 μmol, 3.0 eq. to peptide 1) were dissolved in 0.2 M phosphate buffer (pH 7.3, 3.0 mL) comprising 33 μM of TCEP and 8 M guanidine hydrochloride, and reacted at room temperature for 5 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->5:95, 15 min. linear concentration gradient elution] to obtain a sugar chain-polypeptide complex represented by the following Formula (45) (SEQ ID NO. 13) (6.0 mg, 1.90 μmol, yield 22%).

[Chemical Formula 40]

ESI-MS: (m/z) calcd for $C_{119}H_{199}N_{31}O_{66}S$: $[M+2H]^{2+}$ 1577.1, $[M+3H]^{3+}$ 1051.7, $[M+4H]^{4+}$ 789.0, found: 1576.7, 1051.4, 788.8.

Synthesis Example 21

Synthesis of C(Disialo)-(RADA)5

Synthesis Example 21-1

Synthesis of Ac—C(RADA)5-NH$_2$

Rink amide PEGA resin (100 μmol) was taken up in a column for solid phase synthesis, washed with DMF and dichloromethane, followed by addition of a solution of Fmoc-Ala-OH (124.5 mg, 400 μmol), HCTU (157.2 mg, 380 μmol), and DIPEA (104.5 μL, 600 μmol) in DMF (2.5 mL), and this was shaken for 15 minutes. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (46) (SEQ ID NO. 14) was synthesized with a Prelude™ peptide synthesizer. The condensation reaction was carried out in DMF using HCTU as the condensing agent.

[Chemical Formula 42]

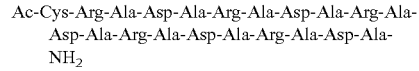

Formula (47)

Synthesis Example 21-2

Glycosylation Reaction of Thiol

The polypeptide synthesized in Synthesis Example 21-1 (SEQ ID NO. 15) (13.9 mg, 6.24 μmol) and Disialo-BrAc synthesized in Synthesis Example 7 (36.5 mg, 15.6 μmol, 2.5 eq. to peptide 1) were dissolved in 0.2 M phosphate buffer (pH 7.3, 2.1 mL) comprising 33 μM of TCEP and 8 M guanidine hydrochloride, and reacted at room temperature for 3 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (48) (SEQ ID NO. 16) (7.8 mg, 1.74 μmol, yield 28%).

[Chemical Formula 41]

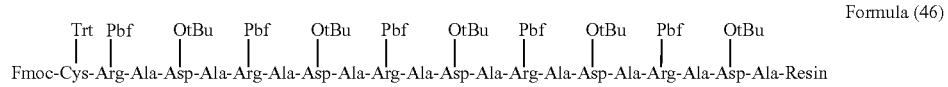

Formula (46)

The Fmoc protecting group was removed by treatment with 20% piperidine in DMF. After washing with DMF and

[Chemical Formula 43]

Formula (48)

dichloromethane, acetic anhydride and pyridine were added and shaken for 1 hour. After washing with DMF and dichloromethane, TFA:water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=88:12->78:22%, 11 min. linear concentration gradient elution] to obtain compound polypeptide represented by the following Formula (47) (SEQ ID NO. 15) (32.7 mg).

ESI-MS: (m/z) calcd for $C_{171}H_{284}N_{44}O_{94}S$: $[M+3H]^{3+}$ 1498.5, $[M+4H]^{4+}$ 1124.1, $[M+5H]^{5+}$ 899.5, found: 1498.6, 1123.9, 899.4.

Synthesis Example 22

Synthesis of C(Asialo)-(RADA)5

The polypeptide synthesized in Synthesis Example 21-1 (SEQ ID NO. 15) (18.8 mg, 8.43 μmol) and Asialo-BrAc synthesized in Synthesis Example 8 (44.5 mg, 25.3 μmol, 3.0 eq. to peptide 1) were dissolved in 0.2 M phosphate buffer (pH 7.2, 2.8 mL) comprising 33 μM of TCEP and 8 M guanidine hydrochloride, and reacted at room temperature for 2 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (49) (SEQ ID NO. 17) (16.0 mg, 4.09 μmol, yield 49%).

[Chemical Formula 44]

Formula (49)

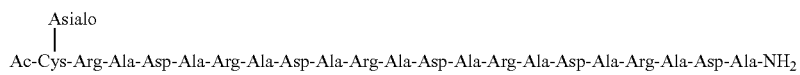

ESI-MS: (m/z) calcd for $C_{149}H_{250}N_{42}O_{78}S$: $[M+2H]^{2+}$ 1955.9, $[M+3H]^{3+}$ 1304.3, $[M+4H]^{4+}$ 978.5, found: 1955.8, 1304.2, 978.2.

Synthesis Example 23

Synthesis of C(DiGlcNAc)-(RADA)5

The polypeptide synthesized in Synthesis Example 21-1 (SEQ ID NO. 15) (19.4 mg, 8.70 μmol) and DiGlcNAc-BrAc synthesized in Synthesis Example 9 (20.0 mg, 21.7 μmol, 2.5 eq. to peptide 1) were dissolved in 0.2 M phosphate buffer (pH 7.2, 3.1 mL) comprising 33 μM of TCEP and 8 M guanidine hydrochloride, and reacted at room temperature for 2 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=95:5->60:40, 20 min. linear concentration gradient elution] to obtain a sugar chain-polypeptide complex represented by the following Formula (50) (SEQ ID NO. 18) (16.8 mg, 4.69 μmol, yield 54%).

[Chemical Formula 45]

Formula (50)

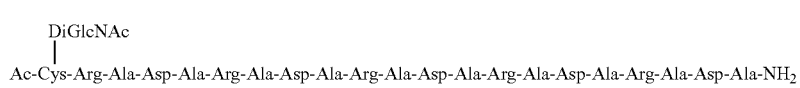

ESI-MS: (m/z) calcd for $C_{149}H_{250}N_{42}O_{78}S$: $[M+3H]^{3+}$ 1196.2, $[M+4H]^{4+}$ 897.4, found: 1195.9, 897.2.

Synthesis Example 24

Synthesis of C(GlcNAc)-(RADA)5

The polypeptide synthesized in Synthesis Example 21-1 (SEQ ID NO. 15) (18.8 mg, 8.43 μmol) and GlcNAc-BrAc synthesized in Synthesis Example 11 (8.7 mg, 25.3 μmol, 3.0 eq. to peptide 1) were dissolved in 7 M guanidine, 0.2 M phosphate buffer (pH 7.2, 4.2 mL), and reacted at room temperature for 1 hour.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=95:5->5:95, 15 min. linear concentration gradient elution] to obtain a sugar chain-polypeptide complex represented by the following Formula (51) (SEQ ID NO. 19) (14.9 mg, 5.99 μmol, yield 71%).

[Chemical Formula 46]

Formula (51)

ESI-MS: (m/z) calcd for $C_{95}H_{161}N_{39}O_{38}S$: $[M+2H]^{2+}$ 1245.8, $[M+3H]^{3+}$ 830.9, $[M+4H]^{4+}$ 623.4, found: 1245.1, 830.8, 623.3.

Synthesis Example 25

Synthesis of C(DiBn-Disialo)-(RADA)5

The polypeptide synthesized in Synthesis Example 21-1 (SEQ ID NO. 15) (20.7 mg, 9.29 µmol) and DiBn-Disialo-BrAc synthesized in Synthesis Example 12 (58.6 mg, 23.2 µmol, 2.5 eq. to peptide 1) were dissolved in 0.2 M phosphate buffer (pH 7.3, 3.2 mL) comprising 33 µM of TCEP and 8 M guanidine hydrochloride, and reacted at room temperature for 1 hour.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=85:15->73:27, 17 min. linear concentration gradient elution] to obtain a sugar chain-polypeptide complex represented by the following Formula (52) (SEQ ID NO. 20) (7.5 mg, 1.61 µmol, yield 17%).

[Chemical Formula 47]

Formula (52)

ESI-MS: (m/z) calcd for $C_{185}H_{296}N_{44}O_{94}S$: $[M+3H]^{3+}$ 1558.6, $[M+4H]^{4+}$ 1169.2, $[M+5H]^{5+}$ 935.5, found: 1558.4, 1169.0, 925.6.

Synthesis Example 26

Synthesis of C(PEG2000)-(RADA)5

The polypeptide synthesized in Synthesis Example 21-1 (SEQ ID NO. 15) (15.9 mg, 7.13 µmol) and a compound represented by the following Formula (53) (maleimidated PEG, product name: SUNBRIGHT™ ME-020MA, average molecular weight 2333, from NOF Corporation) (24.9 mg, 10.7 µmol, 1.5 eq. to peptide 1) were 0.2 M phosphate buffer (pH 7.3, 2.4 mL) comprising 8 M guanidine, and reacted at room temperature for 1 hour.

[Chemical Formula 48]

Formula (53)

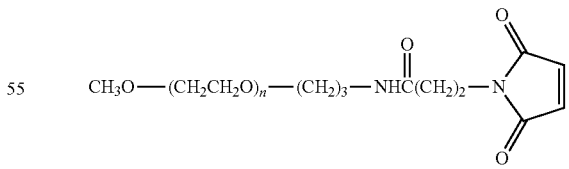

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=75:25->40:60, 12 min. linear concentration gradient elution] to obtain a sugar chain-polypeptide complex represented by the following Formula (54) (SEQ ID NO. 21) (10.9 mg, 2.39 µmol, yield 34%).

[Chemical Formula 49]

Formula (54)

Synthesis Example 27

Synthesis of C(Asialo)-(RATARAEA)2

Synthesis Example 27-1

Synthesis of Ac—C-(RATARAEA)2-NH$_2$

Rink amide PEGA resin (100 μmol) was taken up in a column for solid phase synthesis, washed with DMF and dichloromethane, followed by addition of a solution of Fmoc-Ala-OH (124.5 mg, 400 μmol), HCTU (157.2 mg, 380 μmol), and DIPEA (104.5 μL, 600 μmol) in DMF (2.5 mL), and this was shaken for 15 minutes. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (55) (SEQ ID NO. 22) was synthesized with a Prelude™ peptide synthesizer. The condensation reaction was carried out in DMF using HCTU as the condensing agent.

[Chemical Formula 50]

Formula (55)

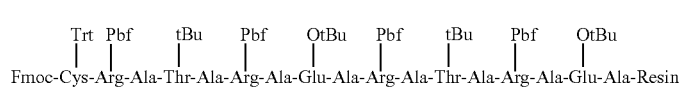

The Fmoc protecting group was removed by treatment with 20% piperidine in DMF. After washing with DMF and dichloromethane, acetic anhydride and pyridine were added and shaken for 1 hour. After washing with DMF and dichloromethane, TFA:water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=88:12->78:22%, 11 min. linear concentration gradient elution] to obtain a polypeptide represented by the following Formula (56) (SEQ ID NO. 23) (32.7 mg).

[Chemical Formula 51]

Ac-Cys-Arg-Ala-Thr-Ala-Arg-Ala-Glu-Ala-Arg-Ala-
Thr-Ala-Arg-Ala-Glu-Ala-NH$_2$   Formula (56)

Synthesis Example 27-2

Glycosylation Reaction of Thiol

The polypeptide synthesized in Synthesis Example 27-1 (SEQ ID NO. 23) (7.3 mg, 4.02 μmol) and Asialo-BrAc synthesized in Synthesis Example 8 (17.7 mg, 16.5 μmol, 1.5 eq. to peptide 1) were dissolved in 0.2 M phosphate buffer (pH 7.3, 1.3 mL) comprising 33 μM of TCEP and 8 M guanidine hydrochloride, and reacted at room temperature for 3 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=95:5->29:71, 11 min. linear concentration gradient elution] to obtain a sugar chain-polypeptide complex represented by the following Formula (57) (SEQ ID NO. 24) (4.6 mg, 1.32 μmol, yield 33%).

[Chemical Formula 52]

Formula (57)

ESI-MS: (m/z) calcd for $C_{123}H_{211}N_{35}O_{60}S$: $[M+3H]^{3+}$ 1166.5, $[M+4H]^{4+}$ 875.1, found: 1166.2, 875.1.

Synthesis Example 28

Synthesis of C(DiGlcNAc)-(RATARAEA)2

The polypeptide synthesized in Synthesis Example 27-1 (SEQ ID NO. 23) (20.0 mg, 11.0 μmol) and Disialo-BrAc synthesized in Synthesis Example 7 (23.7 mg, 16.5 μmol, 1.5 eq. to peptide 1) were dissolved in DMSO (0.9 mL). DIPEA (5.8 μL) was added to the solution and reacted at room temperature for 15 minutes.

To the reaction solution was added distilled water (4.0 mL), and this was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->29:71, 11 min linear concentration gradient elution] to obtain a sugar chain-polypeptide complex represented by the following Formula (58) (SEQ ID NO. 25) (23.9 mg, 7.53 μmol, yield 68%).

[Chemical Formula 53]

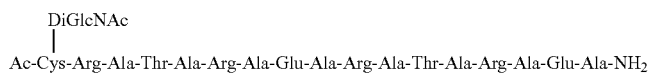

Formula (58)

ESI-MS: (m/z) calcd for $C_{123}H_{211}N_{35}O_{60}S$: $[M+3H]^{3+}$ 1058.4, $[M+4H]^{4+}$ 794.0, found: 1057.8, 793.9.

Synthesis Example 29

Synthesis of RAC(Asialo)-A-(RADA)3

Synthesis Example 29-1

Synthesis of Ac-RACA-(RADA)3-NH₂

Rink amide PEGA resin (100 μmol) was taken up in a column for solid phase synthesis, washed with DMF and dichloromethane, followed by addition of a solution of Fmoc-Ala-OH (124.5 mg, 400 μmol), HCTU (157.2 mg, 380 μmol), and DIPEA (104.5 μL, 600 μmol) in DMF (2.5 mL), and this was shaken for 15 minutes. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (59) (SEQ ID NO. 26) was synthesized with a Prelude™ peptide synthesizer. The condensation reaction was carried out in DMF using HCTU as the condensing agent.

[Chemical Formula 54]

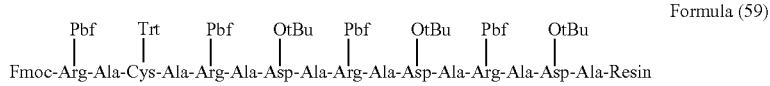

Formula (59)

The Fmoc protecting group was removed by treatment with 20% piperidine in DMF. After washing with DMF and dichloromethane, acetic anhydride and pyridine were added and shaken for 1 hour. After washing with DMF and dichloromethane, TFA:water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=88:12->78:22%, 11 min. linear concentration gradient elution] to obtain a polypeptide represented by the following Formula (60) (SEQ ID NO. 27) (32.7 mg).

[Chemical Formula 55]

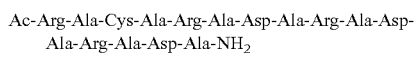

Formula (60)

Synthesis Example 29-2

Glycosylation Reaction of Thiol

The polypeptide synthesized in Synthesis Example 29-1 (SEQ ID NO. 27) (14.1 mg, 8.29 μmol) and Asialo-BrAc synthesized in Synthesis Example 8 (36.0 mg, 20.7 μmol, 2.5 eq. to peptide 1) were dissolved in 0.2 M phosphate buffer (pH 7.3, 2.6 mL) comprising 33 μM of TCEP and 8 M guanidine hydrochloride, and reacted at room temperature for 1 hour.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=95:5->29:71, 11 min. linear concentration gradient elution] to obtain a sugar chain-polypeptide complex represented by the following Formula (61) (SEQ ID NO. 28) (13.4 mg, 3.96 μmol, yield 48%).

[Chemical Formula 56]

Formula (61)

ESI-MS: (m/z) calcd for $C_{129}H_{218}N_{34}O_{69}S$: $[M+2H]^{2+}$ 1691.7, $[M+3H]^{3+}$ 1128.1, found: 1691.8, 1128.2.

Synthesis Example 30

Synthesis of RAC(DiGlcNAc)-A-(RADA)3

The polypeptide synthesized in Synthesis Example 29-1 (SEQ ID NO. 27) (10.1 mg, 5.94 μmol) and Disialo-BrAc synthesized in Synthesis Example 7 (21.3 mg, 14.8 μmol, 2.5 eq. to peptide 1) were dissolved in 0.2 M phosphate buffer (pH 7.3, 2.0 mL) comprising 33 μM of TCEP and 8 M guanidine hydrochloride, and reacted at room temperature for 4 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (62) (SEQ ID NO. 29) (11.9 mg, 3.89 μmol, yield 66%).

[Chemical Formula 57]

Formula (62)

ESI-MS: (m/z) calcd for $C_{117}H_{198}N_{34}O_{59}S$: $[M+2H]^{2+}$ 1529.5, $[M+3H]^{3+}$ 1020.0, $[M+4H]^{4+}$ 765.3, found: 1529.2, 1019.8, 765.1.

Synthesis Example 31

Synthesis of RC(Asialo)-DA-(RADA)3

Synthesis Example 31-1

Synthesis of Ac-RCDA-(RADA)3-NH$_2$

Rink amide PEGA resin (100 µmol) was taken up in a column for solid phase synthesis, washed with DMF and dichloromethane, followed by addition of a solution of Fmoc-Ala-OH (124.5 mg, 400 µmol), HCTU (157.2 mg, 380 µmol), and DIPEA (104.5 µL, 600 µmol) in DMF (2.5 mL), and this was shaken for 15 minutes. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (63) (SEQ ID NO. 30) was synthesized with a Prelude™ peptide synthesizer. The condensation reaction was carried out in DMF using HCTU as the condensing agent.

[Chemical Formula 58]

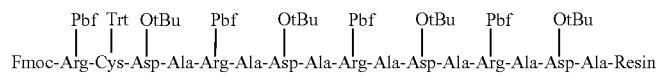

Formula (63)

The Fmoc protecting group was removed by treatment with 20% piperidine in DMF. After washing with DMF and dichloromethane, acetic anhydride and pyridine were added and shaken for 1 hour. After washing with DMF and dichloromethane, TFA:water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=88:12->78:22%, 11 min. linear concentration gradient elution] to obtain a polypeptide represented by the following Formula (64) (SEQ ID NO. 31) (32.7 mg).

[Chemical Formula 59]

Ac-Arg-Cys-Asp-Ala-Arg-Ala-Asp-Ala-Arg-Ala-Asp-Ala-Arg-Ala-Asp-Ala-NH$_2$    Formula (64)

Synthesis Example 31-2

Glycosylation Reaction of Thiol

The polypeptide synthesized in Synthesis Example 31-1 (SEQ ID NO. 31) (14.8 mg, 8.48 µmol) and Asialo-BrAc synthesized in Synthesis Example 8 (37.4 mg, 21.2 µmol, 2.5 eq. to peptide 1) were dissolved in 0.2 M phosphate buffer (pH 7.3, 2.8 mL) comprising 33 µM of TCEP and 8 M guanidine hydrochloride, and reacted at room temperature for 2 hours.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=95:5->29:71, 11 min. linear concentration gradient elution] to obtain a sugar chain-polypeptide complex represented by the following Formula (65) (SEQ ID NO. 32) (21.7 mg, 6.34 µmol, yield 75%).

[Chemical Formula 60]

Formula (65)

ESI-MS: (m/z) calcd for $C_{130}H_{218}N_{34}O_{71}S$: $[M+2H]^{2+}$ 1713.7, $[M+3H]^{3+}$ 1142.8, $[M+4H]^{4+}$ 857.3, found: 1713.7, 1142.5, 857.1.

Synthesis Example 32

Synthesis of RC(DiGlcNAc)-DA-(RADA)3

The polypeptide synthesized in Synthesis Example 31-1 (SEQ ID NO. 31) (11.0 mg, 6.30 μmol) and DiGlcNAc-BrAc synthesized in Synthesis Example 9 (22.6 mg, 15.7 μmol, 2.5 eq. to peptide 1) were dissolved in 0.2 M phosphate buffer (pH 7.3, 2.1 mL) comprising 33 μM of TCEP and 8 M guanidine hydrochloride, and reacted at room temperature for 3 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (66) (SEQ ID NO. 33) (19.0 mg, 6.12 μmol, yield 97%).

[Chemical Formula 61]

Formula (66)

ESI-MS: (m/z) calcd for $C_{118}H_{198}N_{34}O_{61}S$: $[M+2H]^{2+}$ 1551.6, $[M+3H]^{3+}$ 1034.7, $[M+4H]^{4+}$ 776.3, found: 1551.2, 1034.5, 776.1.

Synthesis Example 33

Synthesis of C(Asialo)-ADA-(RADA)3

Synthesis Example 33-1

Synthesis of Ac-CADA-(RADA)3-NH₂

Rink amide PEGA resin (100 μmol) was taken up in a column for solid phase synthesis, washed with DMF and dichloromethane, followed by addition of a solution of Fmoc-Ala-OH (124.5 mg, 400 μmol), HCTU (157.2 mg, 380 μmol), and DIPEA (104.5 μL, 600 μmol) in DMF (2.5 mL), and this was shaken for 15 minutes. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (67) (SEQ ID NO. 34) was synthesized with a Prelude™ peptide synthesizer. The condensation reaction was carried out in DMF using HCTU as the condensing agent.

[Chemical Formula 62]

Formula (67)

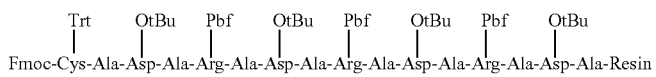

The Fmoc protecting group was removed by treatment with 20% piperidine in DMF. After washing with DMF and dichloromethane, acetic anhydride and pyridine were added and shaken for 1 hour. After washing with DMF and dichloromethane, TFA:water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=88:12->78:22%, 11 min. linear concentration gradient elution] to obtain a polypeptide represented by the following Formula (68) (SEQ ID NO. 35) (32.7 mg).

[Chemical Formula 63]

Ac-Cys-Ala-Asp-Ala-Arg-Ala-Asp-Ala-Arg-Ala-Asp-
Ala-Arg-Ala-Asp-Ala-NH₂    Formula (68)

Synthesis Example 33-2

Glycosylation Reaction of Thiol

The polypeptide synthesized in Synthesis Example 33-1 (SEQ ID NO. 35) (13.0 mg, 7.83 μmol) and Asialo-BrAc

[Chemical Formula 64]

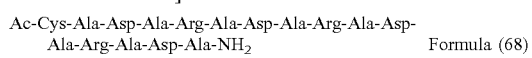

Formula (69)

synthesized in Synthesis Example 8 (34.5 mg, 19.6 μmol, 2.5 eq. to peptide 1) were dissolved in 0.2 M phosphate buffer (pH 7.3, 2.6 mL) comprising 33 μM of TCEP and 8 M guanidine hydrochloride, and reacted at room temperature for 2 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=95:5->29:71, 11 min. linear concentration gradient elution] to obtain a sugar chain-polypeptide complex represented by the following Formula (69) (SEQ ID NO. 36) (15.2 mg, 4.55 μmol, yield 58%).

ESI-MS: (m/z) calcd for $C_{127}H_{211}N_{31}O_{71}S$: $[M+2H]^{2+}$ 1671.1, $[M+3H]^{3+}$ 1114.4, $[M+4H]^{4+}$ 836.1, found: 1671.2, 1114.1, 835.8.

Synthesis Example 34

Synthesis of C(DiGlcNAc)-ADA-(RADA)3

The polypeptide synthesized in Synthesis Example 33-1 (9.9 mg, 5.96 μmol) and DiGlcNAc-BrAc synthesized in Synthesis Example 9 (21.4 mg, 15.7 μmol, 2.5 eq. to peptide 1) were dissolved in 0.2 M phosphate buffer (pH 7.3, 2.1 mL) comprising 33 μM of TCEP and 8 M guanidine hydrochloride, and reacted at room temperature for 4 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (70) (SEQ ID NO. 37) (10.9 mg, 3.61 μmol, yield 61%).

[Chemical Formula 65]

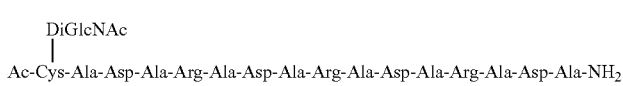

Formula (70)

ESI-MS: (m/z) calcd for $C_{115}H_{191}N_{31}O_{61}S$: $[M+2H]^{2+}$ 1509.0, $[M+3H]^{3+}$ 1006.3, $[M+4H]^{4+}$ 755.0, found: 1508.7, 1006.1, 754.9.

Synthesis Example 35

Synthesis of 2C(Maltose)-(RADA)4

Synthesis Example 35-1

Synthesis of Ac-2C-(RADA)4-NH₂

Rink amide PEGA resin (100 μmol) was taken up in a column for solid phase synthesis, washed with DMF and dichloromethane, followed by addition of a solution of Fmoc-Ala-OH (124.5 mg, 400 μmol), HCTU (157.2 mg, 380 μmol), and DIPEA (104.5 μL, 600 μmol) in DMF (2.5 mL), and this was shaken for 15 minutes. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (71) (SEQ ID NO. 38) was synthesized with a Prelude™ peptide synthesizer. The condensation reaction was carried out in DMF using HCTU as the condensing agent.

[Chemical Formula 66]

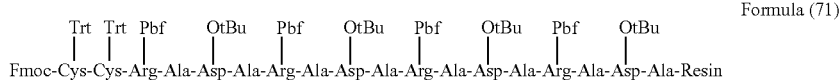

Formula (71)

The Fmoc protecting group was removed by treatment with 20% piperidine in DMF. After washing with DMF and dichloromethane, acetic anhydride and pyridine were added and shaken for 1 hour. After washing with DMF and dichloromethane, TFA:water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25%, 11 min linear concentration gradient elution] to obtain a polypeptide represented by the following Formula (72) (SEQ ID NO. 39).

[Chemical Formula 67]

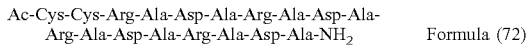

Formula (72)

[Chemical Formula 68]

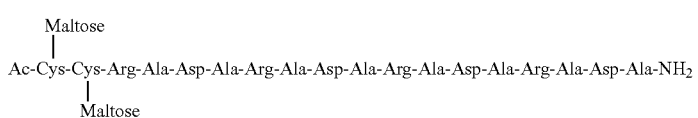

Formula (73)

(35-2) Glycosylation Reaction of Thiol

The polypeptide synthesized in Synthesis Example 35-1 (SEQ ID NO. 39) (9.8 mg, 5.11 μmol) and Maltose-BrAc synthesized in Synthesis Example 2 (11.8 mg, 54.6 μmol, 5.0 eq. to peptide 1) were dissolved in 0.2 M phosphate buffer (pH 7.3, 1.7 mL) comprising 33 μM of TCEP and 8 M guanidine hydrochloride, and reacted at room temperature for 1.5 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (73) (SEQ ID NO. 40) (9.2 mg, 3.43 μmol, yield 67%).

ESI-MS: (m/z) calcd for $C_{100}H_{169}N_{33}O_{49}S_2$: $[M+2H]^{2+}$ 1341.9, $[M+3H]^{3+}$ 894.9, $[M+4H]^{4+}$ 671.4, found: 1341.6, 894.7, 671.3.

Synthesis Example 36

Synthesis of 2C(Maltotriose)-(RADA)4

The polypeptide synthesized in Synthesis Example 35-1 (SEQ ID NO. 39) (17.5 mg, 9.12 μmol) and Maltotriose-BrAc synthesized in Synthesis Example 3 (34.1 mg, 54.6 μmol, 6.0 eq. to peptide 1) were dissolved in 0.2 M phosphate buffer (pH 7.3, 3.1 mL) comprising 33 μM of TCEP and 8 M guanidine hydrochloride, and reacted at room temperature for 1.5 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (74) (SEQ ID NO. 41) (19.6 mg, 3.61 μmol, yield 72%).

[Chemical Formula 69]

Formula (74)

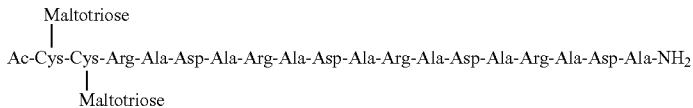

Ac-Cys-Cys-Arg-Ala-Asp-Ala-Arg-Ala-Asp-Ala-Arg-Ala-Asp-Ala-Arg-Ala-Asp-Ala-NH$_2$ with Maltotriose on both Cys residues ESI-MS: (m/z) calcd for $C_{112}H_{189}N_{33}O_{59}S_2$: $[M+2H]^{2+}$ 1504.0, $[M+3H]^{3+}$ 1003.0, $[M+4H]^{4+}$ 752.5, found: 1503.7, 1002.7, 752.3.

Synthesis Example 37

Synthesis of 2C(Maltotetraose)-(RADA)4

The polypeptide synthesized in Synthesis Example 35-1 (SEQ ID NO. 39) (9.8 mg, 5.11 µmol) and Maltotetraose-BrAc synthesized in Synthesis Example 4 (20.1 mg, 25.5 µmol, 5.0 eq. to peptide 1) were dissolved in 0.2 M phosphate buffer (pH 7.3, 1.7 mL) comprising 33 µM of TCEP and 8 M guanidine hydrochloride, and reacted at room temperature for 2 hours.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (75) (SEQ ID NO. 42) (10.6 mg, 3.18 µmol, yield 62%).

[Chemical Formula 70]

Formula (75)

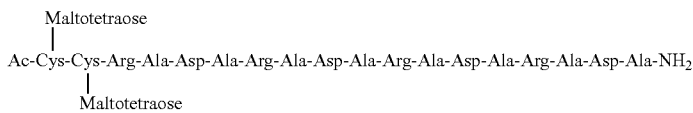

Ac-Cys-Cys-Arg-Ala-Asp-Ala-Arg-Ala-Asp-Ala-Arg-Ala-Asp-Ala-Arg-Ala-Asp-Ala-NH$_2$ with Maltotetraose on both Cys residues ESI-MS: (m/z) calcd for $C_{124}H_{209}N_{33}O_{69}S_2$: $[M+2H]^{2+}$ 1666.2, $[M+3H]^{3+}$ 1111.1, $[M+4H]^{4+}$ 833.6, found: 1666.2, 1110.8, 833.3.

Synthesis Example 38

Synthesis of 3C(Maltose)-(RADA)4

Synthesis Example 38-1

Synthesis of Ac-3C-(RADA)4-NH$_2$

Rink amide PEGA resin (100 µmol) was taken up in a column for solid phase synthesis, washed with DMF and dichloromethane, followed by addition of a solution of Fmoc-Ala-OH (124.5 mg, 400 µmol), HCTU (157.2 mg, 380 µmol), and DIPEA (104.5 µL, 600 µmol) in DMF (2.5 mL), and this was shaken for 15 minutes. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (76) (SEQ ID NO. 43) was synthesized with a Prelude™ peptide synthesizer. The condensation reaction was carried out in DMF using HCTU as the condensing agent.

[Chemical Formula 71]

Formula (76)

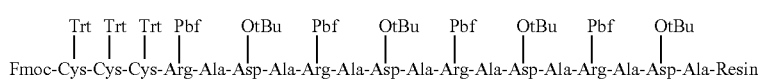

The Fmoc protecting group was removed by treatment with 20% piperidine in DMF. After washing with DMF and dichloromethane, acetic anhydride and pyridine were added and shaken for 1 hour. After washing with DMF and dichloromethane, TFA:water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25%, 11 min. linear concentration gradient elution] to obtain a polypeptide represented by the following Formula (77) (SEQ ID NO. 44).

[Chemical Formula 72]

Ac-Cys-Cys-Cys-Arg-Ala-Asp-Ala-Arg-Ala-Asp-Ala-Arg-Ala-Asp-Ala-Arg-Ala-Asp-Ala-NH$_2$     Formula (77)

Synthesis Example 38-2

Glycosylation Reaction of Thiol

The polypeptide synthesized in Synthesis Example 38-1 (SEQ ID NO. 44) (15.0 mg, 7.42 μmol) and Maltose-BrAc synthesized in Synthesis Example 2 (20.6 mg, 44.6 μmol, 6.0 eq. to peptide 1) were dissolved in 0.2 M phosphate buffer (pH 7.3, 2.4 mL) comprising 33 μM of TCEP and 8 M guanidine hydrochloride, and reacted at room temperature for 3 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (78) (SEQ ID NO. 45) (16.1 mg, 5.09 μmol, yield 69%).

[Chemical Formula 73]

Formula (78)

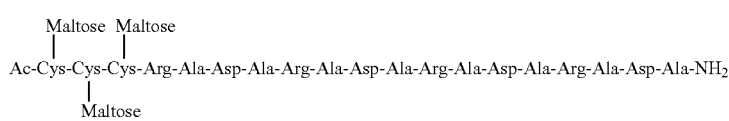

ESI-MS: (m/z) calcd for $C_{117}H_{197}N_{35}O_{61}S_3$: $[M+2H]^{2+}$ 1584.1, $[M+3H]^{3+}$ 1056.4, $[M+4H]^{4+}$ 792.6, found: 1583.7, 1056.1, 792.4.

Synthesis Example 39

Synthesis of (RADA)2-C(Maltose)-(ARAD)2

Synthesis Example 39-1

Synthesis of Ac-(RADA)2-C-(ARAD)2-NH$_2$

Rink amide PEGA resin (100 μmol) was taken up in a column for solid phase synthesis, washed with DMF and dichloromethane, followed by addition of a solution of Fmoc-Asp(OtBu)-OH (164.6 mg, 400 μmol), HCTU (157.2 mg, 380 μmol), and DIPEA (104.5 μL, 600 μmol) in DMF (2.5 mL), and this was shaken for 15 minutes. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (79) (SEQ ID NO. 46) was synthesized with a Prelude™ peptide synthesizer. The condensation reaction was carried out in DMF using HCTU as the condensing agent.

[Chemical Formula 74]

Formula (79)

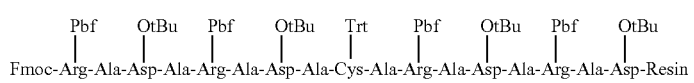

The Fmoc protecting group was removed by treatment with 20% piperidine in DMF. After washing with DMF and dichloromethane, acetic anhydride and pyridine were added and shaken for 1 hour. After washing with DMF and dichloromethane, TFA:water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=90:10->75:25%, 15 min linear concentration gradient elution] to obtain a polypeptide represented by the following Formula (80) (SEQ ID NO. 47).
[Chemical Formula 75]

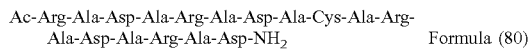

Formula (80)

Synthesis Example 39-2

Glycosylation Reaction of Thiol

The polypeptide synthesized in Synthesis Example 39-1 (SEQ ID NO. 47) (15.4 mg, 8.48 µmol) and Maltose-BrAc synthesized in Synthesis Example 2 (9.8 mg, 21.2 µmol, 2.5 eq. to peptide 1) were dissolved in 0.2 M phosphate buffer (pH 7.3, 2.9 mL) comprising 33 µM of TCEP and 8 M guanidine hydrochloride, and reacted at room temperature for 3 hours.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (81) (SEQ ID NO. 48) (17.8 mg, 8.10 µmol, yield 96%).

[Chemical Formula 76]

Formula (81)

ESI-MS: (m/z) calcd for $C_{83}H_{141}N_{31}O_{37}S$: $[M+2H]^{2+}$ 1099.6, $[M+3H]^{3+}$ 733.4, $[M+4H]^{4+}$ 550.3, found: 1099.5, 733.0, 550.2.

Synthesis Example 40

Synthesis of (RADA)2-C(Maltotriose)-(ARAD)2

The polypeptide synthesized in Synthesis Example 39-1 (SEQ ID NO. 47) (14.8 mg, 8.15 µmol) and Maltotriose-BrAc synthesized in Synthesis Example 3 (12.7 mg, 20.3 µmol, 2.5 eq. to peptide 1) were dissolved in 0.2 M phosphate buffer (pH 7.3, 2.8 mL) comprising 33 µM of TCEP and 8 M guanidine hydrochloride, and reacted at room temperature for 3 hours.

The reaction solution was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (82) (SEQ ID NO. 49) (13.8 mg, 5.85 µmol, yield 72%).

[Chemical Formula 77]

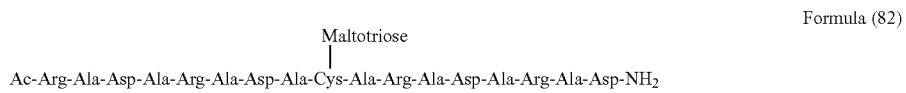

Formula (82)

ESI-MS: (m/z) calcd for $C_{89}H_{151}N_{31}O_{42}S$: $[M+2H]^{2+}$ 1180.2, $[M+3H]^{3+}$ 787.1, $[M+4H]^{4+}$ 590.6, found: 1180.5, 787.0, 590.8.

Synthesis Example 41

Synthesis of (RADA)2-C(Maltotetraose)-(ARAD)2

The polypeptide synthesized in Synthesis Example 39-1 (SEQ ID NO. 47) (14.0 mg, 7.71 μmol) and Maltotetraose-BrAc synthesized in Synthesis Example 4 (15.2 mg, 20.3 μmol), 2.5 eq. to peptide 1) were dissolved in 0.2 M phosphate buffer (pH 7.3, 2.6 mL) comprising 33 Wl of TCEP and 8 M guanidine hydrochloride, and reacted at room temperature for 2.5 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (83) (SEQ ID NO. 50) (14.9 mg, 5.91 μmol, yield 77%).

[Chemical Formula 78]

dichloromethane, followed by addition of a solution of Fmoc-Cys(Trt)-OH (124.5 mg, 400 μmol), HCTU (157.2 mg, 380 μmol), and 2,4,6-trimethylpyridine (79.3 μL, 600 μmol) in DMF (2.5 mL), and this was shaken for 1 hour. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (84) (SEQ ID NO. 51) was synthesized with a Prelude™ peptide synthesizer. The condensation reaction was carried out in DMF using HCTU as the condensing agent.

[Chemical Formula 79]

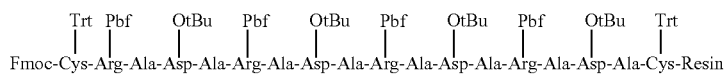

Formula (84)

The Fmoc protecting group was removed by treatment with 20% piperidine in DMF. After washing with DMF and dichloromethane, acetic anhydride and pyridine were added and shaken for 1 hour. After washing with DMF and dichloromethane, TFA:water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:

Formula (83)

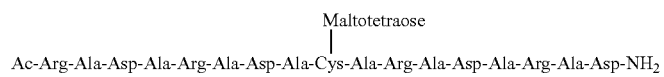

ESI-MS: (m/z) calcd for $C_{95}H_{161}N_{31}O_{47}S$: $[M+2H]^{2+}$ 1261.8, $[M+3H]^{3+}$ 841.5, $[M+4H]^{4+}$ 631.4, found: 1261.6, 841.4, 631.3.

Synthesis Example 42

Synthesis of C(Maltose)-(RADA)-4-C(Maltose)

Synthesis Example 42-1

Synthesis of Ac—C-(RADA)4-C—NH2

Rink amide PEGA resin (100 μmol) was taken up in a column for solid phase synthesis, washed with DMF and 25%, 15 min. linear concentration gradient elution] to obtain a polypeptide represented by the following Formula (85) (SEQ ID NO. 52).
[Chemical Formula 80]

Av-Cys-Arg-Ala-Asp-Ala-Arg-Ala-Asp-Ala-Arg-Ala-Asp-Ala-Arg-Ala-Asp-Ala-Cys-NH2    Formula (85)

Synthesis Example 42-2

Glycosylation Reaction of Thiol

The polypeptide synthesized in Synthesis Example 42-1 (SEQ ID NO. 52) (14.7 mg, 7.66 μmol) and Maltose-BrAc synthesized in Synthesis Example 2 (17.7 mg, 38.3 μmol, 5 eq. to peptide 1) were dissolved in 33 μM of TCEP and a hydrochloride salt comprising 8 M guanidine hydrochloride, 0.2 M phosphate buffer (pH 7.3, 2.6 mL), and reacted at room temperature for 2 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (86) (SEQ ID NO. 53) (6.5 mg, 2.42 μmol, yield 32%).

[Chemical Formula 81]

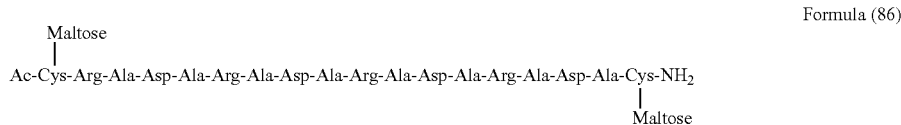

Formula (86)

ESI-MS: (m/z) calcd for $C_{100}H_{169}N_{33}O_{49}S_2$: $[M+2H]^{2+}$ 1341.9, $[M+3H]^{3+}$ 894.9, $[M+4H]^{4+}$ 671.4, found: 1341.5, 894.7, 671.3.

Synthesis Example 43

Synthesis of C(Maltotriose)-(RADA)4-C(Maltotriose)

The polypeptide synthesized in Synthesis Example 42-1 (SEQ ID NO. 52) (13.9 mg, 7.24 μmol) and Maltotriose-BrAc synthesized in Synthesis Example 3 (22.6 mg, 36.2 μmol, 5 eq. to peptide 1) were dissolved in 33 μM of TCEP and a hydrochloride salt comprising 8 M guanidine hydrochloride, 0.2 M phosphate buffer (pH 7.3, 2.5 mL), and reacted at room temperature for 2 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (87) (SEQ ID NO. 54) (9.6 mg, 3.19 μmol, yield 44%).

[Chemical Formula 82]

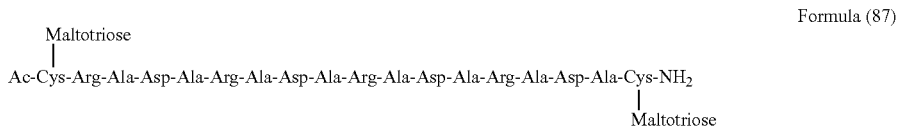

Formula (87)

ESI-MS: (m/z) calcd for $C_{112}H_{189}N_{33}O_{59}S_2$: $[M+2H]^{2+}$ 1504.1, $[M+3H]^{3+}$ 1003.0, $[M+4H]^{4+}$ 752.5, found: 1503.8, 1002.8, 752.4.

Synthesis Example 44

Synthesis of Ac-(RADA)4-C(DiGlcNAc)

Synthesis Example 44-1

Synthesis of Ac-(RADA)4-C—NH$_2$

Rink amide PEGA resin (100 μmol) was taken up in a column for solid phase synthesis, washed with DMF and dichloromethane, followed by addition of a solution of Fmoc-Cys(Trt)-OH (124.5 mg, 400 μmol), HCTU (157.2 mg, 380 μmol), and 2,4,6-trimethylpyridine (79.3 μL, 600 μmol) in DMF (2.5 mL), and this was shaken for 1 hour. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (88) (SEQ ID NO. 55) was synthesized with a Prelude™ peptide synthesizer. The condensation reaction was carried out in DMF using HCTU as the condensing agent.

[Chemical Formula 83]

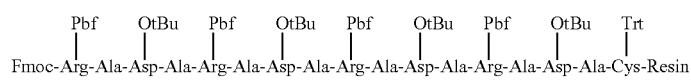

Formula (88)

The Fmoc protecting group was removed by treatment with 20% piperidine in DMF. After washing with DMF and dichloromethane, acetic anhydride and pyridine were added and shaken for 1 hour. After washing with DMF and dichloromethane, TFA:water:triisopropylsilane:ethanedithiol (=90:2.5:5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25%, 15 min. linear concentration gradient elution] to obtain a polypeptide represented by the following Formula (89) (SEQ ID NO. 56).

[Chemical Formula 84]

Ac-Arg-Ala-Asp-Ala-Arg-Ala-Asp-Ala-Arg-Ala-Asp-Ala-Arg-Ala-Asp-Ala-Cys-NH$_2$    Formula (89)

Synthesis Example 44-2

Glycosylation Reaction of Thiol

The polypeptide synthesized in Synthesis Example 44-1 (SEQ ID NO. 56) (15.1 mg, 8.31 μmol) and DiGlcNAc-BrAc synthesized in Synthesis Example 9 (29.8 mg, 20.8 μmol, 2.5 eq. to peptide 1) were dissolved in 0.2 M phosphate buffer (pH 7.3, 2.8 mL) comprising 33 μM of TCEP and 8 M guanidine hydrochloride, and reacted at room temperature for 3 hours.

The reaction solution was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25, 15 min. linear concentration gradient elution] to obtain a sugar chain-polypeptide complex represented by the following Formula (90) (SEQ ID NO. 57) (15.8 mg, 5.01 μmol, yield 60%).

[Chemical Formula 85]

Formula (90)

ESI-MS: (m/z) calcd for $C_{121}H_{203}N_{35}O_{62}S$: $[M+2H]^{2+}$ 1587.1, $[M+3H]^{3+}$ 1058.4, $[M+4H]^{4+}$ 794.0, found: 1586.7, 1058.1, 793.8.

Synthesis Example 45

Synthesis of Ac—N(Asialo) (RADA)4

Synthesis Example 45-1

Synthesis of Fmoc-(RADA)4-Resin

Rink amide PEGA resin (100 μmol) was taken up in a column for solid phase synthesis, washed with DMF and dichloromethane, followed by addition of a solution of Fmoc-Ala-OH (124.5 mg, 400 μmol), HCTU (157.2 mg, 380 µmol), and DIPEA (104.5 µL, 600 µmol) in DMF (2.5 mL), and this was shaken for 15 minutes. After washing with dichloromethane and DMF, the Fmoc protecting group was removed by treatment with 20% piperidine in DMF. After washing with DMF, a resin-bound polypeptide protected with peptide solid phase synthesis method by Fmoc method represented by the following Formula (91) (SEQ ID NO. 58) was synthesized with a Prelude™ peptide synthesizer. The condensation reaction was carried out in DMF using HCTU as the condensing agent.

[Chemical Formula 86]

Formula (91)

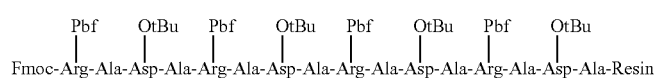

Synthesis Example 45-2

Condensation Reaction of the Sugar Chain on the Resin

The Fmoc protecting group of the resin-bound polypeptide (10 µmol) synthesized in Synthesis Example 45-1 was removed by treatment with 20% piperidine in DMF. After washing with DMF and dichloromethane, Fmoc-Asn(Asialo)-OH represented by the following Formula (92) (29.8 mg, 15 µmol), DMF-DMSO (1/1, v/v, 433 µL), O-(benzotriazol-1-yl)-N,N,N',N'-tetramethyluronium tetrafluoroborate (TBTU) (6.4 mg, 30 µmol), and DIPEA (5.2 µL, 30 µmol) were sequentially added and shaken overnight. After washing with DMF and dichloromethane, the Fmoc protecting group was removed by treatment with 20% piperidine in DMF. After washing with DMF and dichloromethane, a solution of acetic acid (2.86 µL, 50 µmol), 1-hydroxybenzotriazole (HOBt) (6.8 mg, 50 µmol), and N,N'-diisopropylcarbodiimide (DIC) (7.3 µL, 50 µmol) in DMF (500 µL) was added and shaken for 1 hour.

[Chemical Formula 87]

Formula (92)

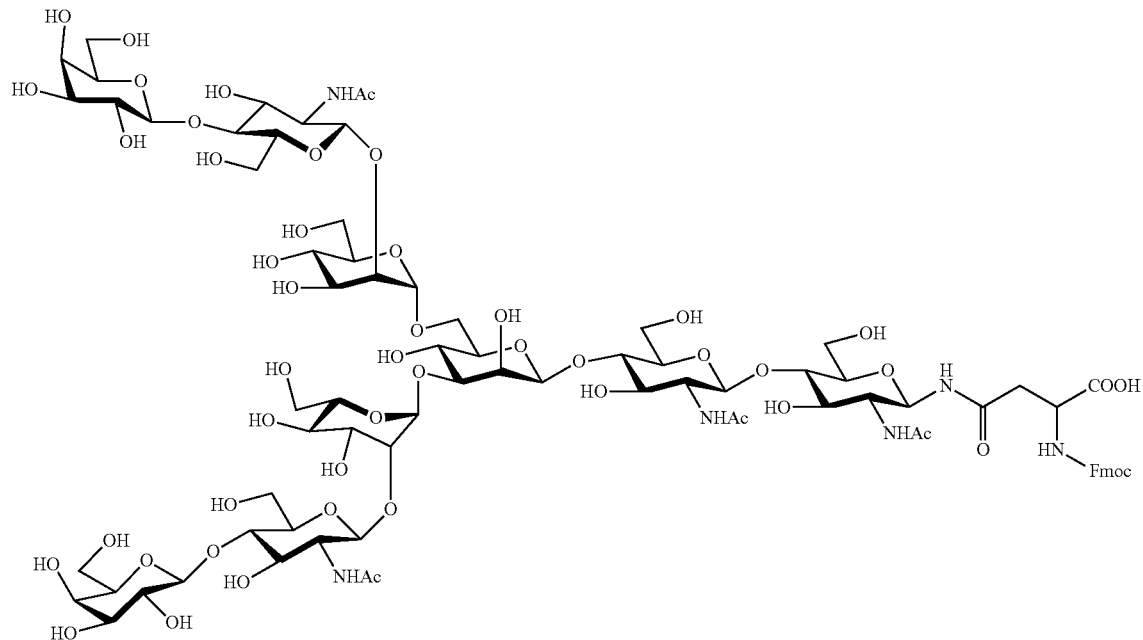

After washing with DMF and dichloromethane, TFA:water:triisopropylsilane (=95:2.5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 µm), φ 20×250 mm, flow rate: 7.0 mL/min, developing solvent A: 0.1% aq. TFA, B: 0.09% TFA/10% water/90% acetonitrile, gradient A:B=90:10->75:25%, 15 min. linear concentration gradient elution] to obtain a sugar chain-polypeptide complex represented by the following Formula (93) (SEQ ID NO. 59) (5.5 mg).

[Chemical Formula 88]

Formula (93)

ESI-MS: (m/z) calcd for $C_{132}H_{221}N_{35}O_{72}$: $[M+2H]^{2+}$ 1726.2, $[M+3H]^{3+}$ 1151.1, $[M+4H]^{4+}$ 863.6, found: 1726.0, 1150.8, 863.4.

Synthesis Example 46 Synthesis of Ac—N(DiGlcNAc) (RADA)4

The Fmoc protecting group of the resin-bound polypeptide (32.1 µmol) synthesized in Synthesis Example 45-1 was removed by treatment with 20% piperidine in DMF. After washing with DMF and dichloromethane, Fmoc-Asn(DiGlcNAc)-OH represented by the following Formula (94) (79.5 mg, 15 µmol), DMSO-DMF (1/1, v/v, 2.5 mL), TBTU (20.6 mg, 96.3 µmol), and DIPEA (17.2 µL, 96.3 µmol) were sequentially added and shaken for 2 hours. After washing with DMF and dichloromethane, the Fmoc protecting group was removed by treatment with 20% piperidine in DMF. After washing with DMF and dichloromethane, a solution of acetic acid (9.2 µL, 160.5 µmol), HOBt (21.6 mg, 160.5 µmol), and DIC (25.1 µL, 160.5 µmol) in DMF (2 mL) was added and shaken for 1 hour.

[Chemical Formula 89]

Formula (94)

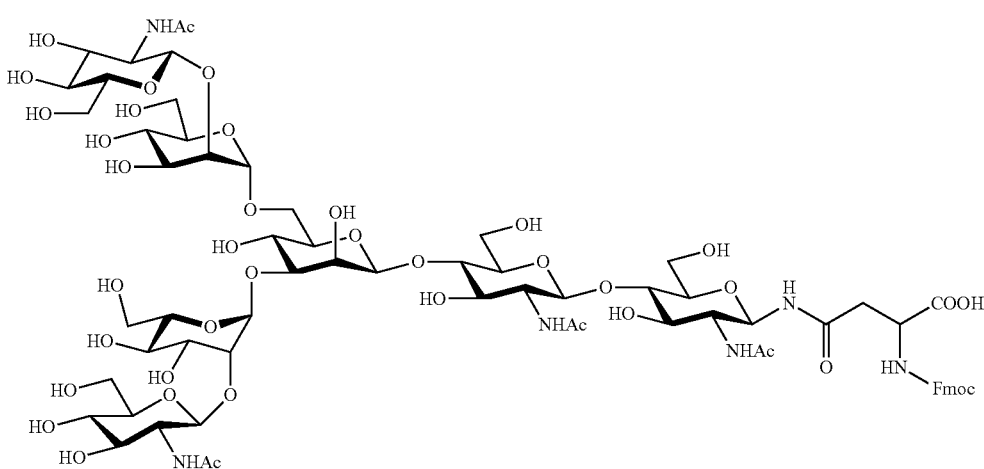

After washing with DMF and dichloromethane, TFA:water:triisopropylsilane (=95:2.5:2.5) was added, and this was shaken for 4 hours at room temperature. The resin was filtered off, chilled diethyl ether was added to the filtrate, and crude peptide was obtained as the precipitate. A portion of the crude peptide was purified with HPLC [column: SHISEIDO CAPCELL PAK C18 UG-120 (5 μm), φ 20×250 mm, flow rate: 7.0 mL/min, developing solvent A: 0.1% aq. TFA, B: 0.09% TFA/10% water/90% acetonitrile, gradient A:B=90:10->75:25%, 15 min. linear concentration gradient elution] to obtain a sugar chain-polypeptide complex represented by the following Formula (95) (SEQ ID NO. 60) (31.2 mg).

[Chemical Formula 90]

Formula (95)

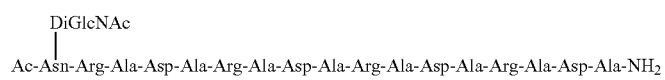

Ac-Asn-Arg-Ala-Asp-Ala-Arg-Ala-Asp-Ala-Arg-Ala-Asp-Ala-Arg-Ala-Asp-Ala-NH$_2$

ESI-MS: (m/z) calcd for $C_{120}H_{201}N_{35}O_{62}$: $[M+2H]^{2+}$ 1564.1, $[M+3H]^{3+}$ 1043.0, $[M+4H]^{4+}$ 782.5, found: 1563.7, 1043.8, 782.3.

Example 1

Evaluation of Hydrogel Property by Steel Ball Loading Test-1

Ten mg of the sugar chain-polypeptide complex or 10 mg of the control polypeptide were dissolved in 500 μL of ultrapure water to prepare 2 wt. % polypeptide solutions. Equal amounts of this solution and various buffers were each added to a Durham's tube (6*30 mm, Maruemu Corporation), and hydrogels having peptide concentration of 1 wt. % were created by vigorous stirring by vortexing. In doing so, citrate-phosphate buffer (pH 2.0 and 3.5), phosphate buffer (pH 7.4), and phosphate-sodium hydroxide buffer (pH 11.5) were employed as the buffer. The surface of the hydrogel inside the Durham's tube was horizontally placed, left still for 20 minutes under room temperature conditions, and a steel ball (diameter 1.56 mm, weight 16 mg, FUNABE SEIKO Co., Ltd.) was loaded on the hydrogel. After 10 minutes, the position of the steel ball was observed by visual confirmation.

The position of the steel ball inside the Durham's tube was evaluated in 3 grades. The state of the steel ball staying near the hydrogel surface was set as ○, sinking after loading and staying internally was set as Δ, and sinking to the bottom of the Durham's tube was set as X. In addition, * was added to those where the hydrogel was not uniform and clouding or insoluble matter (precipitate) was observed. A hydrogel where the steel ball stays around the surface (○) and no clouding or insoluble matter is seen (no *) was thought to be a gel that is transparent and uniform. The photographs obtained are shown in FIG. 1, and the evaluation results are shown in Table 1.

In Table 1, the "number of sugar residues" indicates the total number of sugar residues present in the sugar chain bound to the sugar chain-polypeptide complex. Moreover, compound numbers indicated in the table are assigned for convenience in description and does not match the manufacturing example number.

TABLE 1

| Compound | | No. of Sugar | pH | | | |
|---|---|---|---|---|---|---|
| No. | Name | Residues | 2.0 | 3.5 | 7.4 | 11.5 |
| 1 | (RADA)4 | — | ○ | Δ* | X* | X* |
| 2 | C(DiGlcNAc)-(RADA)4 | 7 | ○ | ○ | ○ | ○ |

As shown in FIG. 1 and Table 1, C(DiGlcNAc)-(RADA)4 formed transparent and uniform hydrogels at all pH ranges (pH 2.0-pH 11.5), and retained the steel ball near the hydrogel surface. On the other hand, (RADA)4 formed a transparent and uniform hydrogel at pH 2.0 and retained the steel ball near the hydrogel surface, but formed an ununiform hydrogel with clouding at pH 3.5 or higher, and the steel ball penetrated to the inside of the hydrogel or sank to the bottom of the Durham's tube.

From the above, it was found that C(DiGlcNAc)-(RADA)4 can form a transparent and uniform hydrogel while maintaining the strength of the hydrogel at a neutral pH.

Example 2

Evaluation of Hydrogel Property by Steel Ball Loading Test-2

Steel ball loading tests with C(Disialo)-(RADA)4, C(Asialo)-(RADA)4, C(Disialo)-(RADA)5, C(DiGlcNAc)-(RADA)5, and (RADA)4 were carried out with a method similar to Example 1. The evaluation results obtained are shown in Table 2.

TABLE 2

| Compound | | No. of Sugar | pH | |
|---|---|---|---|---|
| No. | Name | Residues | 3.5 | 7.4 |
| 1 | (RADA)4 | — | Δ* | X* |
| 2 | C(DiGlcNAc)-(RADA)4 | 7 | ○ | ○ |
| 3 | C(Disialo)-(RADA)4 | 11 | ○ | ○ |
| 4 | C(Asialo)-(RADA)4 | 9 | ○ | ○ |
| 5 | C(Disialo)-(RADA)5 | 11 | ○ | ○ |
| 6 | C(Asialo)-(RADA)5 | 9 | ○ | ○ |
| 7 | C(DiGlcNAc)-(RADA)5 | 7 | ○ | ○ |

As shown in Table 2, those having a modification of a relatively large sugar chain at the end of (RADA)4 formed transparent and uniform hydrogels while maintaining the strength of the hydrogel at a neutral pH. This is thought to be the result of modification of the polypeptide with a bulky sugar chain with high water-solubility thus acting to suppress excessive association between peptide chains, improve the water-solubility of the assembly, or both.

From the above, it was found that sugar chain-polypeptide complexes which are (RADA)4 or (RADA)5 modified with various sugar chains can also form transparent and uniform hydrogels while maintaining the strength of the hydrogel at a neutral pH.

Example 3

Evaluation of Hydrogel Property by Steel Ball Loading Test-3

Similarly to the method of Example 1, steel ball loading tests were carried out with C(DiGlcNAc)-(RADA)4 having hydrogel concentrations of 1 wt. %, 0.5 wt. %, and 0.25 wt. %. The evaluation results obtained are shown in Table 3.

TABLE 3

| Compound | | No. of Sugar Residues | hydrogel concentration | pH 3.5 | pH 7.4 |
|---|---|---|---|---|---|
| No. | Name | | | | |
| 2 | C(DiGlcNAc)-(RADA)4 | 7 | 1 wt. % | ○ | ○ |
| | | | 0.5 wt. % | ○ | ○ |
| | | | 0.25 wt. % | X | ○ |

As shown in Table 3, C(DiGlcNAc)-(RADA)4 formed a uniform hydrogel at pH 7.4 even in a low concentration range. Moreover, C(DiGlcNAc)-(RADA)4 formed a uniform hydrogel only at pH 7.4 when the hydrogel concentration was lowered to 0.25 wt. %. From this, it was found that C(DiGlcNAc)-(RADA)4 can control hydrogel formation by pH when the hydrogel concentration is low.

In other words, it was found that the sugar chain-polypeptide complex of the present invention can form a transparent and uniform hydro gel while maintaining the strength of the hydrogel in an aqueous solution having a neutral pH even when the hydrogel concentration is low. It was further found that the sugar chain-polypeptide complex of the present invention can control hydrogel formation by pH when the hydrogel concentration is low.

Example 4

Evaluation of Hydrogel Property by Steel Ball Loading Test-4

With a method similar to Example 1 except that they were carried out with the hydrogel concentration at 0.5 wt. %, steel ball loading tests were carried out with C(DiGlcNAc)-(RADA)4, 2C(Maltose)-(RADA)4, 2C(Maltotriose)-(RADA)4, C(Maltose)-(RADA)4-C(Maltose), C(Maltotriose)-(RADA)4-C(Maltotriose), 3C(Maltose)-(RADA)4, (RADA)4-C(DiGlcNAc), C(Maltoheptaose)-(RADA)4, (RATARAEA)2, and C(DiGlcNAc)-(RATARAEA)2. The evaluation results obtained are shown in Table 4.

TABLE 4

| Compound | | No. of Sugar Residues | pH 3.5 | pH 7.4 |
|---|---|---|---|---|
| No. | Name | | | |
| 1 | (RADA)4 | — | X* | X* |
| 2 | C(DiGlcNAc)-(RADA)4 | 7 | ○ | ○ |
| 8 | 2C(Maltose)-(RADA)4 | 4 | ○* | X* |
| 9 | 2C(Maltotriose)-(RADA)4 | 6 | ○ | ○ |
| 10 | C(Maltose)-(RADA)4-C(Maltose) | 4 | ○* | X* |
| 11 | C(Maltotriose)-(RADA)4-C(Maltotriose) | 6 | ○ | ○ |
| 12 | 3C(Maltose)-(RADA)4 | 6 | ○ | ○ |
| 13 | (RADA)4-C(DiGlcNAc) | 7 | ○ | ○ |
| 14 | C(PEG2000)-(RADA)4 | — | X | X |
| 15 | C(PEG2000)-(RADA)5 | — | X | X |
| 16 | (RATARAEA)2 | — | X* | X* |
| 17 | C(DiGlcNAc)-(RATARAEA)2 | 7 | ○ | ○ |

As shown in Table 4, No. 2, 9, 11, 12, 13, and 17 in which the total number of sugar residues present in the sugar chain bound to the sugar chain-polypeptide complex is 5 or more formed transparent and uniform hydrogels at pH 3.5 and pH 7.4. Although not shown in the Table, a sugar chain-polypeptide complex having C(DiBn-Disialo) bound to the N-terminal of (RADA)4 (11 sugar residues) also formed a transparent and uniform hydrogel at pH 7.4. On the other hand, No. 8 and No. 10 in which the total number of sugar residues present in the sugar chain bound to the sugar chain-polypeptide complex is 4 or less did not form hydrogels at pH 7.4. In other words, it became clear that when a sugar chain in which the total number of sugar residues is 5 or more is bound to a polypeptide that has a self-assembling nature in an aqueous solution, said sugar chain-polypeptide complex comes to show high water-solubility and forms a transparent and uniform hydrogel in the neutral range.

Moreover, it became clear that a transparent and uniform hydrogel is formed at pH 3.5 and pH 7.4 not only when the sugar chain bound to the sugar chain-polypeptide complex possesses a branch by itself (such as diGlcNAc sugar chains of No. 2 and No. 13 as well as disialo and asialo sugar chains shown in Table 2), but also when it is linear sugar chains (such as maltose or maltotriose sugar chains), as long as the sugar chain possesses a branch in the sugar chain-polypeptide complex as a whole by having two or more bound to one polypeptide such as with No. 9, No. 11, and No. 12.

Moreover, although a method of binding PEG to the polypeptide is known in order to improve the water-solubility of the polypeptide, when PEG2000 was bound to (RADA)4 and (RADA)5 (No. 14 and No. 15), insoluble matters were not observed, but uniform hydrogels were not formed at pH 3.5 and pH 7.4. In other words, it became clear that the sugar chain-polypeptide complex of the present invention shows a higher water-solubility and forms a more transparent and uniform hydrogel compared to a PEG-polypeptide complex.

In addition, sugar chains are bound to the N- and C-terminal portion of the polypeptide in No. 11, and a sugar chain is bound to the C-terminal portion of the polypeptide in No. 13. Both of these showed high water-solubility and formed transparent and uniform hydrogels at pH 3.5 and pH 7.4. In other words, it became clear that in the sugar chain-polypeptide complex of the present invention, the sugar chain binding site may be not only the N-terminal portion but also the C-terminal portion of the polypeptide, as well as both terminal portions.

Further, similarly to (RADA)4 or (RADA)5, (RATARAEA)2 is known as a polypeptide that forms a hydrogel. Improvement of gel-forming capability when a sugar chain was bound to (RATARAEA)2 was evaluated with steel ball loading tests. As shown in Table 4, No. 16 in which no sugar chain is bound to (RATARAEA)2 formed an ununiform and clouded hydro gel, and the steel ball sank to the bottom of the Durham's tube at pH 3.5 and 7.4. On the other hand, No. 17 which is a sugar chain-polypeptide complex in which C(DiGlcNAc) is bound to the N-terminal portion of (RATARAEA)2 formed a transparent and uniform gel at pH 3.5 and pH 7.4. Although not shown in the Table, a sugar chain-polypeptide complex having C(Asialo) bound to the N-terminal of (RATARAEA)2 similarly formed a transparent and uniform hydrogel at pH 7.4. In other words, it became clear that a higher water-solubility is shown and a more transparent and uniform hydrogel is formed when a sugar chain is bound to a polypeptide comprising (RATARAEA)2.

From the above results, it was shown that a sugar chain-polypeptide complex that forms a transparent and uniform gel in a broad pH including the neutral range can be manufactured by binding a sugar chain not only to (RADA)4 but also to polypeptides of various sequences.

Example 5

Evaluation of Hydrogel Property by Steel Ball Loading Test-5

Steel ball loading tests with N(Asialo)-(RADA)4, N(DiGlcNAc)-(RADA)4, and C(DiGlcNAc)-(RADA)4 were carried out with a method similar to Example 1. The evaluation results obtained are shown in Table 5.

TABLE 5

| No. | Compound Name | No. of Sugar Residues | pH 3.5 | pH 7.4 |
|---|---|---|---|---|
| 2 | C(DiGlcNAc)-(RADA)4 | 7 | ○ | ○ |
| 18 | N(Asialo)-(RADA)4 | 9 | ○ | ○ |
| 19 | N(DiGlcNAc)-(RADA)4 | 7 | ○ | ○ |

As shown in Table 5, No. 18 and 19 which are asparagine-linked sugar chain-polypeptide complexes, similarly to No. 2 which is a cysteine-linked sugar chain-polypeptide complex, formed transparent and uniform hydrogels at pH 3.5 and pH 7.4. In other words, it became clear that the sugar chain-polypeptide complex of the present invention forms a transparent and uniform hydrogel even when the amino acid to which the sugar chain is bound is not cysteine.

Example 6

Investigation of Utility as Hemostatic Matrix

An evaluation test employing rat blood plasma was carried out in order to verify whether a hydrogel comprising the sugar chain-polypeptide complex of the present invention can be utilized as a hemostatic material.

Aqueous polypeptide solutions were prepared with a method similar to Example 1. Blood was collected from 7 weeks-old Crlj:WI rats with heparin sodium injection (Ajinomoto), and blood plasma was obtained from the supernatant after centrifugation treatment. The aqueous polypeptide solution, blood plasma, and PBS were added to a Durham's tube, and hydrogels was prepared so that the plasma concentration was 5-50% and the polypeptide concentration was 0.5 wt. %. Subsequently, these were left for 20 minutes at room temperature condition, and then steel ball loading tests were carried out with a method similar to Example 1. Photographs of the hydrogels after leaving for 20 minutes are shown in FIG. 2, and the evaluation results are shown in Table 6.

TABLE 6

| No. | Compound Name | plasma concentration 50% | 25% | 10% | 5% | Notes |
|---|---|---|---|---|---|---|
| 1 | (RADA)4 | Δ* | Δ* | X* | X* | Precipitate was verified at all concentrations Ball was retained on precipitate at 50% |
| 2 | C(DiGlcNAc)-(RADA)4 | ○ | ○ | ○ | ○ | |

Figure 2:
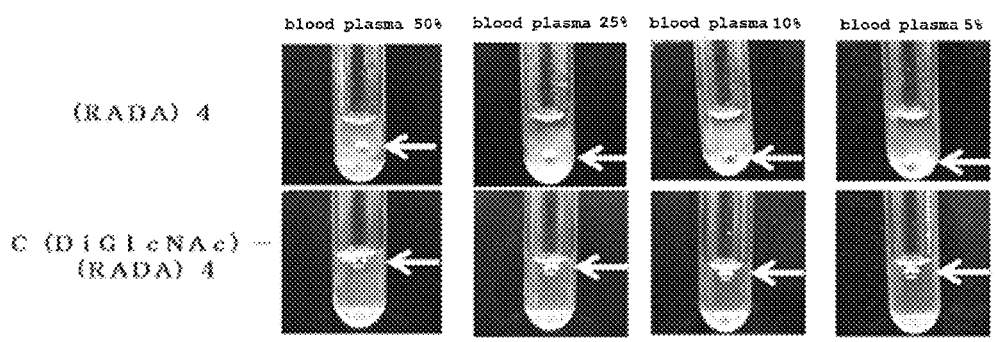
FIG. 2 is photographs showing the result of steel ball loading tests for (RADA)4 and C(DiGlcNAc)-(RADA)4 when comprising blood plasma at various concentrations.

As shown in FIG. 2 and Table 6, polypeptide solutions comprising C(DiGlcNAc)-(RADA)4 formed uniform hydrogels regardless of the plasma concentration. More surprisingly, C(DiGlcNAc)-(RADA)4 formed a uniform hydrogel even in a state of high concentration at 50% plasma concentration. On the other hand, for polypeptide solutions comprising (RADA)4, the polypeptide solution clouded and insoluble matters were observed at all plasma concentrations. Moreover, the pH of each hydrogel was verified, and all were between pH 6 and 8. In other words, it became clear that the sugar chain-polypeptide complex of the present invention not only forms a uniform hydrogel at a neutral pH, but also is less likely to produce insoluble matters, and forms a transparent hydrogel even in the presence of high concentration blood plasma.

From the above results, it was shown that the sugar chain-polypeptide complex of the present invention has extremely high utility value as a hemostatic pharmaceutical composition.

Example 7

Investigation of Controlled Release Capability for Acidic Protein

A test was carried out in order to investigate whether a hydrogel comprising the sugar chain-polypeptide complex of the present invention can be utilized as a controlled release carrier at a neutral pH.

A phosphate buffer (pH 7.4) was employed as the buffer. Moreover, Bovine Serum Albumin (BSA) fluorescently labeled with Alexa Fluor™ 488 (A13100, Life Technologies) was employed as the acidic protein to be encapsulated into the hydrogel.

Figure 3:
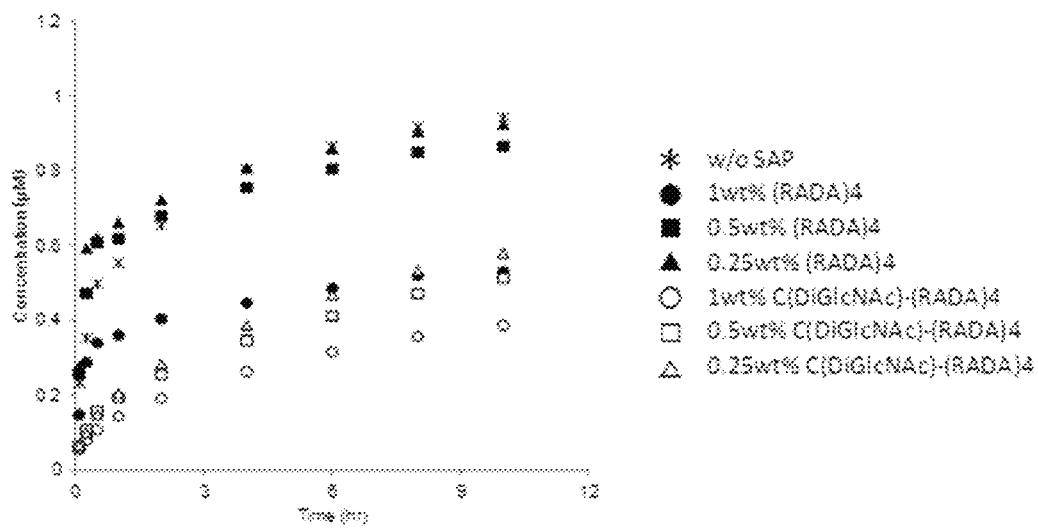
FIG. 3 is a graph showing the controlled release effect measurement results for (RADA)4 and C(DiGlcNAc)-(RADA)4 when encapsulating an acidic protein.

The components were added to the tube so that the buffer salt concentration is 0.15 M, the BSA concentration is 5 μM, and the polypeptide concentration is 0.25-1 wt. %, and mixed by vortex. The mixture was added to the Multiwell Insert System (351130, BD) at 50 μL each, and left overnight in an incubator at 37 degrees (CO2 incubator for cell culture, MCO-18AIC, SANYO) with shading to prepare BSA-encapsulating hydrogels. In the incubator at 37 degrees, the Insert System was immersed in a 96-well flat bottom plate (353928, BD) with a buffer identical to the hydrogel added at 225 µL each, and the plate was shaken with a plate shaker (MICRO PLATE MIXER NS-P, AS ONE Corporation, rotation speed: 1/5 of scale) to initiate the test (0 hours). Subsequently, the fluorescence amount that leaked out over time on the flat bottom plate side was measured with a fluorescence plate reader (SpectraMax M3, Molecular Devices, LLC.). A standard curve was created with the identical fluorescently-labeled BSA, and the protein concentration was calculated from the amount of fluorescent dye that leaked out. Results for a hydrogel comprising (RADA)4 and a hydrogel comprising C(DiGlcNAc)-(RADA)4 are shown in FIG. 3. A solution of only BSA added to the buffer (W/O SAP) was employed as the control. In FIG. 3, the Y axis shows the BSA concentration in the flat bottom plate and the X axis shows the time since the initiation of test.

As shown in FIG. 3, the majority of the BSA encapsulated in the hydrogel comprising (RADA)4 leaked out in a short time after the initiation of test. Moreover, its leakage speed when the polypeptide was 0.5 wt. % or less was equivalent to the leakage speed of the solution without any polypeptide, showing that it does not possess controlled release capability. On the other hand, with the hydrogel comprising C(DiGlcNAc)-(RADA)4, the leakage speed of BSA was slow compared to the solution without any polypeptide even at a concentration as low as 0.25 wt. %, showing controlled release capability.

In other words, it became clear that the sugar chain-polypeptide complex of the present invention encapsulates and retains an acidic protein at a neutral pH and possesses a controlled release effect.

Example 8

Investigation of Controlled Release Capability for Basic Protein

A controlled release test was carried out similarly to the method described in Example 7, except that a basic protein Lysozyme was employed as the protein to be encapsulated. Lysozyme was labeled with Alexa Fluor™ 488 by Alexa Fluor™ 488 Protein Labeling Kit (A10235, Invitrogen) for use. Results are shown in FIG. 4.

Figure 4:
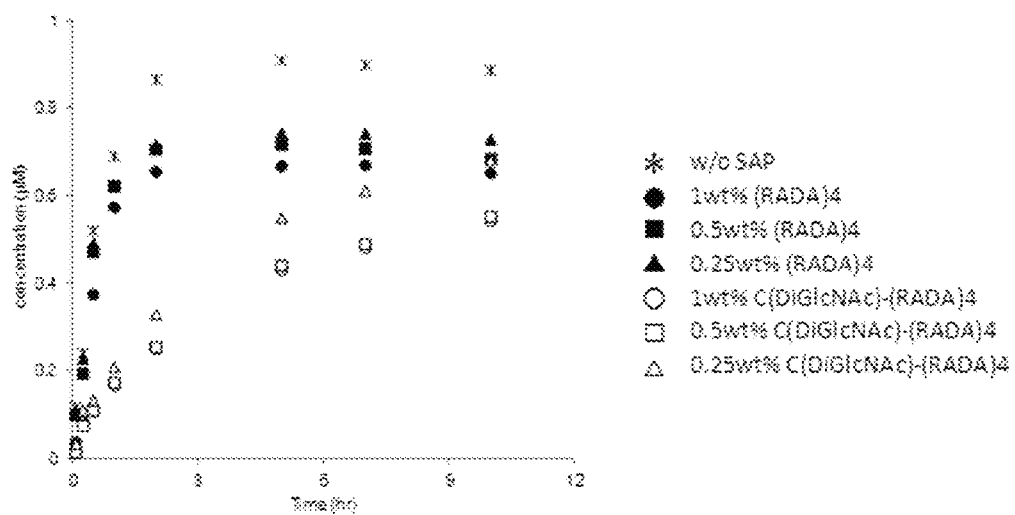
FIG. 4 is a graph showing the controlled release effect measurement results for (RADA)4 and C(DiGlcNAc)-(RADA)4 when encapsulating a basic protein.

As shown in FIG. 4, the majority of the Lysozyme encapsulated in the hydrogel comprising (RADA)4 leaked out within one hour after the initiation of test. Moreover, its leakage speed was almost equivalent to the leakage speed of the solution without any polypeptide, showing that it does not possess controlled release capability. On the other hand, with the hydrogel comprising C(DiGlcNAc)-(RADA)4, the leakage speed of Lysozyme was slow compared to the solution without any polypeptide even at a concentration as low as 0.25 wt. %, showing controlled release capability.

In other words, it became clear that the sugar chain-polypeptide complex of the present invention encapsulates and retains a basic protein at a neutral pH and possesses a controlled release effect.

Example 9

Measurement and Analysis of Circular Dichroism (CD)

CD measurement was carried out as a confirmation that the sugar chain-polypeptide complex of the present invention forms a β sheet structure. In general, the characteristics of the wavelengths observed when a substance has a β sheet structure are a positive absorption at around 197 nm and a negative absorption at around 216 nm. For this reason, focus was placed on the size of these wavelengths in the present invention, and the influence of pH on the β sheet structure was investigated.

C(DiGlcNAc)-(RADA)4 which is one embodiment of the present invention or (RADA)4 as the control were dissolved in ultrapure water. One to ten millimolars of aqueous sodium hydroxide solutions were added to each of these aqueous polypeptide solutions to adjust the pH, and 100 mM aqueous polypeptide solutions at having pH 2 or pH 7 were created. These aqueous solutions were transferred to quartz cells having an optical path length of 0.1 cm. The CD spectrum was then measured with a spectrum polarimeter (J-805, Jasco) at wavelengths of 185-260 nm for ellipticity (millidegree). The mean residue ellipticity θ was calculated with the following formula:

$$[\theta] = (\theta_{obs}/10 \cdot l \cdot c)/r$$

wherein $\theta_{obs}$ represents the ellipticity measured in millidegree, l represents the cell length (cm), c represents the concentration (M), and r represents the number of amino acid residues.

Figure 5:
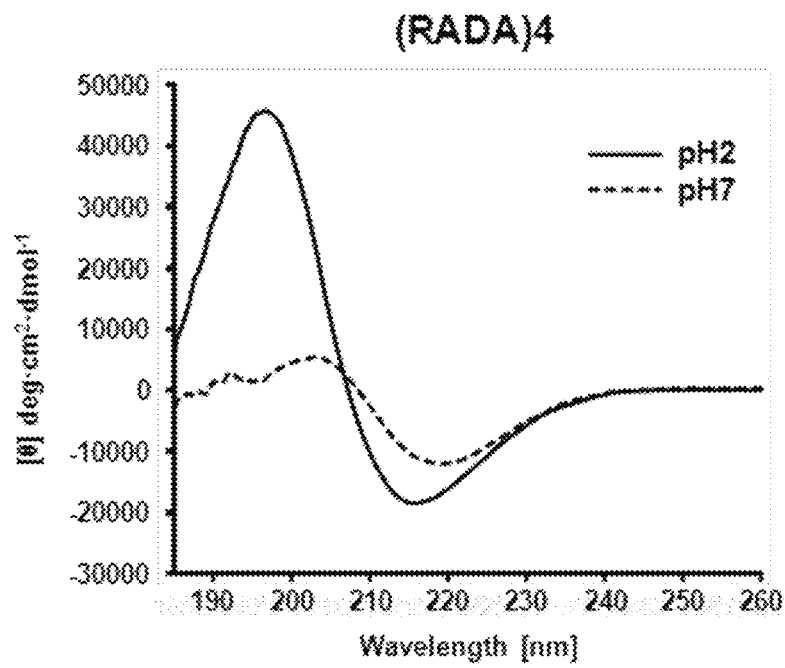
FIG. 5 is a graph showing the circular dichroism (CD) measurement results for (RADA)4 at pH 2 or pH 7.
Figure 6:
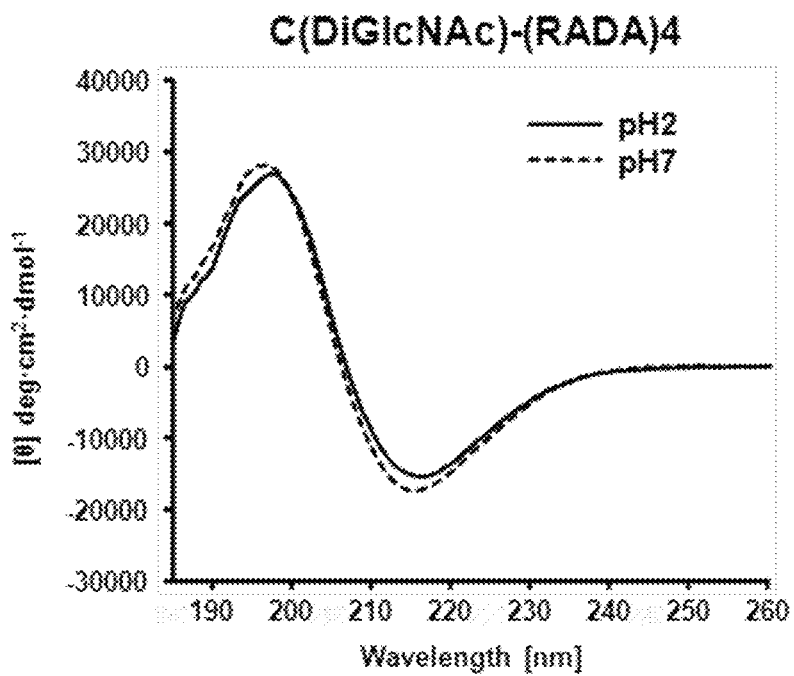
FIG. 6 is a graph showing the circular dichroism (CD) measurement results for C(DiGlcNAc)-(RADA)4 at pH 2 or pH 7.

The result for (RADA)4 is shown in FIG. 5, and the result for C(DiGlcNAc)-(RADA)4 is shown in FIG. 6.

As shown in FIGS. 5 and 6, (RADA)4 and C(DiGlcNAc)-(RADA)4 both showed high molar ellipticity at pH 2. On the other hand, C(DiGlcNAc)-(RADA)4 showed high molar ellipticity but the molar ellipticity of (RADA)4 was significantly reduced at pH 7. In other words, it became clear that (RADA)4 formed almost no β sheet structure at a neutral pH, whereas C(DiGlcNAc)-(RADA)4 forms a β sheet structure even at a neutral pH.

The above result is thought to be due to the suppression of excessive association of polypeptides with each other by the presence of sugar chains for C(DiGlcNAc)-(RADA)4 to maintain the β sheet, whereas for (RADA)4, β sheet was decreased because association was excessively promoted at neutral pH. This is consistent with the phenomenon where (RADA)4 produced clouding/precipitation at a neutral pH in the steel ball loading test and could not form a uniform and rigid hydrogel (e.g. FIG. 1).

From the above results, it was confirmed that the sugar chain-polypeptide complex of the present invention forms a β sheet structure at a neutral pH.

Example 10

Measurement and Analysis of Kinetic Viscosity

In addition to the strength of the hydrogel verified in the steel ball loading test, a kinetic viscosity measurement was carried out in order to observe the change in hydrogel strength or the stability of hydrogel over time.

A rheometer (MCR302, Anton Paar GmbH) equipped with a stainless steel parallel plate having a diameter of 25 mm with 0.3 mm gap height was employed for kinetic viscosity measurement. C(DiGlcNAc)-(RADA)4 which is one embodiment of the present invention or (RADA)4 as the control were dissolved in ultrapure water. Five millimolars of aqueous sodium hydroxide solution was added to these aqueous polypeptide solutions in order to adjust the pH to prepare 0.5 wt. % hydrogels at pH 7. Subsequently, these hydrogels were quickly transferred to a rheometer set at 25 degrees, and phase angle (tan δ) was monitored over a time course. (frequency=1 Hz, distortion=10%)

Figure 7:
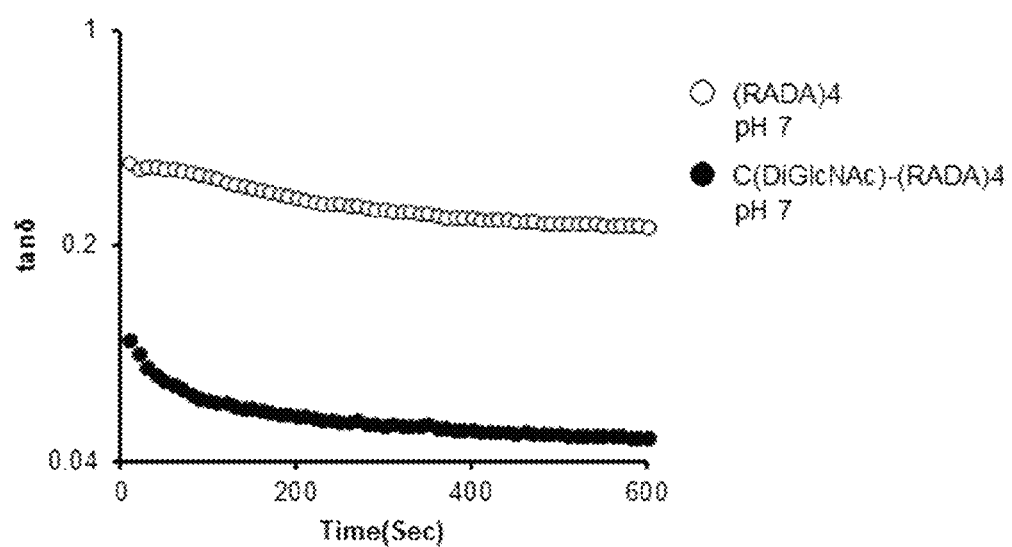
FIG. 7 is a graph showing the kinetic viscosity measurement results for (RADA)4 and C(DiGlcNAc)-(RADA)4 at pH 7.

This measurement result is shown in FIG. 7.

As shown in FIG. 7, it was shown that a rigid hydrogel was formed with the hydrogel comprising C(DiGlcNAc)-(RADA)4 since the phase angle decreased rapidly from the start of measurement. On the other hand, the hydrogel comprising (RADA)4 has a large phase angle, showing that a fragile hydrogel is formed, or an ununiform hydrogel that is only partially rigid is formed.

This is consistent with the phenomenon where (RADA)4 produced clouding/precipitation at a neutral pH in the steel ball loading test and could not form a uniform and rigid hydrogel (e.g. FIG. 1).

From the above results, it was confirmed that the sugar chain-polypeptide complex of the present invention forms a rigid hydrogel at a neutral pH.

The invention claimed is:

1. A sugar chain-polypeptide complex, wherein
said sugar chain polypeptide complex comprises a polypeptide comprising an amino acid sequence consisting of 8-34 amino acid residues in which polar and nonpolar amino acid residues are alternately arranged, and
one or more sugar chains are bound to said polypeptide, wherein the total number of sugar residues present in the one or more sugar chains bound to said polypeptide is 5-11.

2. The sugar chain-polypeptide complex according to claim 1, wherein said sugar chain-polypeptide complex forms a hydrogel comprising a βsheet structure by self-assembly in an aqueous solution having a pH around neutral.

3. The sugar chain-polypeptide complex according to claim 1, wherein each of said polar amino acid residues is an amino acid residue selected from the group consisting of an aspartate residue, a glutamate residue, an arginine residue, a lysine residue, a histidine residue, a tyrosine residue, a serine residue, a threonine residue, an asparagine residue, a glutamine residue, and a cysteine residue.

4. The sugar chain-polypeptide complex according to claim 1, wherein each of said nonpolar amino acid residues is an amino acid residue selected from the group consisting of an alanine residue, a valine residue, a leucine residue, an isoleucine residue, a methionine residue, a phenylalanine residue, a tryptophan residue, a proline residue, and a glycine residue.

5. The sugar chain-polypeptide complex according to claim 4, wherein
each of said polar amino acid residues is an amino acid residue selected from the group consisting of an aspartate residue, a glutamate residue, an arginine residue, and a threonine residue, and
each of said nonpolar amino acid residues is an alanine residue.

6. The sugar chain-polypeptide complex according to claim 1, wherein said amino acid sequence is a repetitive sequence of RADA (SEQ NO:61) or a repetitive sequence of RATARAEA (SEQ NO:62).

7. The sugar chain-polypeptide complex according to claim 6, wherein said amino acid sequence is an amino acid sequence selected from the group consisting of RADARADARADARADA (SEQ ID NO:1), RADARADARADARADARADA (SEQ ID NO:2), and RATARAEARATARAEA (SEQ ID NO:3).

8. The sugar chain-polypeptide complex according to claim 1, wherein the number of sugar chains bound to said polypeptide is 1, 2, or 3.

9. The sugar chain-polypeptide complex according to claim 1, wherein sugar chains are bound to every amino acid up to position x counting from the amino acid residue positioned at the N-terminal of said polypeptide and every amino acid up to position y counting from the amino acid residue positioned at the C-terminal, wherein x and y are integers, x≥0, y≥0, and x+y is the total number of sugar chains bound to the polypeptide.

10. The sugar chain-polypeptide complex according to claim 9,
wherein the number of sugar chains hound to said polypeptide is 1, 2, or 3, in which
when the number of sugar chains bound to said polypeptide is 1, said one sugar chain is bound to the amino acid residue positioned at the N-terminal of said polypeptide or the amino acid residue positioned at the C-terminal,
when the number of sugar chains bound to said polypeptide is 2, said two sugar chains are bound to amino acid residues selected from the group consisting of (1)-(3) below:
(1) the first and second amino acid residues counting from the amino acid residue positioned at the N-terminal of said polypeptide,
(2) the first and second amino acid residues counting from the amino acid residue positioned at the C-terminal of said polypeptide, and
(3) the amino acid residue positioned at the N-terminal of said polypeptide and the amino acid residue positioned at the C-terminal of said polypeptide, and
when the number of sugar chains bound to said polypeptide is 3, said three sugar chains are bound to any amino acid residue selected from the group consisting of (1)-(4) below:
(1) the first, second, and third amino acid residues counting from the amino acid residue positioned at the N-terminal of said polypeptide,
(2) the first, second, and third amino acid residues counting from the amino acid residue positioned at the C-terminal of said polypeptide,
(3) the first and second amino acid residues counting from the amino acid residue positioned at the N-terminal of said polypeptide, as well as the amino acid residue positioned at the C-terminal of said polypeptide, and
(4) the amino acid residue positioned at the N-terminal of said polypeptide, as well as amino acid residues positioned at position 1 and 2 counting from the C-terminal of said polypeptide.

11. The sugar chain-polypeptide complex according to claim 1, wherein said one or more sugar chains comprise a sugar chain with a branch.

12. The sugar chain-polypeptide complex according to claim 1, wherein said one or more sugar chains comprise a sugar chain selected from the group consisting of a disialo sugar chain, an asialo sugar chain, a diGlcNAc sugar chain, a dimannose sugar chain, a GlcNAc sugar chain, a maltotriose sugar chain, a maltose sugar chain, a maltotetraose sugar chain, a maltoheptaose sugar chain, β-cyclodextrin, and γ-cyclodextrin.

13. A composition for hydrogel formation comprising a sugar chain-polypeptide complex according to claim 1.

14. A composition comprising a sugar chain-polypeptide complex according to claim 1, wherein said composition is in a hydrogel state.

15. A hemostatic pharmaceutical composition comprising a composition according to claim 13.

16. A composition for controlled release carrier comprising a composition according to claim 13.

17. A composition for culture matrix comprising a composition according to claim 13.

* * * * *

UNITED STATES PATENT AND TRADEMARK OFFICE
CERTIFICATE OF CORRECTION

PATENT NO. : 9,981,059 B2
APPLICATION NO. : 14/780417
DATED : May 29, 2018
INVENTOR(S) : Saijo et al.

It is certified that error appears in the above-identified patent and that said Letters Patent is hereby corrected as shown below:

On the Title Page

Item (*) Notice: Please correct "0 days. days." to read -- 0 days. --

In the Specification

Column 41, Line 55: Please correct "7.42 yield" to read -- 7.42 μmol, yield --

Column 43, Line 17: Please correct "9.75 mol" to read -- 9.75 μmol --

Column 71, Line 22: Please correct "33 WI" to read -- 33 μM --

Column 72, Line 56, Chemical Formula 80: Please correct "Av-Cys-Arg-" to read -- Ac-Cys-Arg- --

In the Claims

Column 137, Claim 10, Line 60: Please correct "hound" to read -- bound --

Signed and Sealed this
Ninth Day of October, 2018

Andrei Iancu
*Director of the United States Patent and Trademark Office*

SEQUENCE LISTING

```
<160> NUMBER OF SEQ ID NOS: 62

<210> SEQ ID NO 1
<211> LENGTH: 16
<212> TYPE: PRT
<213> ORGANISM: Artificial
<220> FEATURE:
<223> OTHER INFORMATION: Chemically synthesized

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 20
<212> TYPE: PRT
<213> ORGANISM: Artificial
<220> FEATURE:
<223> OTHER INFORMATION: Chemically synthesized

<400> SEQUENCE: 2

Arg Ala Asp Ala Arg Ala Asp Ala Arg Ala Asp Ala Arg Ala Asp Ala
1               5                   10                  15

Arg Ala Asp Ala
            20

<210> SEQ ID NO 3
<211> LENGTH: 16
<212> TYPE: PRT
<213> ORGANISM: Artificial
<220> FEATURE:
<223> OTHER INFORMATION: Chemically synthesized

<400> SEQUENCE: 3

Arg Ala Thr Ala Arg Ala Glu Ala Arg Ala Thr Ala Arg Ala Glu Ala
1               5                   10                  15

<210> SEQ ID NO 4
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Trt
<220> FEATURE:
<221> NAME/KEY: BINDING
<222> LOCATION: (2)..(2)
<223> OTHER INFORMATION: Pbf
<220> FEATURE:
<221> NAME/KEY: BINDING
<222> LOCATION: (4)..(4)
<223> OTHER INFORMATION: OtBu
```

```
<220> FEATURE:
<221> NAME/KEY: BINDING
<222> LOCATION: (6)..(6)
<223> OTHER INFORMATION: Pbf
<220> FEATURE:
<221> NAME/KEY: BINDING
<222> LOCATION: (8)..(8)
<223> OTHER INFORMATION: OtBu
<220> FEATURE:
<221> NAME/KEY: BINDING
<222> LOCATION: (10)..(10)
<223> OTHER INFORMATION: Pbf
<220> FEATURE:
<221> NAME/KEY: BINDING
<222> LOCATION: (12)..(12)
<223> OTHER INFORMATION: OtBu
<220> FEATURE:
<221> NAME/KEY: BINDING
<222> LOCATION: (14)..(14)
<223> OTHER INFORMATION: Pbf
<220> FEATURE:
<221> NAME/KEY: BINDING
<222> LOCATION: (16)..(16)
<223> OTHER INFORMATION: OtBu
<220> FEATURE:
<221> NAME/KEY: BINDING
<222> LOCATION: (17)..(17)
<223> OTHER INFORMATION: Resin

<400> SEQUENCE: 4

Cys Arg Ala Asp Ala Arg Ala Asp Ala Arg Ala Asp Ala Arg Ala Asp
1               5                   10                  15

Ala

<210> SEQ ID NO 5
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (17)..(17)

<400> SEQUENCE: 5

Cys Arg Ala Asp Ala Arg Ala Asp Ala Arg Ala Asp Ala Arg Ala Asp
1               5                   10                  15

Ala

<210> SEQ ID NO 6
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: AMIDATION
<222> LOCATION: (17)..(17)

<400> SEQUENCE: 6

Cys Arg Ala Asp Ala Arg Ala Asp Ala Arg Ala Asp Ala Arg Ala Asp
1               5                   10                  15
```

Ala

<210> SEQ ID NO 7
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Asialo sugar chain added
<220> FEATURE:
<221> NAME/KEY: AMIDATION
<222> LOCATION: (17)..(17)

<400> SEQUENCE: 7

Cys Arg Ala Asp Ala Arg Ala Asp Ala Arg Ala Asp Ala Arg Ala Asp
1               5                   10                  15

Ala

<210> SEQ ID NO 8
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: DiGlcNAc sugar chain added
<220> FEATURE:
<221> NAME/KEY: AMIDATION
<222> LOCATION: (17)..(17)

<400> SEQUENCE: 8

Cys Arg Ala Asp Ala Arg Ala Asp Ala Arg Ala Asp Ala Arg Ala Asp
1               5                   10                  15

Ala

<210> SEQ ID NO 9
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: DiMan sugar chain added
<220> FEATURE:
<221> NAME/KEY: AMIDATION
<222> LOCATION: (17)..(17)

<400> SEQUENCE: 9

Cys Arg Ala Asp Ala Arg Ala Asp Ala Arg Ala Asp Ala Arg Ala Asp
1               5                   10                  15

Ala

```
<210> SEQ ID NO 10
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: GlcNAc sugar chain added
<220> FEATURE:
<221> NAME/KEY: AMIDATION
<222> LOCATION: (17)..(17)

<400> SEQUENCE: 10

Cys Arg Ala Asp Ala Arg Ala Asp Ala Arg Ala Asp Ala Arg Ala Asp
1               5                   10                  15

Ala

<210> SEQ ID NO 11
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Maltoheptaose sugar chain added
<220> FEATURE:
<221> NAME/KEY: AMIDATION
<222> LOCATION: (17)..(17)

<400> SEQUENCE: 11

Cys Arg Ala Asp Ala Arg Ala Asp Ala Arg Ala Asp Ala Arg Ala Asp
1               5                   10                  15

Ala

<210> SEQ ID NO 12
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: beta-cyclodextrin sugar chain added
<220> FEATURE:
<221> NAME/KEY: AMIDATION
<222> LOCATION: (17)..(17)

<400> SEQUENCE: 12

Cys Arg Ala Asp Ala Arg Ala Asp Ala Arg Ala Asp Ala Arg Ala Asp
1               5                   10                  15

Ala

<210> SEQ ID NO 13
<211> LENGTH: 17
<212> TYPE: PRT
<213> ORGANISM: Artificial
```

```
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: gamma-cyclodextrin sugar chain added
<220> FEATURE:
<221> NAME/KEY: AMIDATION
<222> LOCATION: (17)..(17)

<400> SEQUENCE: 13

Cys Arg Ala Asp Ala Arg Ala Asp Ala Arg Ala Asp Ala Arg Ala Asp
1               5                   10                  15

Ala

<210> SEQ ID NO 14
<211> LENGTH: 21
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Trt
<220> FEATURE:
<221> NAME/KEY: BINDING
<222> LOCATION: (2)..(2)
<223> OTHER INFORMATION: Pbf
<220> FEATURE:
<221> NAME/KEY: BINDING
<222> LOCATION: (4)..(4)
<223> OTHER INFORMATION: OtBu
<220> FEATURE:
<221> NAME/KEY: BINDING
<222> LOCATION: (6)..(6)
<223> OTHER INFORMATION: Pbf
<220> FEATURE:
<221> NAME/KEY: BINDING
<222> LOCATION: (8)..(8)
<223> OTHER INFORMATION: OtBu
<220> FEATURE:
<221> NAME/KEY: BINDING
<222> LOCATION: (10)..(10)
<223> OTHER INFORMATION: Pbf
<220> FEATURE:
<221> NAME/KEY: BINDING
<222> LOCATION: (12)..(12)
<223> OTHER INFORMATION: OtBu
<220> FEATURE:
<221> NAME/KEY: BINDING
<222> LOCATION: (14)..(14)
<223> OTHER INFORMATION: Pbf
<220> FEATURE:
<221> NAME/KEY: BINDING
<222> LOCATION: (16)..(16)
<223> OTHER INFORMATION: OtBu
<220> FEATURE:
<221> NAME/KEY: BINDING
<222> LOCATION: (18)..(18)
<223> OTHER INFORMATION: Pbf
<220> FEATURE:
<221> NAME/KEY: BINDING
<222> LOCATION: (20)..(20)
<223> OTHER INFORMATION: OtBu
<220> FEATURE:
<221> NAME/KEY: BINDING
<222> LOCATION: (21)..(21)
<223> OTHER INFORMATION: Resin
```

-continued

```
<400> SEQUENCE: 14

Cys Arg Ala Asp Ala Arg Ala Asp Ala Arg Ala Asp Ala Arg Ala Asp
1               5                   10                  15

Ala Arg Ala Asp Ala
            20

<210> SEQ ID NO 15
<211> LENGTH: 21
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (21)..(21)

<400> SEQUENCE: 15

Cys Arg Ala Asp Ala Arg Ala Asp Ala Arg Ala Asp Ala Arg Ala Asp
1               5                   10                  15

Ala Arg Ala Asp Ala
            20

<210> SEQ ID NO 16
<211> LENGTH: 21
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: AMIDATION
<222> LOCATION: (21)..(21)

<400> SEQUENCE: 16

Cys Arg Ala Asp Ala Arg Ala Asp Ala Arg Ala Asp Ala Arg Ala Asp
1               5                   10                  15

Ala Arg Ala Asp Ala
            20

<210> SEQ ID NO 17
<211> LENGTH: 21
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Asialo sugar chain added
<220> FEATURE:
<221> NAME/KEY: AMIDATION
<222> LOCATION: (21)..(21)

<400> SEQUENCE: 17

Cys Arg Ala Asp Ala Arg Ala Asp Ala Arg Ala Asp Ala Arg Ala Asp
1               5                   10                  15
```

Ala Arg Ala Asp Ala
        20

<210> SEQ ID NO 18
<211> LENGTH: 21
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: DiGlcNAc sugar chain added
<220> FEATURE:
<221> NAME/KEY: AMIDATION
<222> LOCATION: (21)..(21)

<400> SEQUENCE: 18

Cys Arg Ala Asp Ala Arg Ala Asp Ala Arg Ala Asp Ala Arg Ala Asp
1               5                   10                  15

Ala Arg Ala Asp Ala
        20

<210> SEQ ID NO 19
<211> LENGTH: 21
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: GlcNAc sugar chain added
<220> FEATURE:
<221> NAME/KEY: AMIDATION
<222> LOCATION: (21)..(21)

<400> SEQUENCE: 19

Cys Arg Ala Asp Ala Arg Ala Asp Ala Arg Ala Asp Ala Arg Ala Asp
1               5                   10                  15

Ala Arg Ala Asp Ala
        20

<210> SEQ ID NO 20
<211> LENGTH: 21
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: DiBn-Disialo sugar chain added
<220> FEATURE:
<221> NAME/KEY: AMIDATION
<222> LOCATION: (21)..(21)

<400> SEQUENCE: 20

Cys Arg Ala Asp Ala Arg Ala Asp Ala Arg Ala Asp Ala Arg Ala Asp
1               5                   10                  15

Ala Arg Ala Asp Ala
            20

<210> SEQ ID NO 21
<211> LENGTH: 21
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: BINDING
<222> LOCATION: (1)..(1)
<223> OTHER INFORMATION: PEG2000 added
<220> FEATURE:
<221> NAME/KEY: AMIDATION
<222> LOCATION: (21)..(21)

<400> SEQUENCE: 21

Cys Arg Ala Asp Ala Arg Ala Asp Ala Arg Ala Asp Ala Arg Ala Asp
1               5                   10                  15

Ala Arg Ala Asp Ala
            20

<210> SEQ ID NO 22
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Trt
<220> FEATURE:
<221> NAME/KEY: BINDING
<222> LOCATION: (2)..(2)
<223> OTHER INFORMATION: Pbf
<220> FEATURE:
<221> NAME/KEY: BINDING
<222> LOCATION: (4)..(4)
<223> OTHER INFORMATION: tBu
<220> FEATURE:
<221> NAME/KEY: BINDING
<222> LOCATION: (6)..(6)
<223> OTHER INFORMATION: Pbf
<220> FEATURE:
<221> NAME/KEY: BINDING
<222> LOCATION: (8)..(8)
<223> OTHER INFORMATION: OtBu
<220> FEATURE:
<221> NAME/KEY: BINDING
<222> LOCATION: (10)..(10)
<223> OTHER INFORMATION: Pbf
<220> FEATURE:
<221> NAME/KEY: BINDING
<222> LOCATION: (12)..(12)
<223> OTHER INFORMATION: tBu
<220> FEATURE:
<221> NAME/KEY: BINDING
<222> LOCATION: (14)..(14)
<223> OTHER INFORMATION: Pbf
<220> FEATURE:
<221> NAME/KEY: BINDING
<222> LOCATION: (16)..(16)
<223> OTHER INFORMATION: OtBu
<220> FEATURE:
<221> NAME/KEY: BINDING
<222> LOCATION: (17)..(17)

```
<223> OTHER INFORMATION: Resin

<400> SEQUENCE: 22

Cys Arg Ala Thr Ala Arg Ala Glu Ala Arg Ala Thr Ala Arg Ala Glu
1               5                   10                  15

Ala

<210> SEQ ID NO 23
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (17)..(17)

<400> SEQUENCE: 23

Cys Arg Ala Thr Ala Arg Ala Glu Ala Arg Ala Thr Ala Arg Ala Glu
1               5                   10                  15

Ala

<210> SEQ ID NO 24
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Asialo sugar chain added
<220> FEATURE:
<221> NAME/KEY: AMIDATION
<222> LOCATION: (17)..(17)

<400> SEQUENCE: 24

Cys Arg Ala Thr Ala Arg Ala Glu Ala Arg Ala Thr Ala Arg Ala Glu
1               5                   10                  15

Ala

<210> SEQ ID NO 25
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: DiGlcNAc sugar chain added
<220> FEATURE:
<221> NAME/KEY: AMIDATION
<222> LOCATION: (17)..(17)

<400> SEQUENCE: 25

Cys Arg Ala Thr Ala Arg Ala Glu Ala Arg Ala Thr Ala Arg Ala Glu
1               5                   10                  15

Ala
```

```
<210> SEQ ID NO 26
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Pbf
<220> FEATURE:
<221> NAME/KEY: BINDING
<222> LOCATION: (3)..(3)
<223> OTHER INFORMATION: Trt
<220> FEATURE:
<221> NAME/KEY: BINDING
<222> LOCATION: (5)..(5)
<223> OTHER INFORMATION: Pbf
<220> FEATURE:
<221> NAME/KEY: BINDING
<222> LOCATION: (7)..(7)
<223> OTHER INFORMATION: OtBu
<220> FEATURE:
<221> NAME/KEY: BINDING
<222> LOCATION: (9)..(9)
<223> OTHER INFORMATION: Pbf
<220> FEATURE:
<221> NAME/KEY: BINDING
<222> LOCATION: (11)..(11)
<223> OTHER INFORMATION: OtBu
<220> FEATURE:
<221> NAME/KEY: BINDING
<222> LOCATION: (13)..(13)
<223> OTHER INFORMATION: Pbf
<220> FEATURE:
<221> NAME/KEY: BINDING
<222> LOCATION: (15)..(15)
<223> OTHER INFORMATION: OtBu
<220> FEATURE:
<221> NAME/KEY: BINDING
<222> LOCATION: (16)..(16)
<223> OTHER INFORMATION: Resin

<400> SEQUENCE: 26

Arg Ala Cys Ala Arg Ala Asp Ala Arg Ala Asp Ala Arg Ala Asp Ala
1               5                   10                  15

<210> SEQ ID NO 27
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (16)..(16)

<400> SEQUENCE: 27

Arg Ala Cys Ala Arg Ala Asp Ala Arg Ala Asp Ala Arg Ala Asp Ala
1               5                   10                  15

<210> SEQ ID NO 28
<211> LENGTH: 16
<212> TYPE: PRT
<213> ORGANISM: Artificial
<220> FEATURE:
```

```
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (3)..(3)
<223> OTHER INFORMATION: Asialo sugar chain added
<220> FEATURE:
<221> NAME/KEY: AMIDATION
<222> LOCATION: (16)..(16)

<400> SEQUENCE: 28

Arg Ala Cys Ala Arg Ala Asp Ala Arg Ala Asp Ala Arg Ala Asp Ala
1               5                   10                  15

<210> SEQ ID NO 29
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (3)..(3)
<223> OTHER INFORMATION: DiGlcNAc sugar chain added
<220> FEATURE:
<221> NAME/KEY: AMIDATION
<222> LOCATION: (16)..(16)

<400> SEQUENCE: 29

Arg Ala Cys Ala Arg Ala Asp Ala Arg Ala Asp Ala Arg Ala Asp Ala
1               5                   10                  15

<210> SEQ ID NO 30
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Pbf
<220> FEATURE:
<221> NAME/KEY: BINDING
<222> LOCATION: (2)..(2)
<223> OTHER INFORMATION: Trt
<220> FEATURE:
<221> NAME/KEY: BINDING
<222> LOCATION: (3)..(3)
<223> OTHER INFORMATION: OtBu
<220> FEATURE:
<221> NAME/KEY: BINDING
<222> LOCATION: (5)..(5)
<223> OTHER INFORMATION: Pbf
<220> FEATURE:
<221> NAME/KEY: BINDING
<222> LOCATION: (7)..(7)
<223> OTHER INFORMATION: OtBu
<220> FEATURE:
<221> NAME/KEY: BINDING
<222> LOCATION: (9)..(9)
<223> OTHER INFORMATION: Pbf
<220> FEATURE:
<221> NAME/KEY: BINDING
<222> LOCATION: (11)..(11)
<223> OTHER INFORMATION: OtBu
```

```
<220> FEATURE:
<221> NAME/KEY: BINDING
<222> LOCATION: (13)..(13)
<223> OTHER INFORMATION: Pbf
<220> FEATURE:
<221> NAME/KEY: BINDING
<222> LOCATION: (15)..(15)
<223> OTHER INFORMATION: OtBu
<220> FEATURE:
<221> NAME/KEY: BINDING
<222> LOCATION: (16)..(16)
<223> OTHER INFORMATION: Resin

<400> SEQUENCE: 30

Arg Cys Asp Ala Arg Ala Asp Ala Arg Ala Asp Ala Arg Ala Asp Ala
1               5                   10                  15

<210> SEQ ID NO 31
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (16)..(16)

<400> SEQUENCE: 31

Arg Cys Asp Ala Arg Ala Asp Ala Arg Ala Asp Ala Arg Ala Asp Ala
1               5                   10                  15

<210> SEQ ID NO 32
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (2)..(2)
<223> OTHER INFORMATION: Asialo sugar chain added
<220> FEATURE:
<221> NAME/KEY: AMIDATION
<222> LOCATION: (16)..(16)

<400> SEQUENCE: 32

Arg Cys Asp Ala Arg Ala Asp Ala Arg Ala Asp Ala Arg Ala Asp Ala
1               5                   10                  15

<210> SEQ ID NO 33
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (2)..(2)
<223> OTHER INFORMATION: DiGlcNAc sugar chain added
<220> FEATURE:
<221> NAME/KEY: AMIDATION
<222> LOCATION: (16)..(16)

<400> SEQUENCE: 33
```

```
Arg Cys Asp Ala Arg Ala Asp Ala Arg Ala Asp Ala Arg Ala Asp Ala
1               5                   10                  15
```

<210> SEQ ID NO 34
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Trt
<220> FEATURE:
<221> NAME/KEY: BINDING
<222> LOCATION: (3)..(3)
<223> OTHER INFORMATION: OtBu
<220> FEATURE:
<221> NAME/KEY: BINDING
<222> LOCATION: (5)..(5)
<223> OTHER INFORMATION: Pbf
<220> FEATURE:
<221> NAME/KEY: BINDING
<222> LOCATION: (7)..(7)
<223> OTHER INFORMATION: OtBu
<220> FEATURE:
<221> NAME/KEY: BINDING
<222> LOCATION: (9)..(9)
<223> OTHER INFORMATION: Pbf
<220> FEATURE:
<221> NAME/KEY: BINDING
<222> LOCATION: (11)..(11)
<223> OTHER INFORMATION: OtBu
<220> FEATURE:
<221> NAME/KEY: BINDING
<222> LOCATION: (13)..(13)
<223> OTHER INFORMATION: Pbf
<220> FEATURE:
<221> NAME/KEY: BINDING
<222> LOCATION: (15)..(15)
<223> OTHER INFORMATION: OtBu
<220> FEATURE:
<221> NAME/KEY: BINDING
<222> LOCATION: (16)..(16)
<223> OTHER INFORMATION: Resin

<400> SEQUENCE: 34

```
Cys Ala Asp Ala Arg Ala Asp Ala Arg Ala Asp Ala Arg Ala Asp Ala
1               5                   10                  15
```

<210> SEQ ID NO 35
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (16)..(16)

<400> SEQUENCE: 35

```
Cys Ala Asp Ala Arg Ala Asp Ala Arg Ala Asp Ala Arg Ala Asp Ala
1               5                   10                  15
```

<210> SEQ ID NO 36
<211> LENGTH: 16

```
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Asialo sugar chain added
<220> FEATURE:
<221> NAME/KEY: AMIDATION
<222> LOCATION: (16)..(16)

<400> SEQUENCE: 36

Cys Ala Asp Ala Arg Ala Asp Ala Arg Ala Asp Ala Arg Ala Asp Ala
1               5                   10                  15

<210> SEQ ID NO 37
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: DiGlcNAc sugar chain added
<220> FEATURE:
<221> NAME/KEY: AMIDATION
<222> LOCATION: (16)..(16)

<400> SEQUENCE: 37

Cys Ala Asp Ala Arg Ala Asp Ala Arg Ala Asp Ala Arg Ala Asp Ala
1               5                   10                  15

<210> SEQ ID NO 38
<211> LENGTH: 18
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Trt
<220> FEATURE:
<221> NAME/KEY: BINDING
<222> LOCATION: (2)..(2)
<223> OTHER INFORMATION: Trt
<220> FEATURE:
<221> NAME/KEY: BINDING
<222> LOCATION: (3)..(3)
<223> OTHER INFORMATION: Pbf
<220> FEATURE:
<221> NAME/KEY: BINDING
<222> LOCATION: (5)..(5)
<223> OTHER INFORMATION: OtBu
<220> FEATURE:
<221> NAME/KEY: BINDING
<222> LOCATION: (7)..(7)
<223> OTHER INFORMATION: Pbf
<220> FEATURE:
<221> NAME/KEY: BINDING
<222> LOCATION: (9)..(9)
<223> OTHER INFORMATION: OtBu
<220> FEATURE:
```

```
<221> NAME/KEY: BINDING
<222> LOCATION: (11)..(11)
<223> OTHER INFORMATION: Pbf
<220> FEATURE:
<221> NAME/KEY: BINDING
<222> LOCATION: (13)..(13)
<223> OTHER INFORMATION: OtBu
<220> FEATURE:
<221> NAME/KEY: BINDING
<222> LOCATION: (15)..(15)
<223> OTHER INFORMATION: Pbf
<220> FEATURE:
<221> NAME/KEY: BINDING
<222> LOCATION: (17)..(17)
<223> OTHER INFORMATION: OtBu
<220> FEATURE:
<221> NAME/KEY: BINDING
<222> LOCATION: (18)..(18)
<223> OTHER INFORMATION: Resin

<400> SEQUENCE: 38

Cys Cys Arg Ala Asp Ala Arg Ala Asp Ala Arg Ala Asp Ala Arg Ala
1               5                   10                  15

Asp Ala

<210> SEQ ID NO 39
<211> LENGTH: 18
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (18)..(18)

<400> SEQUENCE: 39

Cys Cys Arg Ala Asp Ala Arg Ala Asp Ala Arg Ala Asp Ala Arg Ala
1               5                   10                  15

Asp Ala

<210> SEQ ID NO 40
<211> LENGTH: 18
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Maltose sugar chain added
<220> FEATURE:
<221> NAME/KEY: CARBOHYD
<222> LOCATION: (2)..(2)
<223> OTHER INFORMATION: Maltose sugar chain added
<220> FEATURE:
<221> NAME/KEY: AMIDATION
<222> LOCATION: (18)..(18)

<400> SEQUENCE: 40

Cys Cys Arg Ala Asp Ala Arg Ala Asp Ala Arg Ala Asp Ala Arg Ala
1               5                   10                  15

Asp Ala

<210> SEQ ID NO 41
```

-continued

```
<211> LENGTH: 18
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Maltotriose sugar chain added
<220> FEATURE:
<221> NAME/KEY: CARBOHYD
<222> LOCATION: (2)..(2)
<223> OTHER INFORMATION: Maltotriose sugar chain added
<220> FEATURE:
<221> NAME/KEY: AMIDATION
<222> LOCATION: (18)..(18)

<400> SEQUENCE: 41

Cys Cys Arg Ala Asp Ala Arg Ala Asp Ala Arg Ala Asp Ala Arg Ala
1               5                   10                  15

Asp Ala

<210> SEQ ID NO 42
<211> LENGTH: 18
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Maltotetraose sugar chain added
<220> FEATURE:
<221> NAME/KEY: CARBOHYD
<222> LOCATION: (2)..(2)
<223> OTHER INFORMATION: Maltotetraose sugar chain added
<220> FEATURE:
<221> NAME/KEY: AMIDATION
<222> LOCATION: (18)..(18)

<400> SEQUENCE: 42

Cys Cys Arg Ala Asp Ala Arg Ala Asp Ala Arg Ala Asp Ala Arg Ala
1               5                   10                  15

Asp Ala

<210> SEQ ID NO 43
<211> LENGTH: 19
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Trt
<220> FEATURE:
<221> NAME/KEY: BINDING
<222> LOCATION: (2)..(2)
<223> OTHER INFORMATION: Trt
<220> FEATURE:
<221> NAME/KEY: BINDING
<222> LOCATION: (3)..(3)
<223> OTHER INFORMATION: Trt
```

```
<220> FEATURE:
<221> NAME/KEY: BINDING
<222> LOCATION: (4)..(4)
<223> OTHER INFORMATION: Pbf
<220> FEATURE:
<221> NAME/KEY: BINDING
<222> LOCATION: (6)..(6)
<223> OTHER INFORMATION: OtBu
<220> FEATURE:
<221> NAME/KEY: BINDING
<222> LOCATION: (8)..(8)
<223> OTHER INFORMATION: Pbf
<220> FEATURE:
<221> NAME/KEY: BINDING
<222> LOCATION: (10)..(10)
<223> OTHER INFORMATION: OtBu
<220> FEATURE:
<221> NAME/KEY: BINDING
<222> LOCATION: (12)..(12)
<223> OTHER INFORMATION: Pbf
<220> FEATURE:
<221> NAME/KEY: BINDING
<222> LOCATION: (14)..(14)
<223> OTHER INFORMATION: OtBu
<220> FEATURE:
<221> NAME/KEY: BINDING
<222> LOCATION: (16)..(16)
<223> OTHER INFORMATION: Pbf
<220> FEATURE:
<221> NAME/KEY: BINDING
<222> LOCATION: (18)..(18)
<223> OTHER INFORMATION: OtBu
<220> FEATURE:
<221> NAME/KEY: BINDING
<222> LOCATION: (19)..(19)
<223> OTHER INFORMATION: Resin

<400> SEQUENCE: 43

Cys Cys Cys Arg Ala Asp Ala Arg Ala Asp Ala Arg Ala Asp Ala Arg
1               5                   10                  15

Ala Asp Ala

<210> SEQ ID NO 44
<211> LENGTH: 19
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (19)..(19)

<400> SEQUENCE: 44

Cys Cys Cys Arg Ala Asp Ala Arg Ala Asp Ala Arg Ala Asp Ala Arg
1               5                   10                  15

Ala Asp Ala

<210> SEQ ID NO 45
<211> LENGTH: 19
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Maltose sugar chain added
```

```
<220> FEATURE:
<221> NAME/KEY: CARBOHYD
<222> LOCATION: (2)..(2)
<223> OTHER INFORMATION: Maltose sugar chain added
<220> FEATURE:
<221> NAME/KEY: CARBOHYD
<222> LOCATION: (3)..(3)
<223> OTHER INFORMATION: Maltose sugar chain added
<220> FEATURE:
<221> NAME/KEY: AMIDATION
<222> LOCATION: (19)..(19)

<400> SEQUENCE: 45

Cys Cys Cys Arg Ala Asp Ala Arg Ala Asp Ala Arg Ala Asp Ala Arg
1               5                   10                  15

Ala Asp Ala

<210> SEQ ID NO 46
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Pbf
<220> FEATURE:
<221> NAME/KEY: BINDING
<222> LOCATION: (3)..(3)
<223> OTHER INFORMATION: OtBu
<220> FEATURE:
<221> NAME/KEY: BINDING
<222> LOCATION: (5)..(5)
<223> OTHER INFORMATION: Pbf
<220> FEATURE:
<221> NAME/KEY: BINDING
<222> LOCATION: (7)..(7)
<223> OTHER INFORMATION: OtBu
<220> FEATURE:
<221> NAME/KEY: BINDING
<222> LOCATION: (9)..(9)
<223> OTHER INFORMATION: Trt
<220> FEATURE:
<221> NAME/KEY: BINDING
<222> LOCATION: (11)..(11)
<223> OTHER INFORMATION: Pbf
<220> FEATURE:
<221> NAME/KEY: BINDING
<222> LOCATION: (13)..(13)
<223> OTHER INFORMATION: OtBu
<220> FEATURE:
<221> NAME/KEY: BINDING
<222> LOCATION: (15)..(15)
<223> OTHER INFORMATION: Pbf
<220> FEATURE:
<221> NAME/KEY: BINDING
<222> LOCATION: (17)..(17)
<223> OTHER INFORMATION: OtBu
<220> FEATURE:
<221> NAME/KEY: BINDING
<222> LOCATION: (17)..(17)
<223> OTHER INFORMATION: Resin

<400> SEQUENCE: 46

Arg Ala Asp Ala Arg Ala Asp Ala Cys Ala Arg Ala Asp Ala Arg Ala
1               5                   10                  15

Asp
```

```
<210> SEQ ID NO 47
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (17)..(17)

<400> SEQUENCE: 47

Arg Ala Asp Ala Arg Ala Asp Ala Cys Ala Arg Ala Asp Ala Arg Ala
1               5                   10                  15

Asp

<210> SEQ ID NO 48
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (9)..(9)
<223> OTHER INFORMATION: Maltose sugar chain added
<220> FEATURE:
<221> NAME/KEY: AMIDATION
<222> LOCATION: (17)..(17)

<400> SEQUENCE: 48

Arg Ala Asp Ala Arg Ala Asp Ala Cys Ala Arg Ala Asp Ala Arg Ala
1               5                   10                  15

Asp

<210> SEQ ID NO 49
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (9)..(9)
<223> OTHER INFORMATION: Maltotriose sugar chain added
<220> FEATURE:
<221> NAME/KEY: AMIDATION
<222> LOCATION: (17)..(17)

<400> SEQUENCE: 49

Arg Ala Asp Ala Arg Ala Asp Ala Cys Ala Arg Ala Asp Ala Arg Ala
1               5                   10                  15

Asp

<210> SEQ ID NO 50
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
```

```
<222> LOCATION: (1)..(1)
<220> FEATURE:
<221> NAME/KEY: CARBOHYD
<222> LOCATION: (9)..(9)
<223> OTHER INFORMATION: Maltotetraose sugar chain added
<220> FEATURE:
<221> NAME/KEY: AMIDATION
<222> LOCATION: (17)..(17)

<400> SEQUENCE: 50

Arg Ala Asp Ala Arg Ala Asp Ala Cys Ala Arg Ala Asp Ala Arg Ala
1               5                   10                  15
Asp

<210> SEQ ID NO 51
<211> LENGTH: 18
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Trt
<220> FEATURE:
<221> NAME/KEY: BINDING
<222> LOCATION: (2)..(2)
<223> OTHER INFORMATION: Pbf
<220> FEATURE:
<221> NAME/KEY: BINDING
<222> LOCATION: (4)..(4)
<223> OTHER INFORMATION: OtBu
<220> FEATURE:
<221> NAME/KEY: BINDING
<222> LOCATION: (6)..(6)
<223> OTHER INFORMATION: Pbf
<220> FEATURE:
<221> NAME/KEY: BINDING
<222> LOCATION: (8)..(8)
<223> OTHER INFORMATION: OtBu
<220> FEATURE:
<221> NAME/KEY: BINDING
<222> LOCATION: (10)..(10)
<223> OTHER INFORMATION: Pbf
<220> FEATURE:
<221> NAME/KEY: BINDING
<222> LOCATION: (12)..(12)
<223> OTHER INFORMATION: OtBu
<220> FEATURE:
<221> NAME/KEY: BINDING
<222> LOCATION: (14)..(14)
<223> OTHER INFORMATION: Pbf
<220> FEATURE:
<221> NAME/KEY: BINDING
<222> LOCATION: (16)..(16)
<223> OTHER INFORMATION: OtBu
<220> FEATURE:
<221> NAME/KEY: BINDING
<222> LOCATION: (18)..(18)
<223> OTHER INFORMATION: Trt
<220> FEATURE:
<221> NAME/KEY: BINDING
<222> LOCATION: (18)..(18)
<223> OTHER INFORMATION: Resin

<400> SEQUENCE: 51

Cys Arg Ala Asp Ala Arg Ala Asp Ala Arg Ala Asp Ala Arg Ala Asp
1               5                   10                  15
Ala Cys
```

```
<210> SEQ ID NO 52
<211> LENGTH: 18
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (18)..(18)

<400> SEQUENCE: 52

Cys Arg Ala Asp Ala Arg Ala Asp Ala Arg Ala Asp Ala Arg Ala Asp
1               5                   10                  15

Ala Cys

<210> SEQ ID NO 53
<211> LENGTH: 18
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Maltose sugar chain added
<220> FEATURE:
<221> NAME/KEY: CARBOHYD
<222> LOCATION: (18)..(18)
<223> OTHER INFORMATION: Maltose sugar chain added
<220> FEATURE:
<221> NAME/KEY: AMIDATION
<222> LOCATION: (18)..(18)

<400> SEQUENCE: 53

Cys Arg Ala Asp Ala Arg Ala Asp Ala Arg Ala Asp Ala Arg Ala Asp
1               5                   10                  15

Ala Cys

<210> SEQ ID NO 54
<211> LENGTH: 18
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Maltotriose sugar chain added
<220> FEATURE:
<221> NAME/KEY: CARBOHYD
<222> LOCATION: (18)..(18)
<223> OTHER INFORMATION: Maltotriose sugar chain added
<220> FEATURE:
<221> NAME/KEY: AMIDATION
<222> LOCATION: (18)..(18)

<400> SEQUENCE: 54

Cys Arg Ala Asp Ala Arg Ala Asp Ala Arg Ala Asp Ala Arg Ala Asp
1               5                   10                  15

Ala Cys
```

```
<210> SEQ ID NO 55
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Pbf
<220> FEATURE:
<221> NAME/KEY: BINDING
<222> LOCATION: (3)..(3)
<223> OTHER INFORMATION: OtBu
<220> FEATURE:
<221> NAME/KEY: BINDING
<222> LOCATION: (5)..(5)
<223> OTHER INFORMATION: Pbf
<220> FEATURE:
<221> NAME/KEY: BINDING
<222> LOCATION: (7)..(7)
<223> OTHER INFORMATION: OtBu
<220> FEATURE:
<221> NAME/KEY: BINDING
<222> LOCATION: (9)..(9)
<223> OTHER INFORMATION: Pbf
<220> FEATURE:
<221> NAME/KEY: BINDING
<222> LOCATION: (11)..(11)
<223> OTHER INFORMATION: OtBu
<220> FEATURE:
<221> NAME/KEY: BINDING
<222> LOCATION: (13)..(13)
<223> OTHER INFORMATION: Pbf
<220> FEATURE:
<221> NAME/KEY: BINDING
<222> LOCATION: (15)..(15)
<223> OTHER INFORMATION: OtBu
<220> FEATURE:
<221> NAME/KEY: BINDING
<222> LOCATION: (17)..(17)
<223> OTHER INFORMATION: Trt
<220> FEATURE:
<221> NAME/KEY: BINDING
<222> LOCATION: (17)..(17)
<223> OTHER INFORMATION: Resin

<400> SEQUENCE: 55

Arg Ala Asp Ala Arg Ala Asp Ala Arg Ala Asp Ala Arg Ala Asp Ala
1               5                   10                  15

Cys

<210> SEQ ID NO 56
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: AMIDATION
<222> LOCATION: (17)..(17)

<400> SEQUENCE: 56

Arg Ala Asp Ala Arg Ala Asp Ala Arg Ala Asp Ala Arg Ala Asp Ala
1               5                   10                  15

Cys
```

```
<210> SEQ ID NO 57
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (17)..(17)
<223> OTHER INFORMATION: DiGlcNAc sugar chain added
<220> FEATURE:
<221> NAME/KEY: AMIDATION
<222> LOCATION: (17)..(17)

<400> SEQUENCE: 57

Arg Ala Asp Ala Arg Ala Asp Ala Arg Ala Asp Ala Arg Ala Asp Ala
1               5                   10                  15

Cys

<210> SEQ ID NO 58
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Pbf
<220> FEATURE:
<221> NAME/KEY: BINDING
<222> LOCATION: (3)..(3)
<223> OTHER INFORMATION: OtBu
<220> FEATURE:
<221> NAME/KEY: BINDING
<222> LOCATION: (5)..(5)
<223> OTHER INFORMATION: Pbf
<220> FEATURE:
<221> NAME/KEY: BINDING
<222> LOCATION: (7)..(7)
<223> OTHER INFORMATION: OtBu
<220> FEATURE:
<221> NAME/KEY: BINDING
<222> LOCATION: (9)..(9)
<223> OTHER INFORMATION: Pbf
<220> FEATURE:
<221> NAME/KEY: BINDING
<222> LOCATION: (11)..(11)
<223> OTHER INFORMATION: OtBu
<220> FEATURE:
<221> NAME/KEY: BINDING
<222> LOCATION: (13)..(13)
<223> OTHER INFORMATION: Pbf
<220> FEATURE:
<221> NAME/KEY: BINDING
<222> LOCATION: (15)..(15)
<223> OTHER INFORMATION: OtBu
<220> FEATURE:
<221> NAME/KEY: BINDING
<222> LOCATION: (16)..(16)
<223> OTHER INFORMATION: Resin

<400> SEQUENCE: 58

Arg Ala Asp Ala Arg Ala Asp Ala Arg Ala Asp Ala Arg Ala Asp Ala
1               5                   10                  15
```

```
<210> SEQ ID NO 59
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: Asialo sugar chain added
<220> FEATURE:
<221> NAME/KEY: AMIDATION
<222> LOCATION: (17)..(17)

<400> SEQUENCE: 59

Asn Arg Ala Asp Ala Arg Ala Asp Ala Arg Ala Asp Ala Arg Ala Asp
1               5                   10                  15

Ala

<210> SEQ ID NO 60
<211> LENGTH: 17
<212> TYPE: PRT
<213> ORGANISM: Artificial
<220> FEATURE:
<223> OTHER INFORMATION: Chemically synthesized
<220> FEATURE:
<221> NAME/KEY: ACETYLATION
<222> LOCATION: (1)..(1)
<220> FEATURE:
<221> NAME/KEY: CARBOHYD
<222> LOCATION: (1)..(1)
<223> OTHER INFORMATION: DiGlcNAc sugar chain added
<220> FEATURE:
<221> NAME/KEY: AMIDATION
<222> LOCATION: (17)..(17)

<400> SEQUENCE: 60

Asn Arg Ala Asp Ala Arg Ala Asp Ala Arg Ala Asp Ala Arg Ala Asp
1               5                   10                  15

Ala

<210> SEQ ID NO 61
<211> LENGTH: 4
<212> TYPE: PRT
<213> ORGANISM: Artificial
<220> FEATURE:
<223> OTHER INFORMATION: Chemically synthesized

<400> SEQUENCE: 61

Arg Ala Asp Ala
1

<210> SEQ ID NO 62
<211> LENGTH: 8
<212> TYPE: PRT
<213> ORGANISM: Artificial
<220> FEATURE:
<223> OTHER INFORMATION: Chemically synthesized

<400> SEQUENCE: 62

Arg Ala Thr Ala Arg Ala Glu Ala
1               5
```